US009755155B2

United States Patent
Fuhrmann et al.

(10) Patent No.: US 9,755,155 B2
(45) Date of Patent: Sep. 5, 2017

(54) ORGANIC COMPOUNDS CONTAINING SQUARIC ACID OR CROCONIC ACID MOIETIES FOR APPLICATION IN ELECTRONIC DEVICES

(71) Applicant: SONY CORPORATION, Minato-ku (JP)

(72) Inventors: Gerda Fuhrmann, Stuttgart (DE); David Danner, Bermaringen (DE); Markus Obermaier, Stuttgart (DE); Ameneh Bamedi Zilai, Stuttgart (DE); Gabriele Nelles, Stuttgart (DE); Lars Peter Scheller, Waiblingen (DE)

(73) Assignee: SONY CORPORATION, Tokyo (JP)

( * ) Notice: Subject to any disclaimer, the term of this patent is extended or adjusted under 35 U.S.C. 154(b) by 0 days.

(21) Appl. No.: 14/398,291

(22) PCT Filed: Apr. 8, 2013

(86) PCT No.: PCT/EP2013/001031
§ 371 (c)(1),
(2) Date: Oct. 31, 2014

(87) PCT Pub. No.: WO2013/167222
PCT Pub. Date: Nov. 14, 2013

(65) Prior Publication Data
US 2015/0133678 A1 May 14, 2015

(30) Foreign Application Priority Data

May 7, 2012 (EP) .................................... 12167017

(51) Int. Cl.
| | | |
|---|---|---|
| *C07C 35/04* | (2006.01) | |
| *C07C 225/22* | (2006.01) | |
| *C07D 409/04* | (2006.01) | |
| *H01L 51/00* | (2006.01) | |
| *C09B 57/00* | (2006.01) | |
| *C09B 23/04* | (2006.01) | |
| *C07D 333/22* | (2006.01) | |

(52) U.S. Cl.
CPC ........ *H01L 51/0059* (2013.01); *C07C 225/22* (2013.01); *C07D 333/22* (2013.01); *C07D 409/04* (2013.01); *C09B 23/04* (2013.01); *C09B 57/007* (2013.01); *C09B 57/008* (2013.01); *H01L 51/0061* (2013.01); *H01L 51/0064* (2013.01); *H01L 51/0068* (2013.01); *H01L 51/0072* (2013.01); *C07C 2601/04* (2017.05); *Y02E 10/549* (2013.01)

(58) Field of Classification Search
CPC .. C07D 403/04; C07D 209/18; C07D 209/12; C07D 403/14; C07D 405/14; C07D 409/04; C07C 35/045; C07C 225/22; C07C 2601/04; H01L 51/0059; H01L 51/0061; H01L 51/0068; H01L 51/0072

USPC ............ 548/466, 469; 564/307; 549/59, 43; 544/326
See application file for complete search history.

(56) References Cited

U.S. PATENT DOCUMENTS

2011/0288300 A1    11/2011   Wu et al.

FOREIGN PATENT DOCUMENTS

| CN | 102356509 A | 2/2012 | |
|---|---|---|---|
| DE | WO 2010049042 A2 * | 5/2010 | ............. C09B 47/08 |
| EP | 1 017 070 A2 | 7/2000 | |
| EP | 2 278 636 A1 | 1/2011 | |
| JP | 2008-134282 A | 6/2008 | |
| JP | 2012084503 A * | 4/2012 | |

OTHER PUBLICATIONS

International Search Report issued Dec. 20, 2013 in PCT/EP2013/001031.
Jheng-Ying Li, et al., "Unsymmetrical Squaraines Incorporating the Thiophene Unit for Panchromatic Dye-Sensitized Solar Cells" Organic Letters, vol. 12, No. 23, XP 55064773 A, 2010, pp. 5454-5457.
R. Cohen, et al., "Molecular Control over Semiconductor Surface Electronic Properties: Dicarboxylic Acids on CdTe, CdSe, GaAs, and InP" J. Am. Chem. Soc., vol. 121, No. 45, 1999, pp. 10545-10553.
Adi Salomon, et al., "Molecular modification of an ionic semiconductor-metal interface: ZnO/molecule/Au diodes" Applied Physics Letters, vol. 82, No. 7, 2003, 5 Pages.
Dori Gal, et al., "Engineering the interface energetics of solar cells by grafting molecular properties onto semiconductors" Proc. Indian Acad. Sci.(Chem. Sci.), vol. 109, No. 6, Dec. 1997, pp. 487-496.
Iris Visoly-Fisher, et al., "Molecular Adsorption-Mediated Control over the Electrical Characteristics of Polycrystalline CdTe/CdS Solar Cells" ChemPhysChem, vol. 6, 2005, pp. 277-285.
Ayelet Vilan, et al., "Molecular control over Au/GaAs diodes" Letters to Nature, vol. 404, 2000, pp. 166-168.
Ayelet Vilan, et al., "Molecule-Metal Polarization at Rectifying GaAs Interfaces" J. Phys. Chem. B, vol. 107, 2003, pp. 6360-6376.

(Continued)

*Primary Examiner* — Matthew Coughlin
*Assistant Examiner* — Sagar Patel
(74) *Attorney, Agent, or Firm* — Oblon, McClelland, Maier & Neustadt, L.L.P.

(57) ABSTRACT

A compound containing a squaric acid or a croconic acid group as an anchoring group. The compound containing a squaric acid or a croconic acid group has formula 1:

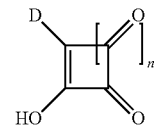

where n is 1 or 2, and D is selected from an alkyl, aryl, aralkyl, heteroalkyl, heteroaryl or heteroaralkyl substituent, and each substituent is substituted or unsubstituted.

9 Claims, 8 Drawing Sheets

(56) References Cited

OTHER PUBLICATIONS

Yoram Selzer, et al., "Fine Tuning of Au/SiO$_2$/Si Diodes by Varying Interfacial Dipoles Using Molecular Monolayers" Advanced Materials, vol. 13, No. 7, Apr. 2001, pp. 508-511.

Hitoshi Kusama, et al., "Influence of pyrimidine additives in electrolytic solution on dye-sensitized solar cell performance" Journal of Photochemistry and Photobiology A: Chemistry, vol. 160, 2003, pp. 171-179.

Jianjun He, et al., "Modified Phthalocyanines for Efficient Near-IR Sensitization of Nanostructured TiO$_2$ Electrode" J. Am. Chem. Soc., vol. 124, 2002, pp. 4922-4932.

Mohammad K. Nazeeruddin, et al., "Engineering of Efficient Panchromatic Sensitizers for Nanocrystalline TiO$_2$-Based Solar Cells" J. Am. Chem. Soc., vol. 123, 2001, pp. 1613-1624.

M. K. Nazeeruddin, et al., "Conversion-of Light to Electricity by cis-X$_2$Bis(2,2'-bipyridyl-4,4'-dicarboxylate)ruthenium(II) Charge-Transfer Sensitizers (X = Cl$^-$, Br$^-$, I$^-$, CN$^-$, and SCN$^-$) on Nanocrystalline TiO$_2$ Electrodes" J. Am. Chem. Soc., vol. 115, 1993, pp. 6382-6390.

Christophe J. Barbé, et al., "Nanocrystalline Titanium Oxide Electrodes for Photovoltaic Applications" Journal of the American Ceramic Society, vol. 80, No. 12, 1997, pp. 3157-3171.

Hitoshi Kusama, et al., "Influence of alkylpyridine additives in electrolyte solution on the performance of dye-sensitized solar cell" Solar Energy Materials & Solar Cells, vol. 80, 2003, pp. 167-179.

Xiyou Li, et al., "New peripherally-substituted naphthalocyanines: synthesis, characterisation and evaluation in dye-sensitised photoelectrochemical solar cells" New J. Chem., vol. 26, 2002, pp. 1076-1080.

S. Y. Huang, et al., "Charge Recombination in Dye-Sensitized Nanocrystalline TiO$_2$ Solar Cells" J. Phys. Chem. B, vol. 101, No. 14, 1997, pp. 2576-2582.

Sven Ruhle, et al., "Molecular Adjustment of the Electronic Properties of Nanoporous Electrodes in Dye-Sensitized Solar Cells" J. Phys. Chem. B, vol. 109, No. 40, 2005, pp. 18907-18913.

S. Sakaguchi, et al., "Quasi-solid dye sensitized solar cells solidified with chemically cross-linked gelators: Control of TiO$_2$/gel electrolytes and counter Pt/gel electrolytes interfaces" Journal of Photochemistry and Photobiology A: Chemistry, vol. 164, 2004, 7 pages.

Andreas Kay, et al., "Artificial Photosynthesis. 1. Photosensitization of TiO$_2$ Solar Cells with Chlorophyll Derivatives and Related Natural Porphyrins" J. Phys. Chem., vol. 97, No. 23, 1993, pp. 6272-6277.

Fabrice Odobel, et al., "Porphyrin dyes for TiO2 sensitization" Journal of Materials Chemistry, vol. 13, 2003, pp. 502-510.

Md. K. Nazeeruddin, et al., "Efficient near IR sensitization of nanocrystalline TiO$_2$ films by ruthenium phthalocyanines" Chemical Communications, vol. 6, 1998, 3 pages.

Christophe Bauer, et al., "Interfacial Electron-Transfer Dynamics in Ru(tcterpy)(NCS)$_3$-Sensitized TiO$_2$ Nanocrystalline Solar Cells" J. Phys. Chem. B, vol. 106, No. 49, 2002, pp. 12693-12704.

Kohjiro Hara, et al., "Dye-Sensitized Nanocrystalline TiO$_2$ Solar Cells Based on Ruthenium(II) Phenanthroline Complex Photosensitizers" Langmuir, vol. 17, No. 19, 2001, pp. 5992-5999.

Peng Wang, et al., "Enhance the Performance of Dye-Sensitized Solar Cells by Co-grafting Amphiphilic Sensitizer and Hexadecylmalonic Acid on TiO$_2$ Nanocrystals" J. Phys. Chem. B, vol. 107, No. 51, 2003, pp. 14336-14341.

Jessica Krüger, et al., "Modification of TiO$_2$ Heterojunctions with Benzoic Acid Derivatives in Hybrid Molecular Solid-State Devices" Advanced Materials, vol. 12, No. 6, 2000, pp. 447-451.

Shohei Sakaguchi, et al., "Probing TiO$_2$/Dye Interface in Dye Sensitized Solar Cells Using Surface Potential Measurement" Applied Physics Express, vol. 1, 2008, 3 pages.

Shyam S. Pandey, et al., "Investigating the Role of Dye Dipole on Open Circuit Voltage in Solid-State Dye-Sensitized Solar Cells" Japanese Journal of Applied Physics, vol. 50, 2011, 4 pages.

Do Hwan Kim, et al., "Enhancement of Field-Effect Mobility Due to Surface-Mediated Molecular Ordering in Regioregular Polythiophene Thin Film Transistors" Advanced Functional Materials, vol. 15, No. 1, 2005, pp. 77-82.

M. Yoshida, et al., "Surface Potential Control of an Insulator Layer for the High Performance Organic FET" Synthetic Metals, vol. 137, 2003, pp. 967-968.

Xavier Bulliard, et al., "Enhanced Performance in Polymer Solar Cells by Surface Energy Control" Advanced Functional Materials, vol. 20, 2010, pp. 4381-4387.

Amalie Dualeh, et al., "Influence of Donor Groups of Organic D-π-A Dyes on Open-Circuit Voltage in Solid-State Dye-Sensitized Solar Cells" The Journal of Physical Chemistry C, vol. 116, 2012, pp. 1572-1578.

Shenyuan Yang, et al., "Tuning Semiconductor Band Edge Energies for Solar Photocatalysis via Surface Ligand Passivation" Nano Letters, vol. 12, 2012, pp. 383-388.

Shyam S. Pandey, et al., "Substituent effect in direct ring functionalized squaraine dyes on near infra-red sensitization of nanocrystalline TiO$_2$ for molecular photovoltaics" Journal of Photochemistry and Photobiology A: Chemistry, vol. 214, 2010, pp. 269-275.

Combined Office Action and Search Report issued Sep. 28, 2015 in Chinese Patent Application No. 201380024368.5 (with English translation of Category of Cited Documents).

* cited by examiner

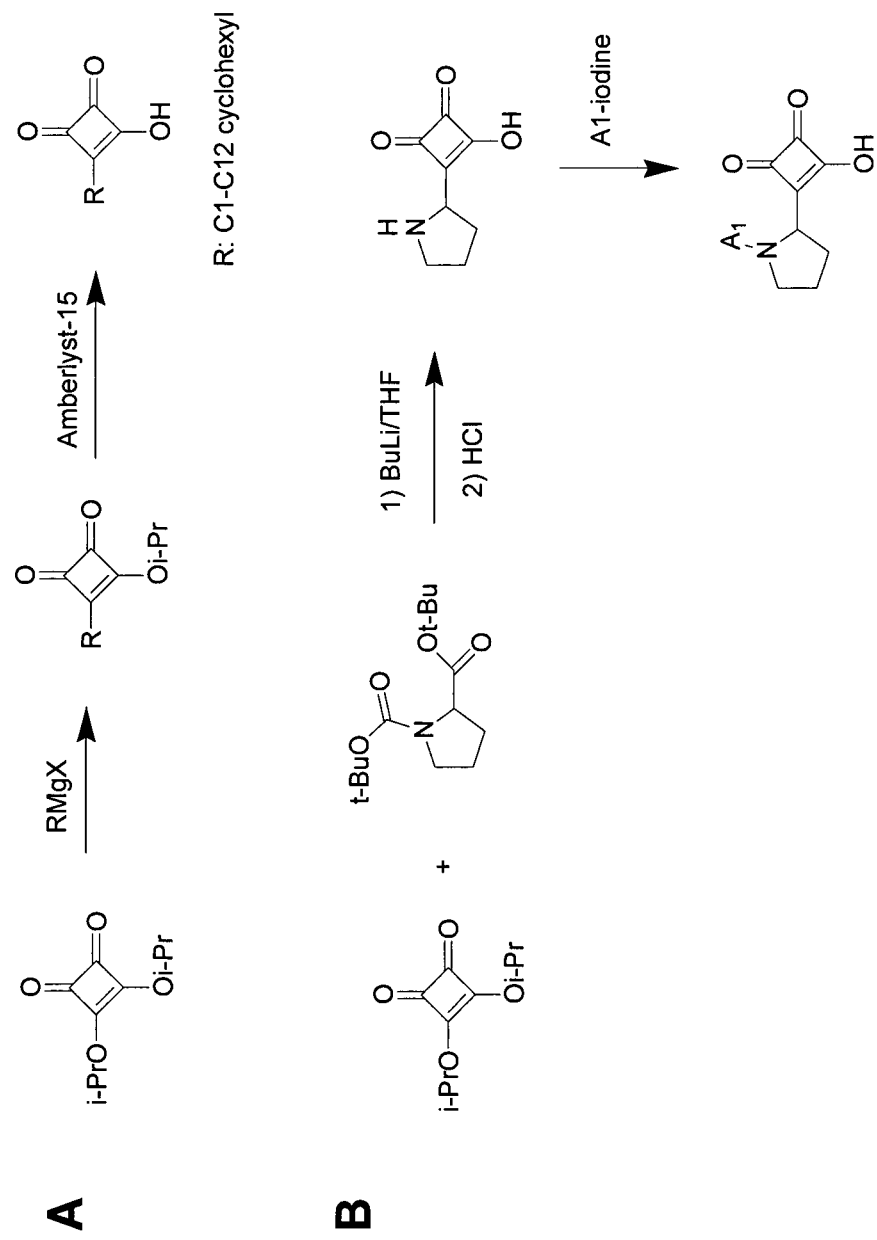
Figure 1 A and B

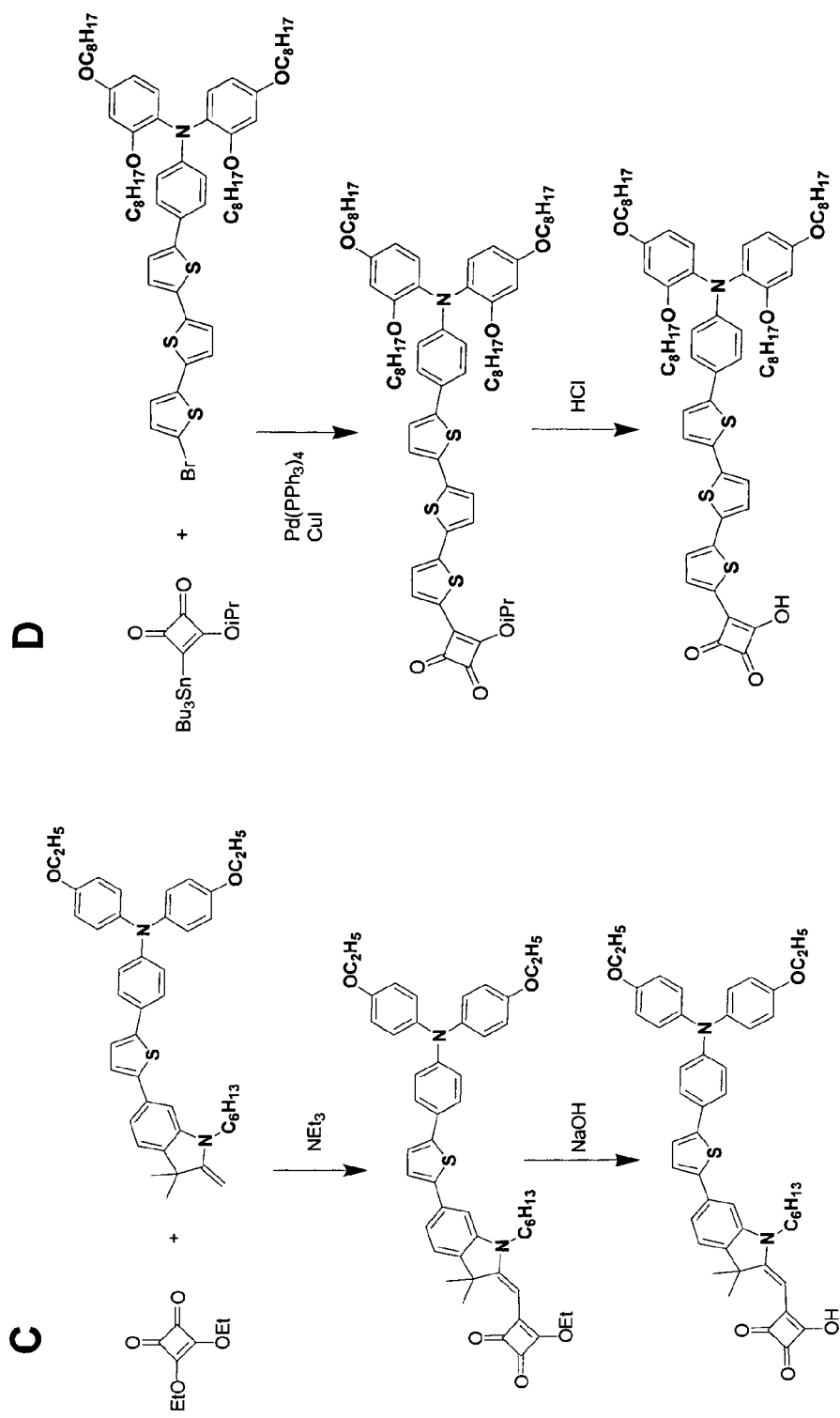
Figure 1 C and D $$\Delta\phi_{comp} = \frac{N \vec{\mu}_N}{\varepsilon \varepsilon_0}$$

N = number of adsorbed molecules / surface area
$\varepsilon$ = permittivity of dipole layer
$\varepsilon_0$ = permittivity of vacuum

ORGANIC COMPOUNDS CONTAINING SQUARIC ACID OR CROCONIC ACID MOIETIES FOR APPLICATION IN ELECTRONIC DEVICES

The present disclosure relates to compounds comprising a squaric acid or croconic acid group as anchoring group, to methods of synthesis of said compounds, to the use of said compounds, and to assemblies for use in an electronic device, said assemblies comprising a surface to which least one such compound is attached via a squaric acid or croconic acid group. The present disclosure also relates to an electronic device including such assembly.

Charge (hole or electron) transport at the interface between dissimilar materials, i.e. inorganic/inorganic, organic/organic, or inorganic/organic, is involved in a variety of electronic devices, including light-emitting devices (LEDs, etc.), transistor devices (FETs, TFTs, etc.), and photovoltaic devices (solar cells, photodetectors, etc.). So for example, a Schottky barrier is present at the electrode/organic interface due to different energy level alignments of the work function of the electrode material and the highest occupied molecular orbital (HOMO) and/or the lowest unoccupied molecular orbital (LUMO) of the organic material. Hence, the Schottky barrier represents the barrier for charge injection between the two phases and its magnitude is an important factor in determining the performance, efficiency, and lifetime of virtually all organic electronic devices.

Interfaces between dissimilar materials, i.e. inorganic/inorganic, organic/organic, or inorganic/organic, are inherent to most electronic, and electrochemical devices. In such devices the device performance, efficiency and lifetime, depend critically on the properties of the components and interfaces between the different components, such as their energy levels alignment, but also their adhesion or coverage determined by their surface energy or morphology of the materials.

One of the strategies to improve performance of such devices is directed toward the use of molecular adsorbants deposited on the surface of one component or even both components. In the prior art so far, different kinds of molecules are used as molecular adsorbents, depending on whether the component is a conductor, a semiconductor, or an insulator. Typically, thiols and amines are used for metals, and oxy-acid compounds (or activated derivatives thereof) are used for metal-oxide-based or metal-chalcogenide-based semiconductors or insulators.

The presence of an adsorbant on a surface component can have significant effects on one or both of the components that are related to, for example:
1) a relative shift in vacuum energy level (i.e. a change in work function) or
2) a change in tunnelling barrier, both of which affect the barriers for charge transport between the components, or
3) a change in surface free energy, which affects wetting behaviour and/or adhesive forces between the components, and/or
4) a change in light absorption capability of the component to which it is attached.

Organic molecules with different dipole moments, adsorbed to the surface of semiconductors, can modify the electronic properties such as band bending, electron affinity and work function of the semiconductor (1). This has been used to modify the I-V characteristics of ZnO/Au Schottky junctions (2), CdS/CdTe solar cells (3, 4) and other solid-state systems (5-7).

Similar kind of surface modification has then been also applied to electrochemical systems such as DSSCs with nanoporous $TiO_2$ and an electrolyte interface. Overall photoconversion efficiency of a DSSC is basically determined by the short-circuit current density (Jsc), open circuit voltage (Voc), and fill factor. Voc playing an important role in determining the photoconversion efficiency is defined by the difference in the quasi-Fermi level of $TiO_2$ and redox of the electrolyte DSSC.

In the prior art, a way to control the $TiO_2$ energy levels is the adsorption of organic molecules with different dipole moments, together with the photosensitizer dye molecules. Several kinds of adsorbents (sometimes also called coadsorbent, additives) have been found to improve the photovoltaic performance of DSSCs. For example, nitrogen containing heterocyclic additives (8), such as 4-tert-butylpyridine, have been used as additives in organic electrolytes (9-13), or in dye coating solutions (14), or as reagents for treating the dye-coated $TiO_2$ electrode (15). This pyridine derivative remarkably improves the photovoltage of the solar cell, and the improvement is attributable to suppression of the dark current.

Another strategy was the molecular modification of $TiO_2$ surface by dipolar carboxylic acid derivatives (16, 17). For example, Kay and Grätzel found that when they employed cholic acid derivatives as coadsorbates to porphyirins photosensitizers, both the photocurrent and the photovoltage of the solar cells were improved (18). Such cholic acid derivatives have been used in DSSCs based on porphyrins (19), phthalocyanines (20, 21), naphthalocyanines (22), ruthenium terpyridine (the black dye) (23, 24), and a Ru phenanthroline complex (25) to improve solar cell performance.

Wang et al. reported that using hexadecylmalonic acid (HDMA) as a coadsorbate for a DSSC based on a Ru bipyridyl complex (Z907 dye) improved both the photocurrent and photovoltage of the cell (26). The improved photocurrent due to coadsorbates can be attributed to a positive shift of the conduction band edge of $TiO_2$ in the presence of acid or to suppression of quenching processes due to energy transfer; both of these effects result in increases in electron-injection yields. The improved photovoltage is believed to be caused by suppression of recombination between the injected electrons and $I^-$ ions which are in the electrolyte.

It was furthermore reported that also the relative energetics at an organic/inorganic heterojunction, comprised of a compact $TiO_2$ layer (n-type) and an organic p-type semiconductor compound (spiro-OMeTAD), could be modified by an organic adsorbent forming an additional dipole layer on the TiO2 surface (27).

In photoelectrochemical cells the photosensitization and electron transfer across the semiconductor solution interface plays a vital role. In these systems wide band gap semiconductors, such as $TiO_2$, ZnO, $SnO_2$ are used. Due to their wide-band gap, generally over >3 eV, these materials are not capable of broadband solar photon absorption. To extend their light absorption capabilities, so as to improve the performance of the devices by making use of a broader range of solar photons, molecular adsobents are used, so called photosensitizers or sensitizer dyes. Thus, a main component of a dye-sensitized solar cell for example, is a nanocrystalline wide band-gap oxide semiconductor electrode on which surface a photosensitizer is adsorbed. The photosensitizer forming a layer on the surface will influence not only the optical properties of the semiconductor, but also other physical properties such as component work function or surface energy.

Hayase investigated for example the effect of the photosensitizer dipole moment on the shift of the TiO$_2$ workfunction and therefore on the Voc in a DSCC (28, 29). As prior art for attachment onto metal-oxides oxy-acid anchoring group, carboxylic acid, were used.

It was an object of the present disclosure to provide for means to effect the physical and/or photophysical properties of the surface of conducting, semiconducting, or insulating substrates. It was also an object of the present disclosure to provide for means to effect the physical and/or photophysical properties of such substrates with molecules that can be easily prepared.

It was also an object of the present disclosure to provide for means to effect more than one desired physical and/or photophysical properties of such substrates.

All these objects are solved by a compound comprising a squaric acid or croconic acid group as anchoring group, said compound having general formula 1

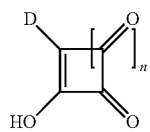

formula 1 wherein n is 1 or 2, and
D is selected from an alkyl, aryl, aralkyl, heteroalkyl, heteroaryl or heteroaralkyl substituent, each substituent being substituted or unsubstituted.

A compound comprising a squaric acid or croconic acid group as anchoring group according to the present disclosure can also be represented by formula 1a (with a squaric acid anchoring group) or formula 1b (which a croconic acid anchoring group)

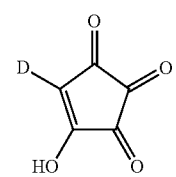

formula 1a

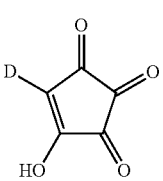

formula 1b

In one embodiment, said compound is selected from any one of formulas 2 to 12:

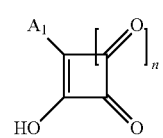

formula 2

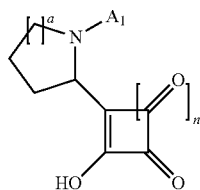

formula 3

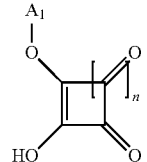

formula 4

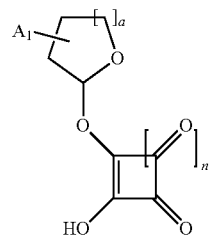

formula 5

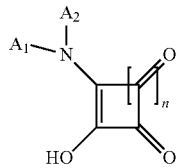

formula 6

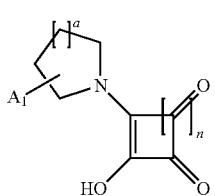

formula 7

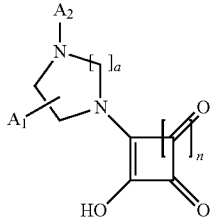

formula 8

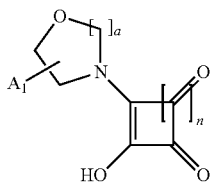

formula 9

-continued formula 10
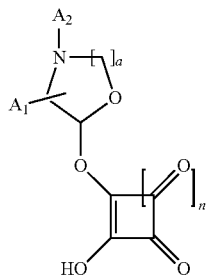

formula 11
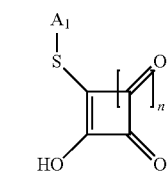

formula 12
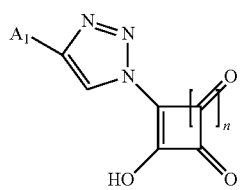

wherein
a=0-2,
$A_1$ and $A_2$ each independently is selected from H, or any cyclic or acyclic substituted, or non-substituted alkyl, or heteroalkyl, or any straight or branched chain moiety of general formula $-[(CXY)_{n1}-(B_1)_{n3}-(B_2)_{n2}-W]_p-R$, wherein, at each occurrence and independently, p=0-18, preferably 0-3, n1 and n2 are independently=0-18, preferably 0-4, n3=0-1,
wherein W is selected from —O—, —S—, —N(R)—, —C(R)=N—, —C(O)N(R)—, —Si(R)$_2$—, —OC(O)—, —C(O)O—, —C(O)—, —S(O)$_2$—, —N(R)C(O)—, and —N(R)S(O)$_2$—,
wherein X, Y, R each independently is selected from H or any straight or branched alkyl chain of general formula —C$_n$H$_{2n+1}$, or ester, carboxylic acid —COOR$^1$, alkoxy —OR$^1$, thiol —SR$^1$, amine —NR$^1_2$, nitro —NO$_2$, cyano —CN, -isothiocyanato —SCN, -trifluoromethyl —CF$_3$, or halogen F, Cl, Br, I, or substituted or unsubstituted aryl or heteroaryl, or ester, carboxylic acid, alkoxy, thiol, amine, nitro, cyano functionalized or halogenated straight or branched alkyl, wherein R$^1$ is H or any alkyl or aryl or heteroaryl, and n=0-18.
Wherein $B_1$ is selected from the moieties shown in formula 13 formula 13
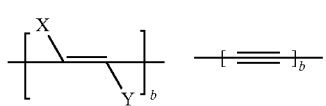 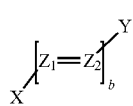

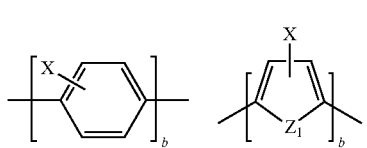

-continued

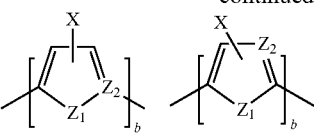

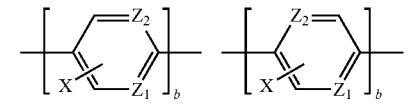

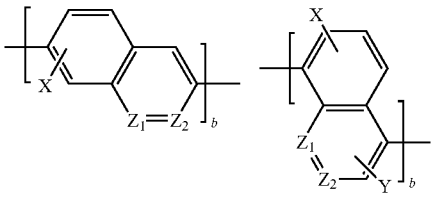

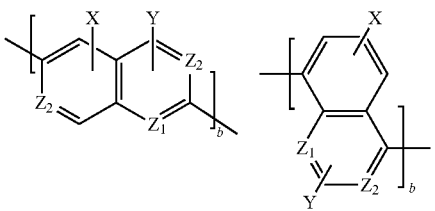

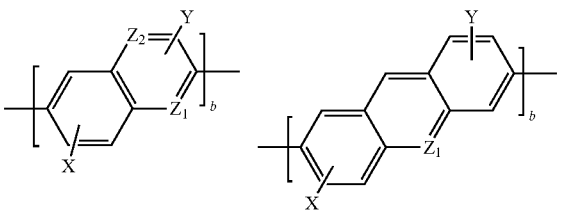

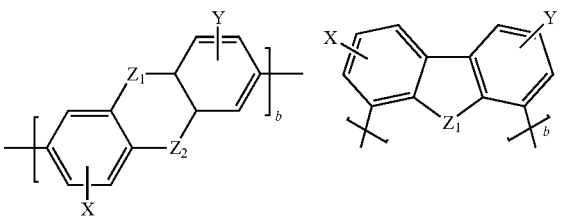

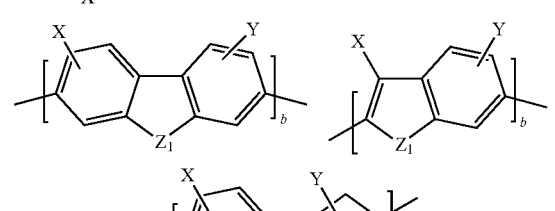

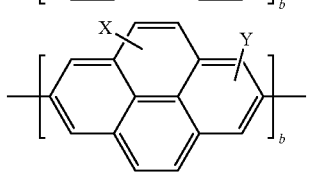

-continued

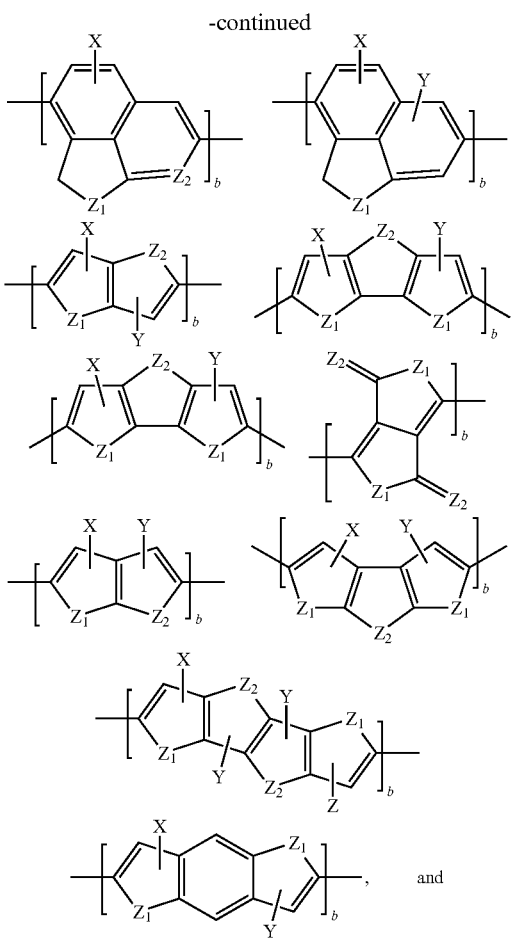

$B_2$ is —$C_6H_4$— or CXY, and
wherein $Z_1$ and $Z_2$ each independently is selected from $C(R)_{m1}$, S, O, S, $Si(R)_{m2}$, $N(R)_{m3}$,
wherein m1 and m3 are independently=0-2, m2=1 or 2, and b=1-5, preferably 1-3,
wherein X, Y and R are as defined above.

In one embodiment, the squaric acid or croconic acid group of a compound according to the present disclosure has a dipole moment with a first polarity, and D is a substituent with at least one or several uncharged or charged polar components that has a second polarity which is opposite said first polarity.

In this embodiment, D is preferably an electron-donating group,
wherein preferably
$A_1$ and $A_2$ each independently is selected from H, or any cyclic or acyclic substituted or non-substituted alkyl, or heteroalkyl, or any straight or branched chain moiety of general formula —$[(CXY)_{n1}$—$(B_1)_{n3}$—$(B_2)_{n2}$—$W]_p$—R,
wherein, at each occurrence and independently, p=0-18, preferably 0-3,
n1 and n2 are independently=0-18, preferably 0-4, n3=0-1,
wherein W is selected from —O—, —S—, —N(R)—, —C(R)=N, —C(O)N(R), —$Si(R)_2$,
wherein X, Y, R each independently is selected from H or any straight or branched alkyl chain of general formula —$C_nH_{2n+1}$, or ester, carboxylic acid —$COOR^1$, alkoxy —$OR^1$, thiol —$SR^1$, amine —$NR^1{}_2$, nitro —$NO_2$, cyano —CN, -isothiocyanato —SCN, -trifluoromethyl —$CF_3$, or halogen F, Cl, Br, I, or substituted or unsubstituted aryl or heteroaryl, or ester, carboxylic acid, alkoxy, thiol, amine, nitro, cyano functionalized or halogenated straight or branched alkyl, wherein $R^1$ is H or any alkyl or aryl or heteroaryl and n=0-18,
wherein $B_1$ is selected from the moieties shown in formula 13 as defined above and
$B_2$ is —$C_6H_4$— or CXY.

In this embodiment, $A_1$ and/or $A_2$ comprises $A_1$ and/or $A_2$ comprises alkoxy, amine or thiole groups in its structure.

In this embodiment, $A_1$ and $A_2$ each independently is selected from

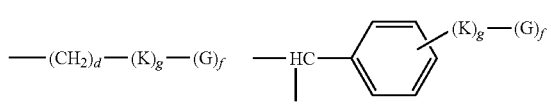

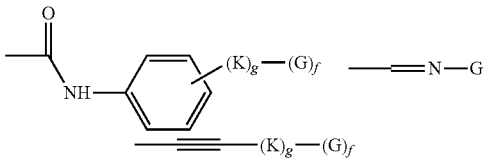

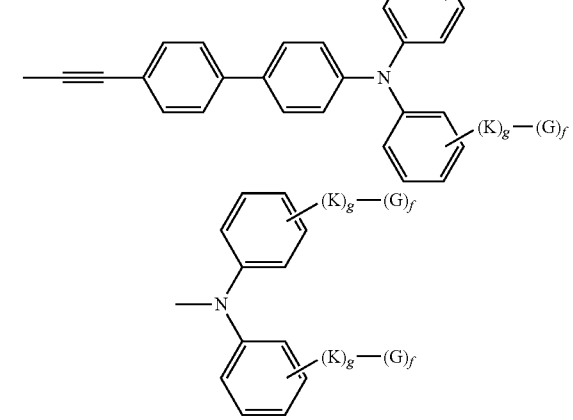

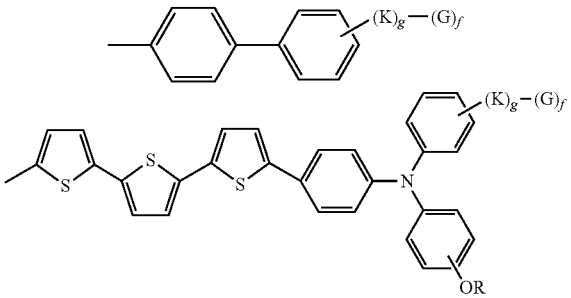

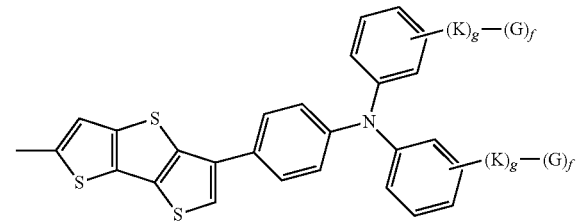

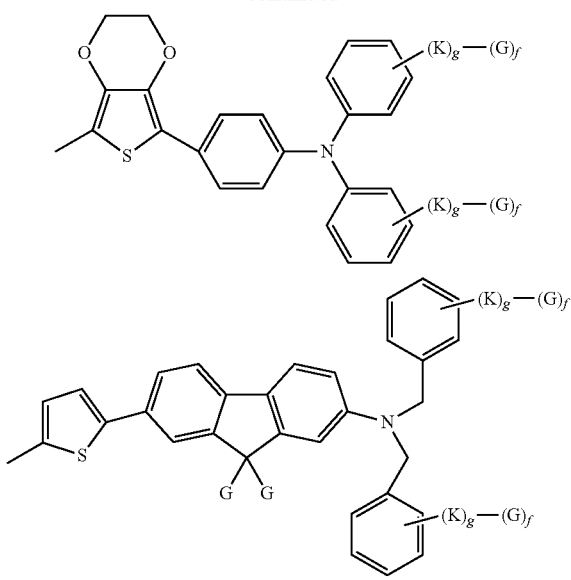

wherein, at each occurrence and independently, d=0-6, preferably 0-2,

G being any cyclic or acyclic substituted, or straight or branched alkyl, f=1, 2, K being selected from O, S, N, g=0, 1, wherein the alkyl, alkoxy, amine, thiole group —$(K)_g$-$(G)_f$ can be one or more attached to the aryl and heteroaryl rings, in o-, m-, p-position, preferably in o- and/or p-position.

In this embodiment, $A_1$ and $A_2$ each independently can preferably be selected from

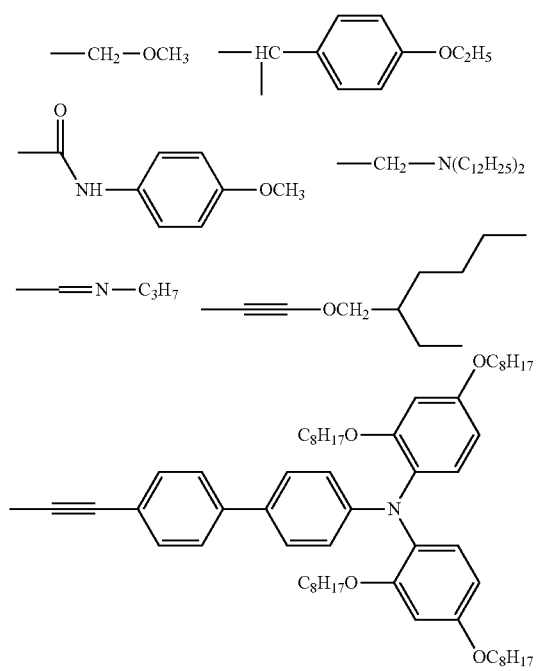

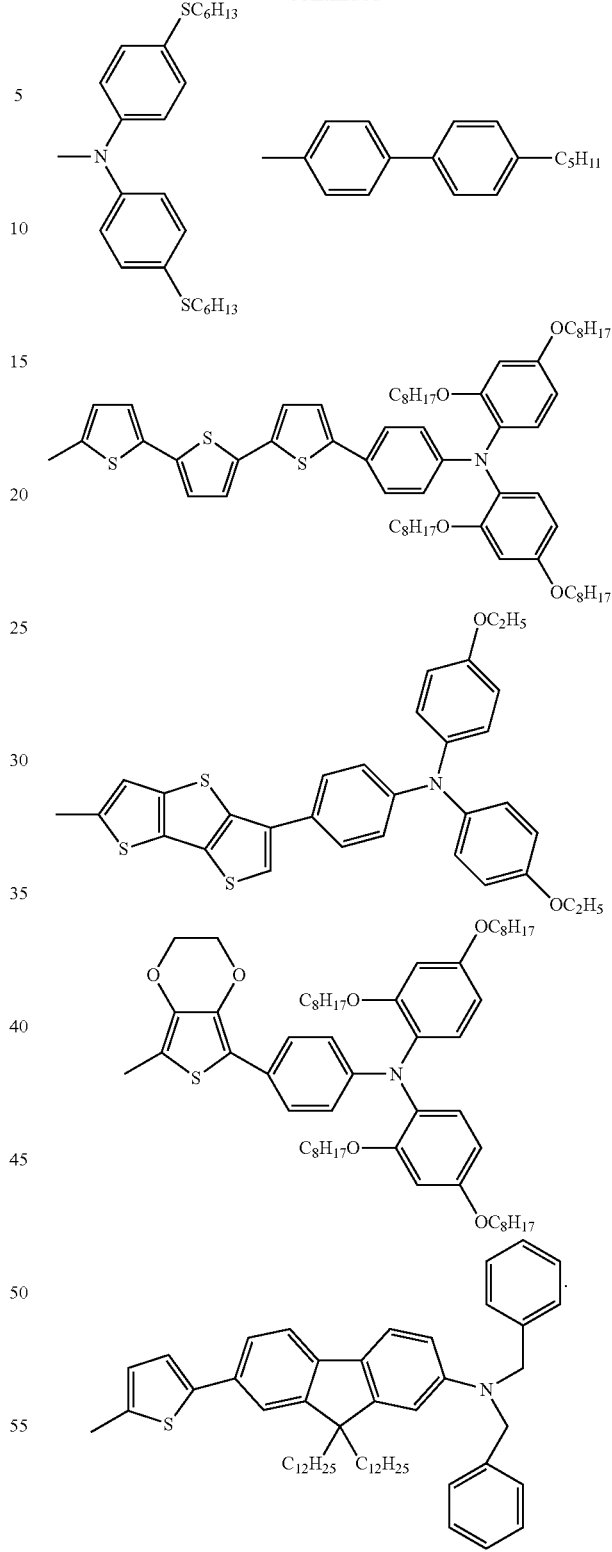

In one embodiment, the squaric acid or croconic acid group of a compound according to the present disclosure has a dipole moment with a first polarity, and D is a substituent with at least one or several uncharged or charged polar components that has a second polarity which is the same as said first polarity.

In this embodiment, D is preferably an electron-accepting group,
wherein preferably
$A_1$ and $A_2$ each independently is selected from H, or any cyclic or acyclic substituted, or non-substituted alkyl, or heteroalkyl, or any straight or branched chain moiety of general formula —[(CXY)$_{n1}$—(B$_1$)$_{n3}$—(B$_2$)$_{n2}$—W]$_p$—R, wherein, at each occurrence and independently, p=0-18, preferably 0-3,
n1 and n2 are independently=0-18, preferably 0-4, n3=0-1,
wherein W is selected from —OC(O), —C(O)O, —C(O), —S(O)$_2$, —N(R)C(O), and —N(R)S(O)$_2$,
wherein X, Y, R each independently is selected from H or any straight or branched alkyl chain of general formula —C$_n$H$_{2n+1}$, or ester, carboxylic acid —COOR$^1$, alkoxy —OR$^1$, thiol —SR$^1$, amine —NR$^1{}_2$, nitro —NO$_2$, cyano —CN, -isothiocyanato —SCN, -trifluoromethyl —CF$_3$, or halogen F, Cl, Br, I, or substituted or unsubstituted aryl or heteroaryl, or ester, carboxylic acid, alkoxy, thiol, amine, nitro, cyano functionalized or halogenated straight or branched alkyl, wherein R$^1$ is H or any alkyl or aryl or hetero aryl and n=0-18,
wherein B$_1$ is selected from the moieties shown in formula 13 as defined above and
B$_2$ is —C$_6$H$_4$— or CXY.

In this embodiment, wherein $A_1$ and/or $A_2$ comprises fluorinated alkyl or fluorinated phenyl groups, nitro, cyano or triazine, pyrazine, pyrimidine or pyridine.

In this embodiment, $A_1$ and $A_2$ each independently can be selected from

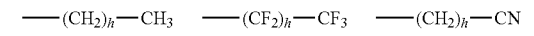
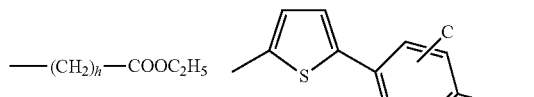
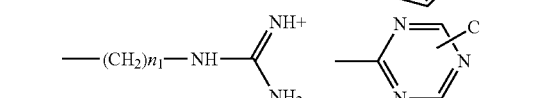
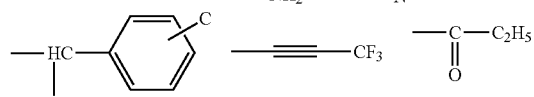
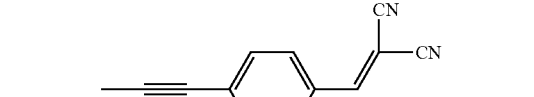
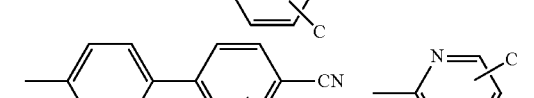
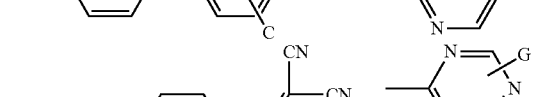
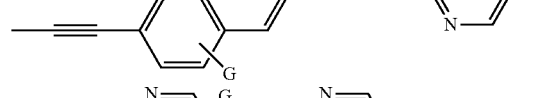
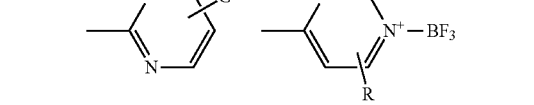

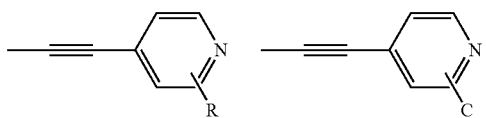

wherein, at each occurrence and independently,
G being any cyclic or acyclic substituted, or straight or branched alkyl,
C=—F, —CF$_3$, —CN, —NO2, —C(CF$_3$)$_3$,
h=0-18, preferably 0-8,
wherein G, C, each independently being one or more attached to the aryl and heteroaryl rings, in o-, m-, p-position, preferably in o- and/or p-position.

In this embodiment, $A_1$ and $A_2$ each independently can preferably be selected from

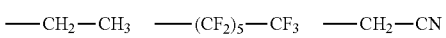
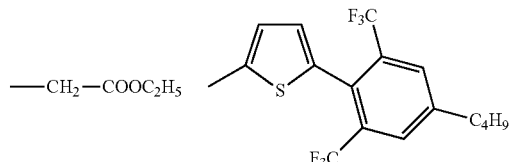
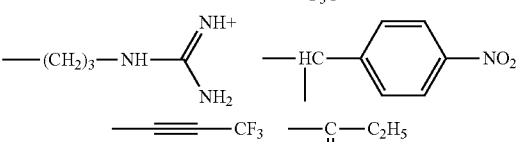
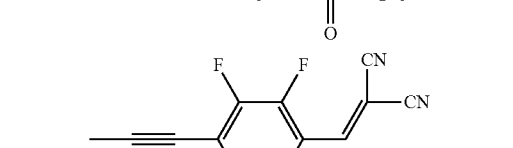
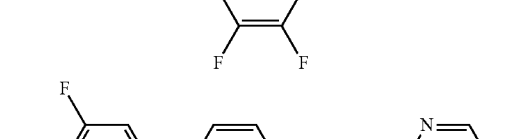
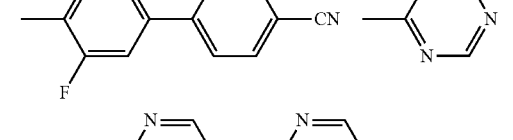
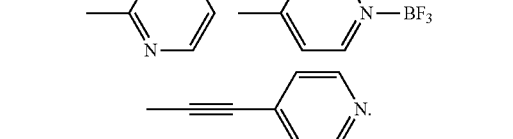

In one embodiment, $A_1$ and/or $A_2$ comprises in its structure a hydrophilic functional group, preferably a hydroxy (OH), thiol (SH), unsubstituted amine (NH$_2$), carboxylic acid (COOH), cyano (CN), nitro (NO$_2$), keton (CO), ester (COOR), iodide (I), bromide (Br), preferably as end-group or peripheral group.

In this embodiment, $A_1$ and $A_2$ each independently can be selected from

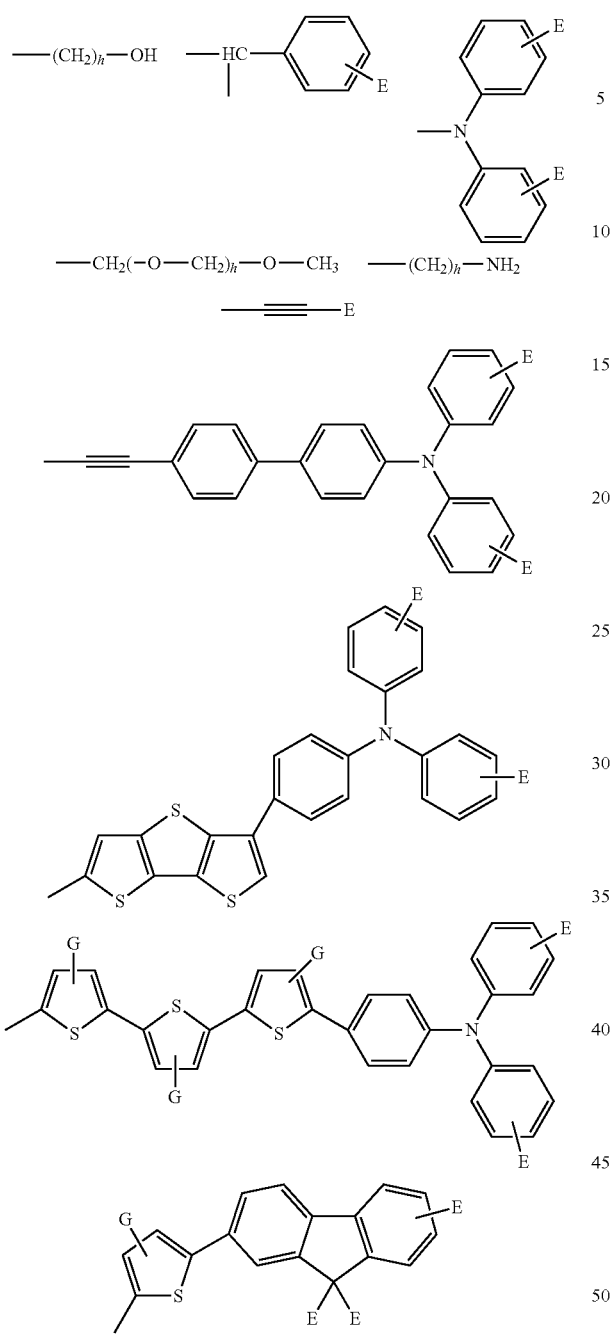
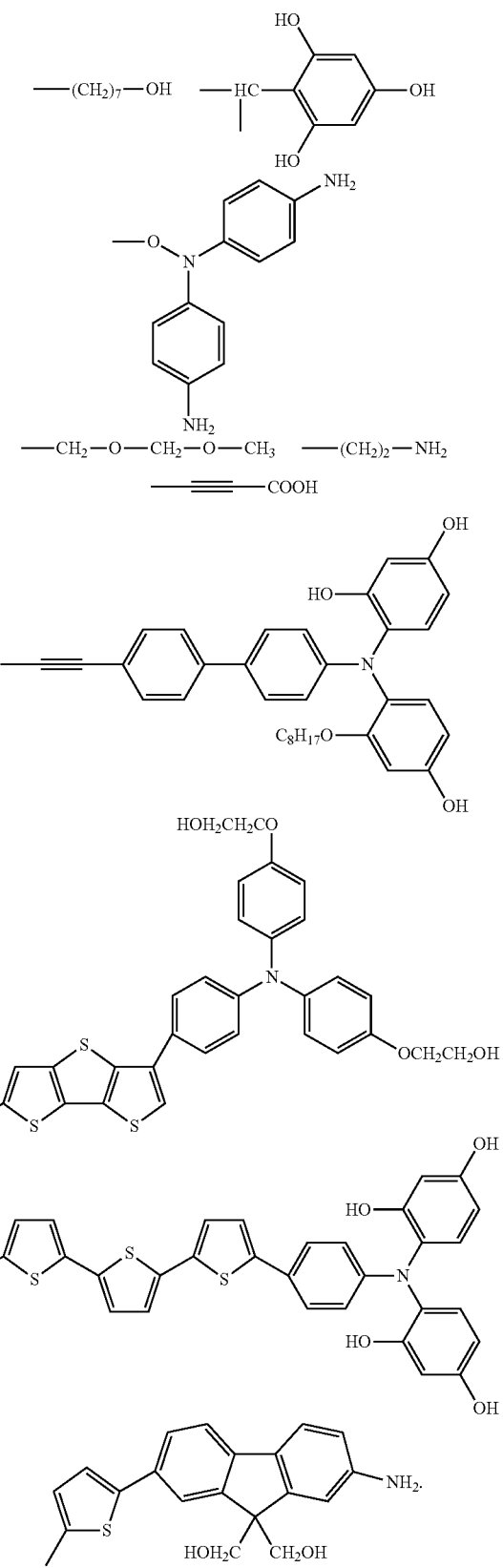

wherein, at each occurrence and independently,

E=—$(CH_2)_h$—OH, —$(CH_2)_h$—$NH_2$, —$(CH_2)_h$—COOH, —$(CH_2)_h$—CN, —(O—$CH_2)_h$—OH, —$(CH_2)_h$—SH, —$(CH_2)_h$—$NO_2$, —$(CH_2)_h$—CO, —$(CH_2)_h$—OHCOOR, —$(CH_2)_h$—I, —$(CH_2)_h$—Br, h=0-18, preferably 0-4, G being H or any cyclic or acyclic substituted, or straight or branched alkyl, E being one or more attached to the aryl rings, in o-, m-, p-position.

In this embodiment, $A_1$ and $A_2$ each independently can preferably be selected from In one embodiment, $A_1$ and/or $A_2$ comprises in its structure cyclic or acyclic, straight or branched non-substituted alkyl or aryl, or comprises in its structure alkyl substituted aryl or heteroaryl, or alkyl functionalized amine, or alkoxyl or thiole, preferably as end-group or peripheral group.

In this embodiment, $A_1$ and $A_2$ each independently can be selected from

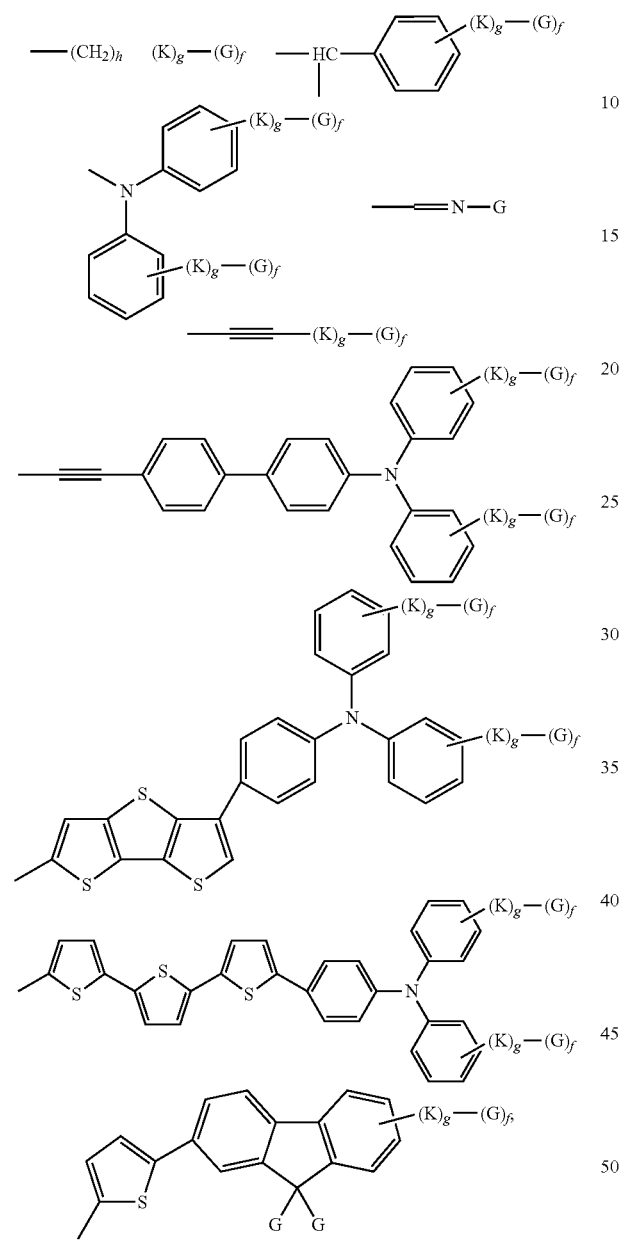

wherein, at each occurrence and independently,
G=cyclic or acyclic, straight or branched substituted or non-substituted alkyl, preferably longer than hexyl ($C_6$),
h=0-18, preferably 0-2,
f=1, 2,
K being selected from O, S, N,
g=0, 1,
wherein the alkyl, alkoxy, amine, thiole group —$(K)_g$-$(G)_f$ can be one or more attached to the aryl and heteroaryl rings, in o-, m-, p-position, preferably in o- and/or p-position.

In this embodiment, $A_1$ and $A_2$ each independently can preferably be selected from

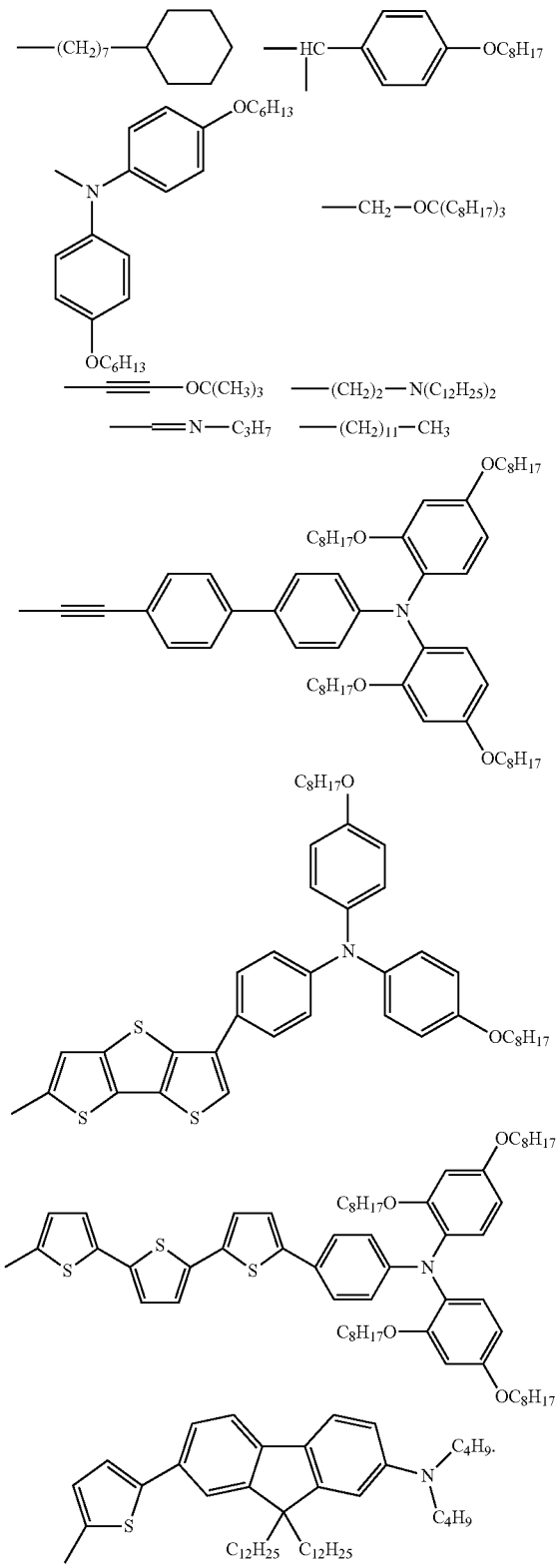

In one embodiment, D is attached to the squaric acid or croconic acid group/moiety of a compound of the present disclosure such that a non-conjugated system is formed.

In this embodiment, $A_1$ and/or $A_2$ comprises in its structure cyclic or acyclic, straight or branched non-substituted alkyl or aryl, or comprises in its structure alkyl substituted aryl or heteroaryl, or alkyl functionalized amine, or alkoxyl, or thiole, preferably as end-group or peripheral group.

In this embodiment, $A_1$ and $A_2$ each independently can be selected from

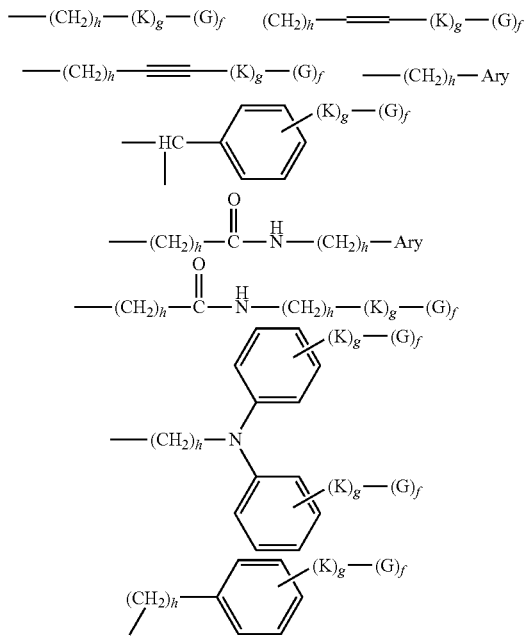

wherein, at each occurrence and independently,
G=cyclic or acyclic, straight or branched substituted or non-substituted alkyl, preferably longer than hexyl ($C_6$),
h=0-18, preferably 2-12,
f=1, 2,
K being selected from O, S, N,
g=0, 1,
wherein G being one or more attached to the aryl rings, in o-, m-, p-position,
wherein the alkyl, alkoxy, amine, thiole group $—(K)_g-(G)_f$ can be one or more attached to the aryl and heteroaryl rings, in o-, m-, p-position, preferably in o- and/or p-position.

In this embodiment, $A_1$ and $A_2$ each independently can preferably be selected from

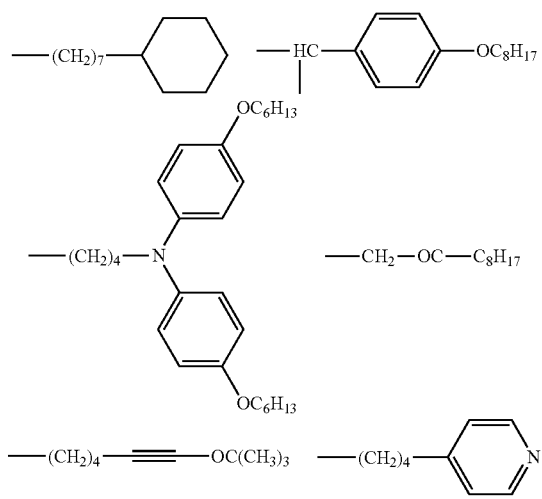

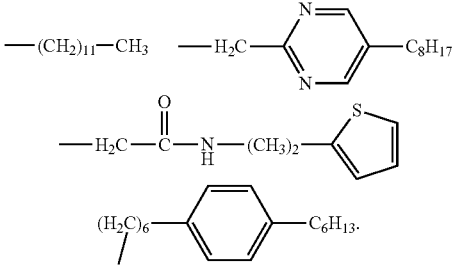

In one embodiment, D is attached to the squaric acid or croconic acid group/moiety of a compound of the present disclosure such that a conjugated system is formed.

In this embodiment, $A_1$ and/or $A_2$ comprises in its structure substituted or unsubstituted aryl or heteroaryl.

In this embodiment, $A_1$ and $A_2$ each independently can be selected from

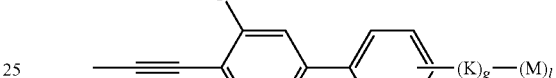

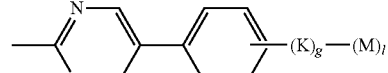

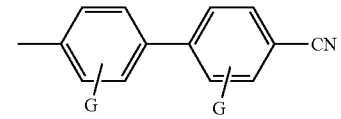

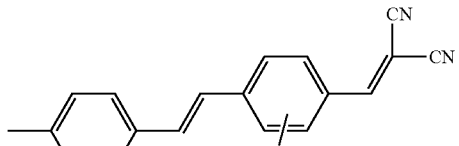

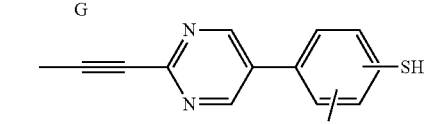

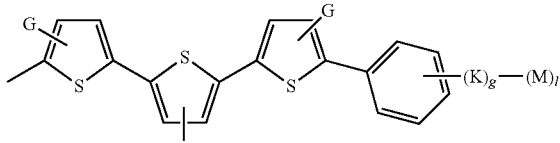

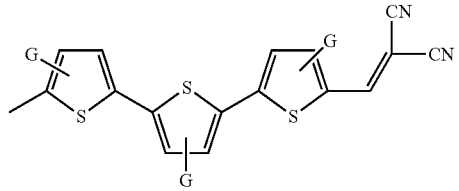

wherein, at each occurrence and independently,
G=H or any cyclic or acyclic, straight or branched substituted or non-substituted alkyl, preferably of long chain length (preferably longer chain length than M),
K being selected from O, S, N, g=0, 1, M being H or alkyl, preferably of short chain length (preferably $C_1$ or $C_2$), l=1, 2, wherein the alkyl, alkoxy, amine, thiole group —$(K)_g$-$(M)_l$ can be one or more attached to the aryl and heteroaryl rings, in o-, m-, p-position, preferably in o- and/or p-position.

In this embodiment, $A_1$ and $A_2$ each independently can preferably be selected from

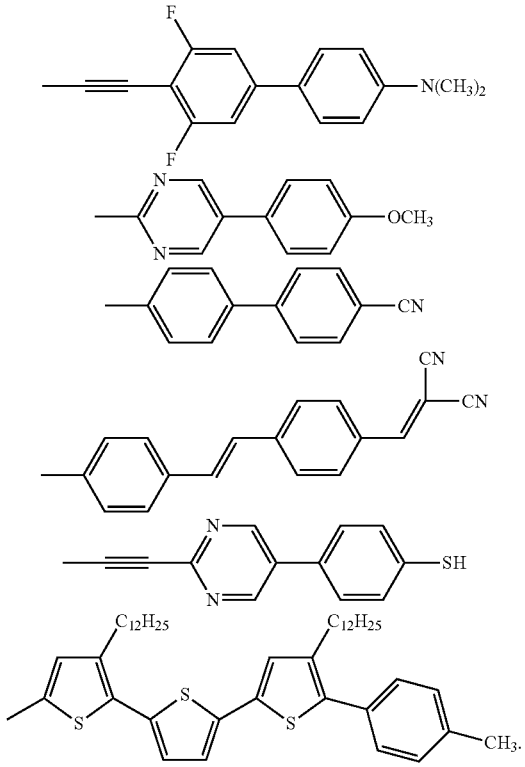

In one embodiment, D is a conjugated system.

In this embodiment, $A_1$ and/or $A_2$ includes in its structure at least one $B_1$ moiety, wherein $B_1$ is selected from the moieties shown in formula 13 as defined above.

D preferably comprises in its structure an electron-donating group.

Wherein, preferably, $A_1$ and $A_2$ each independently is selected from H, or any cyclic or acyclic substituted, or non-substituted alkyl, or heteroalkyl, or any straight or branched chain moiety of general formula —$[(CXY)_{n1}$—$(B_1)_{n3}$—$(B_2)_{n2}$—$W]_p$—R, wherein, at each occurrence and independently, p=0-18, preferably 0-3, n1 and n2 are independently=0-18, preferably 0-4, n3=0-1, wherein W is selected from —O—, —S—, —N(R)—, —C(R)=N, —C(O)N(R)—, —Si(R)$_2$—, —OC(O)—, —C(O)O—, —C(O)—, —S(O)$_2$—, —N(R)C(O)—, and —N(R)S(O)$_2$—, wherein X, Y, R each independently is selected from H or any straight or branched alkyl chain of general formula —$C_nH_{2n+1}$, or ester, carboxylic acid —COOR$^1$, alkoxy —OR$^1$, thiol —SR$^1$, amine —NR$^1_2$, nitro —NO$_2$, cyano —CN, -isothiocyanato —SCN, -trifluoromethyl —CF$_3$, or halogen F, Cl, Br, I, or substituted or unsubstituted aryl or heteroaryl, or ester, carboxylic acid, alkoxy, thiol, amine, nitro, cyano functionalized or halogenated straight or branched alkyl, wherein R$^1$ is H or any alkyl or aryl or heteroaryl and n=0-18, wherein $B_1$ is selected from the moieties shown in formula 13 as defined above and $B_2$ is —$C_6H_4$— or CXY.

In this embodiment, $A_1$ and/or $A_2$ independently comprises in its structure a substituted amine derivative, preferably an alkyl or an alkoxy substituted triphenylamine.

In this embodiment, $A_1$ and $A_2$ each independently can be selected from

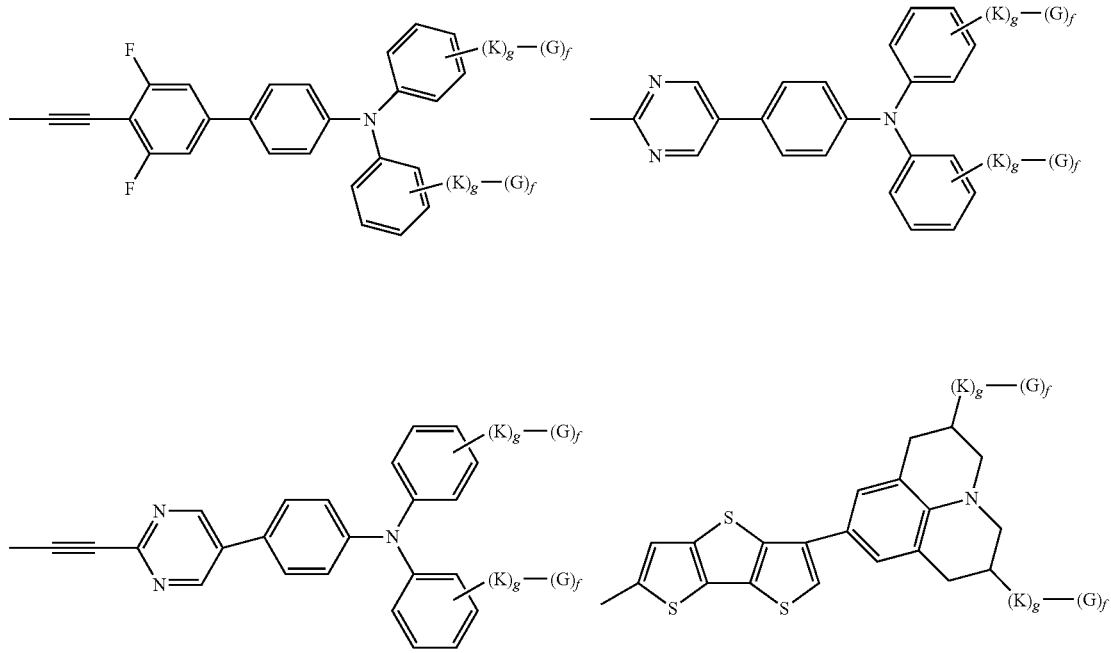

-continued
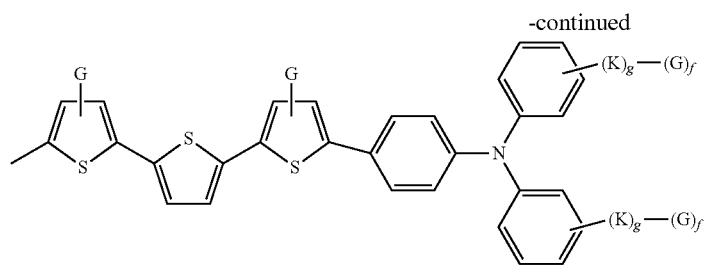
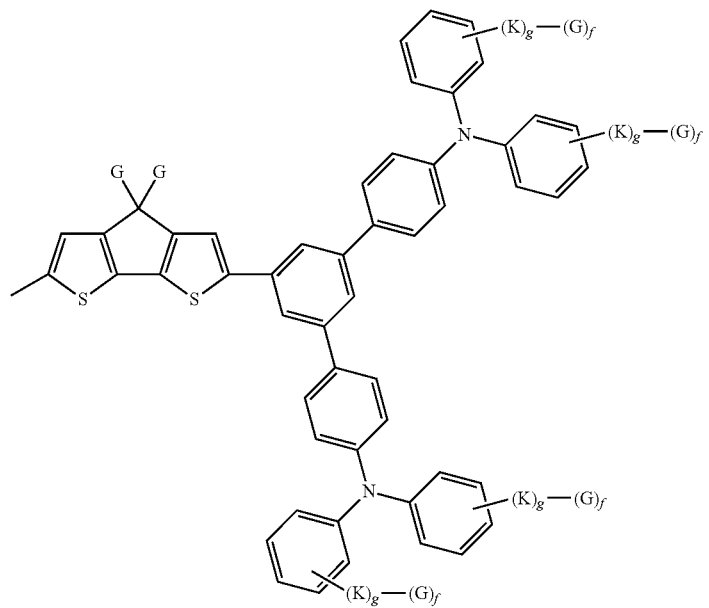
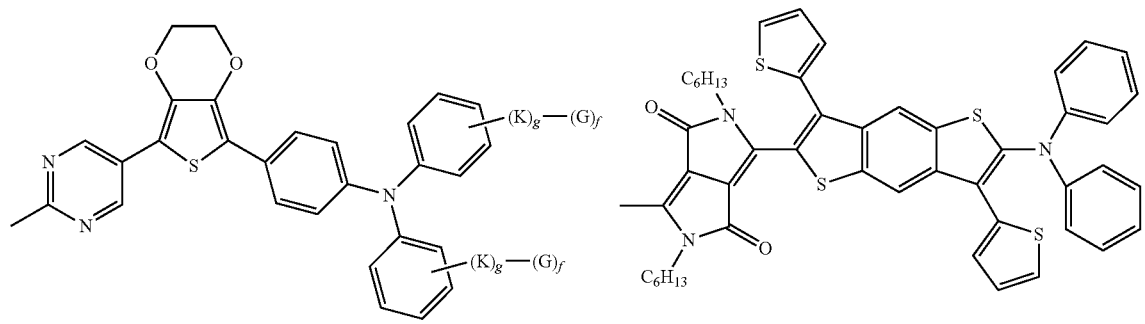
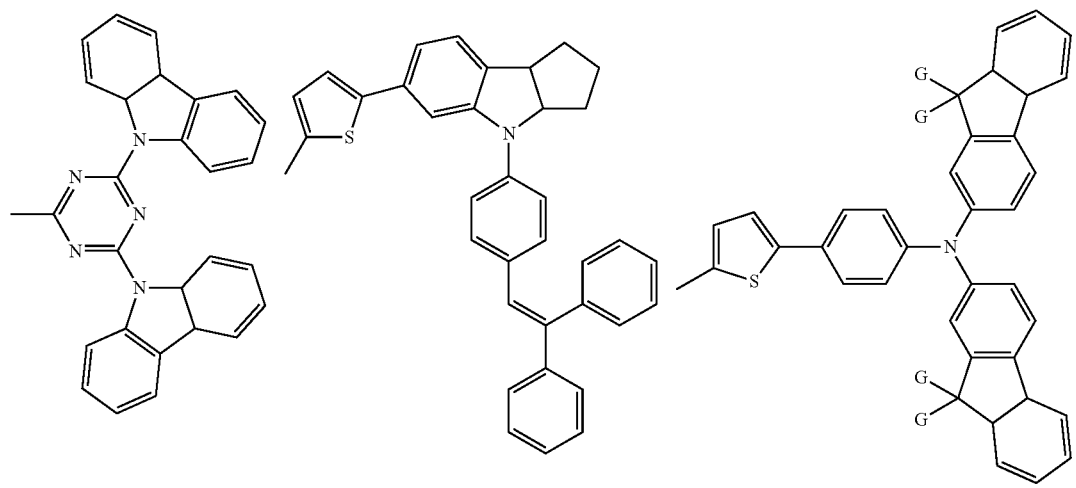

-continued

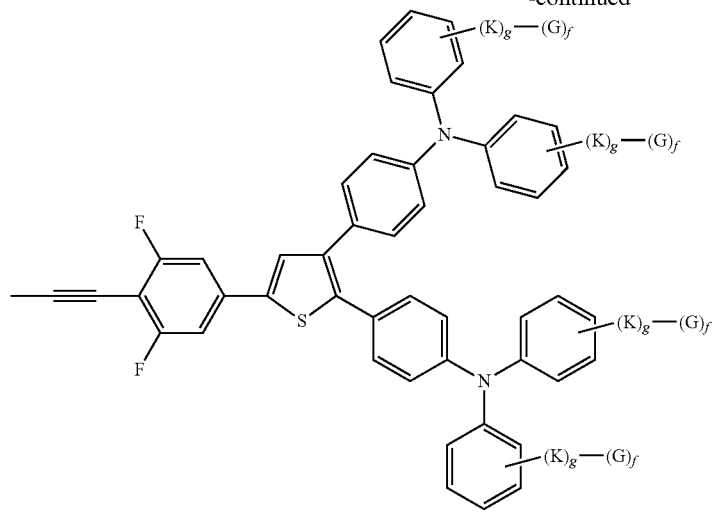

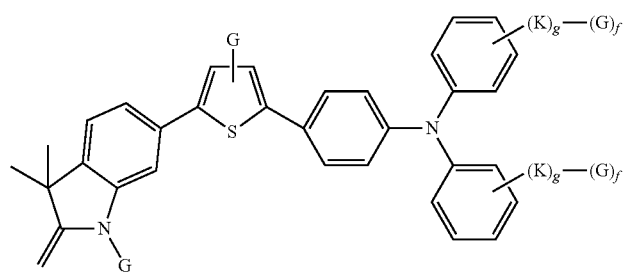

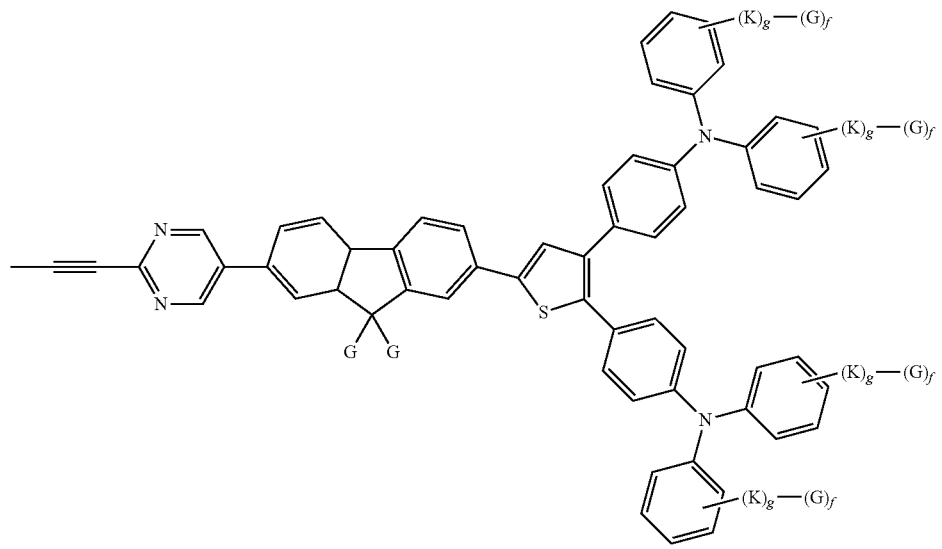

wherein, at each occurrence and independently,
G being any cyclic or acyclic substituted, or straight or branched alkyl,
f=1, 2,
K being selected from O, S, N
g=0, 1, wherein the alkyl, alkoxy, amine, thiole group —$(K)_g$-$(G)_f$ can be one or more attached to the aryl and heteroaryl rings, in o-, m-, p-position, preferably in o- and/or p-position.

In this embodiment, $A_1$ and $A_2$ each independently can preferably be selected from 25 26
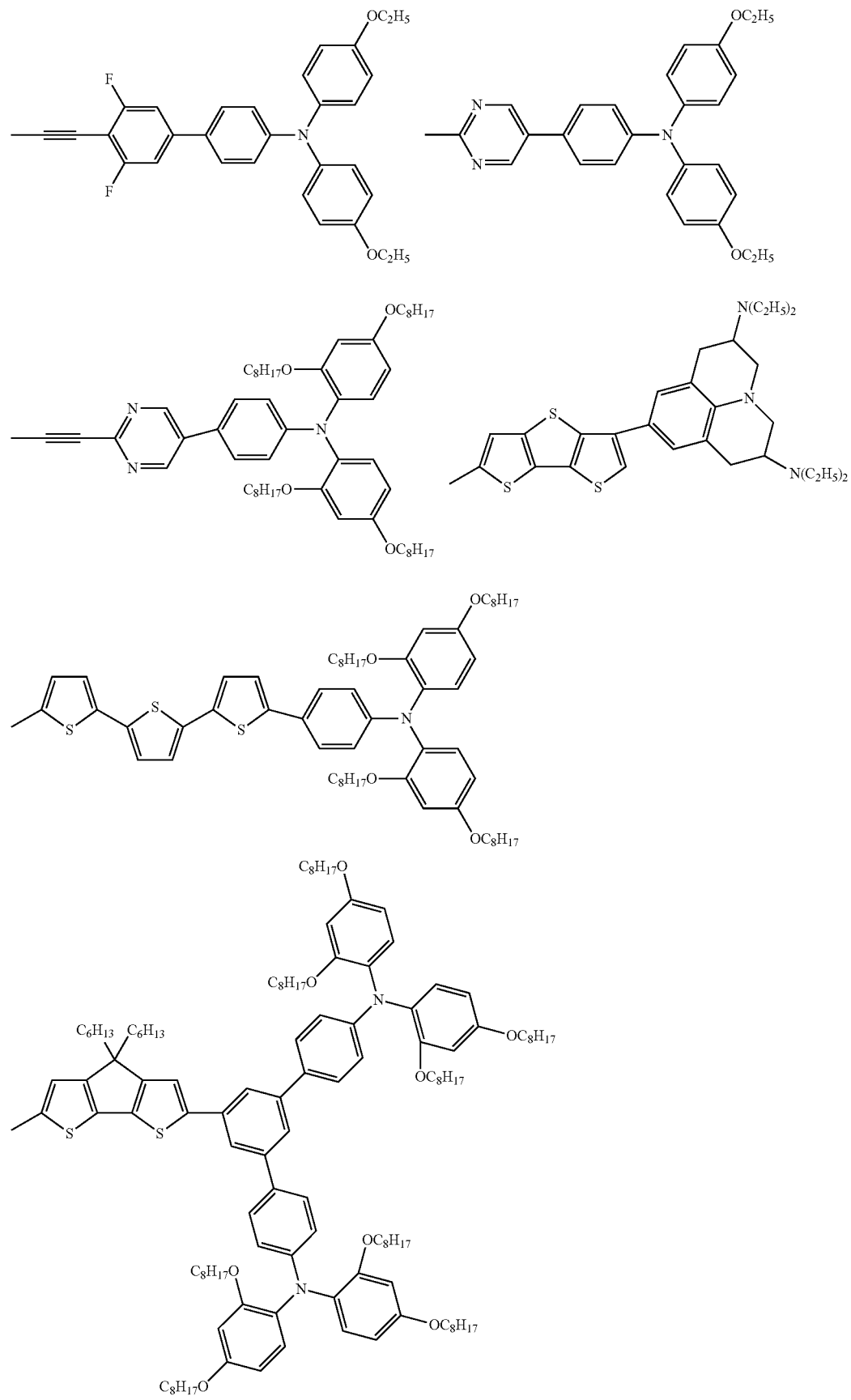

27 28
-continued
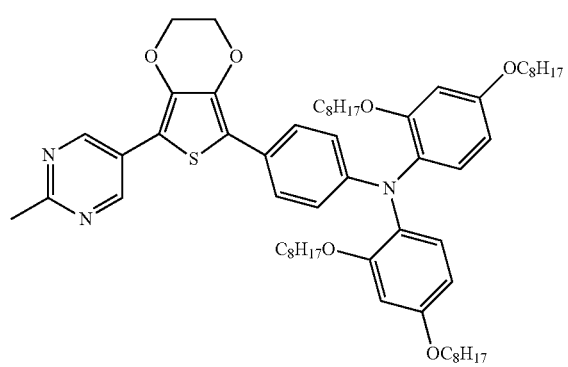
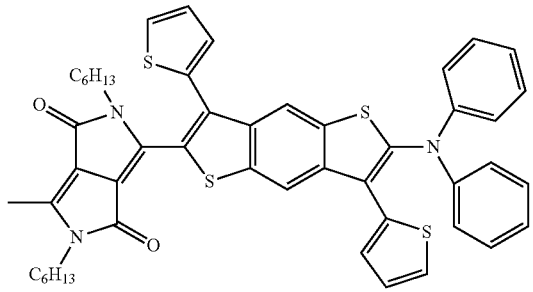
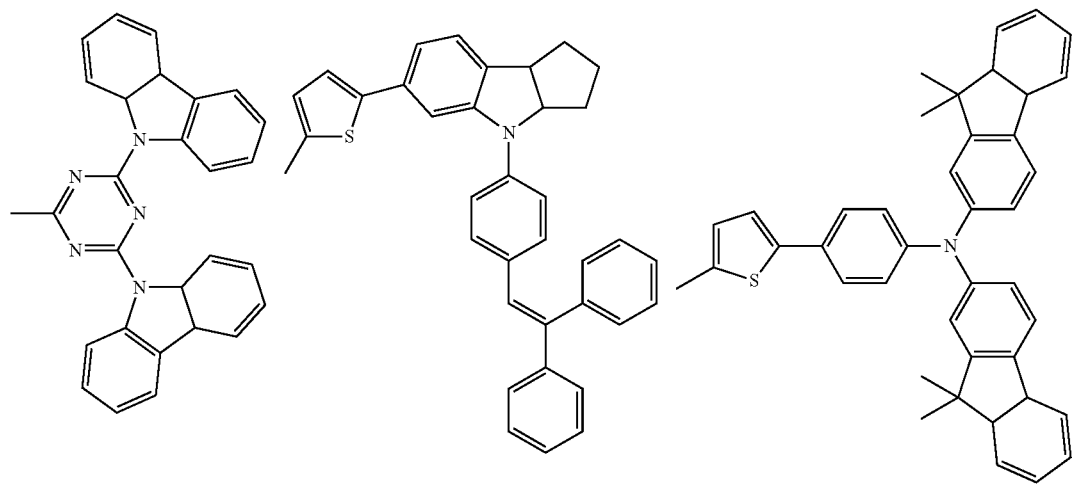
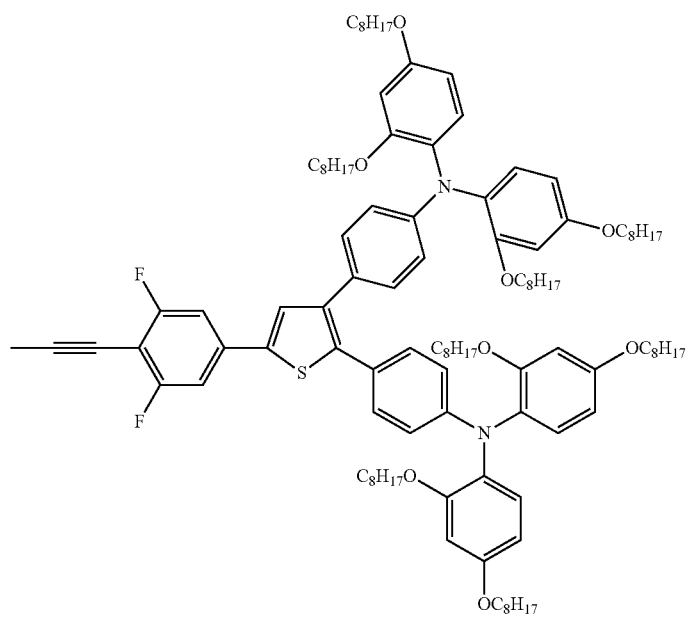

-continued
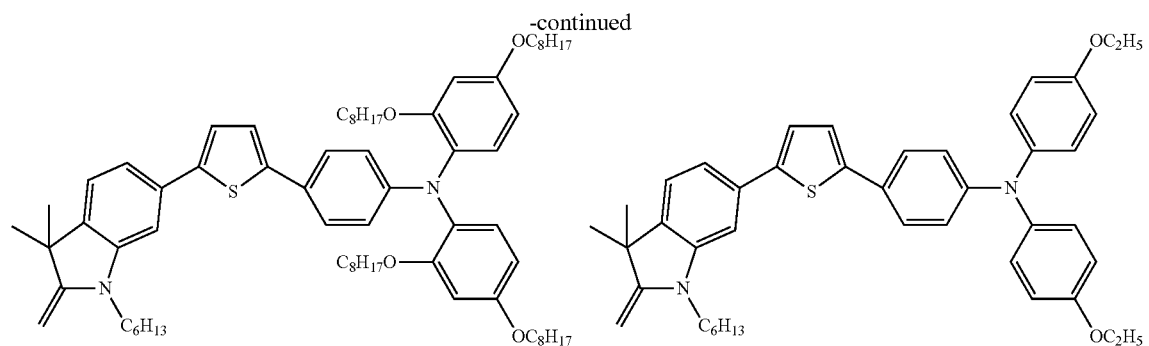
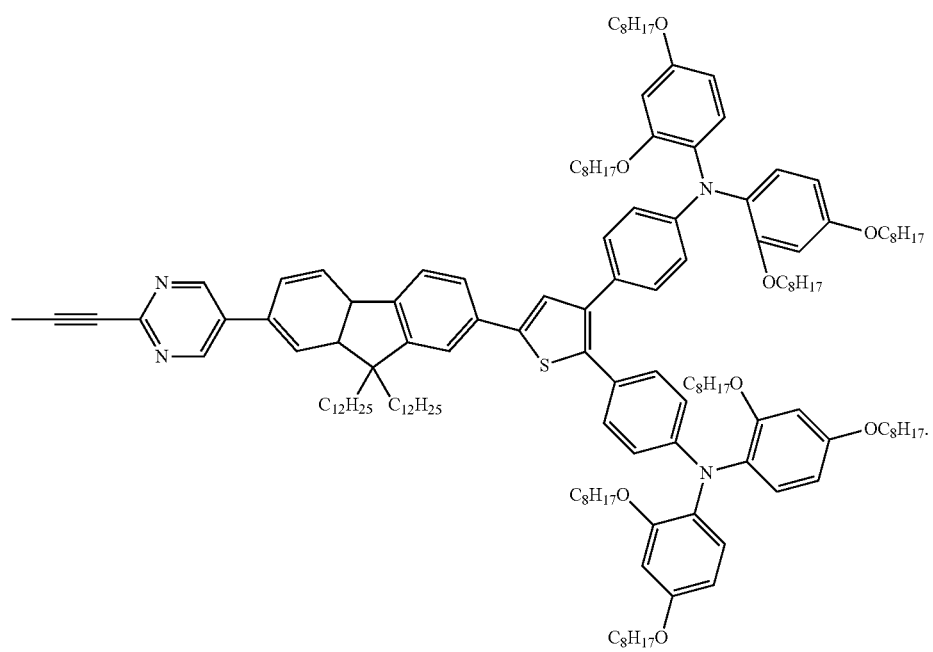
In one embodiment, $A_1$ and/or $A_2$ each independently is selected from
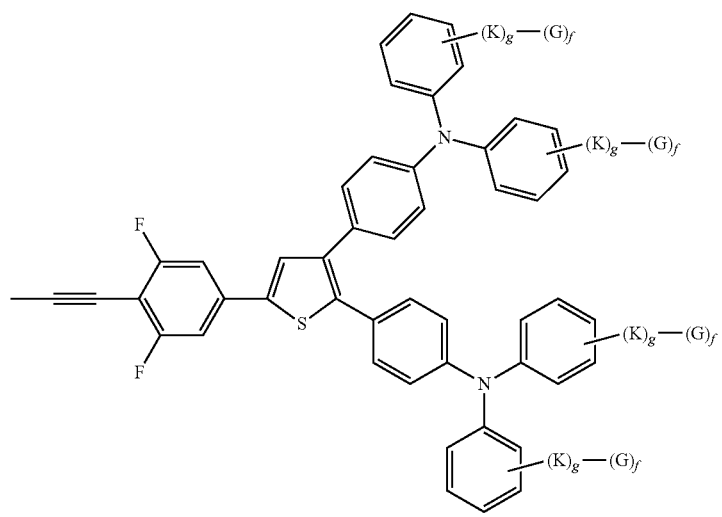

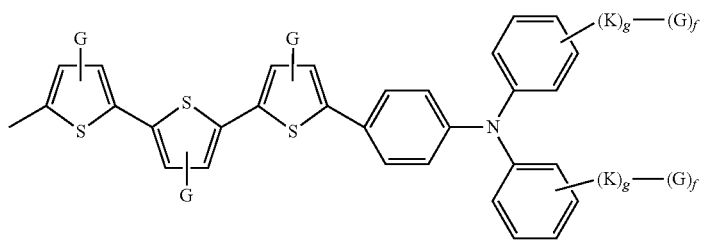
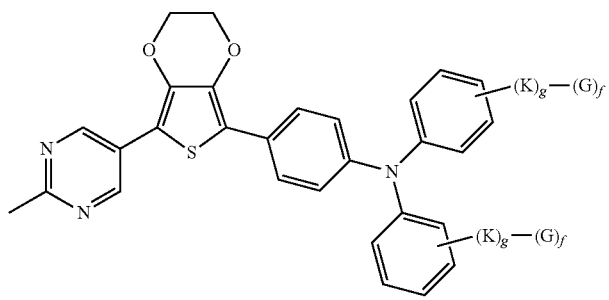
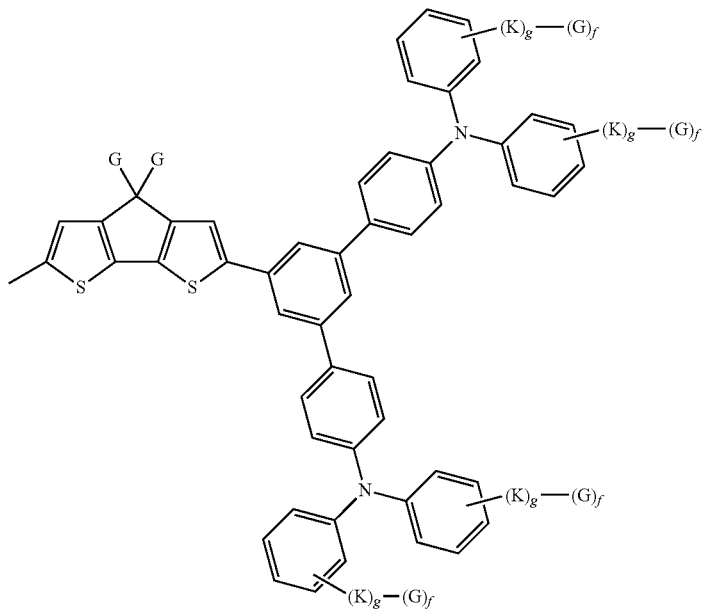
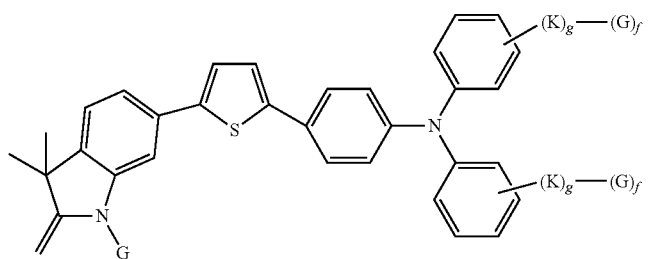

-continued

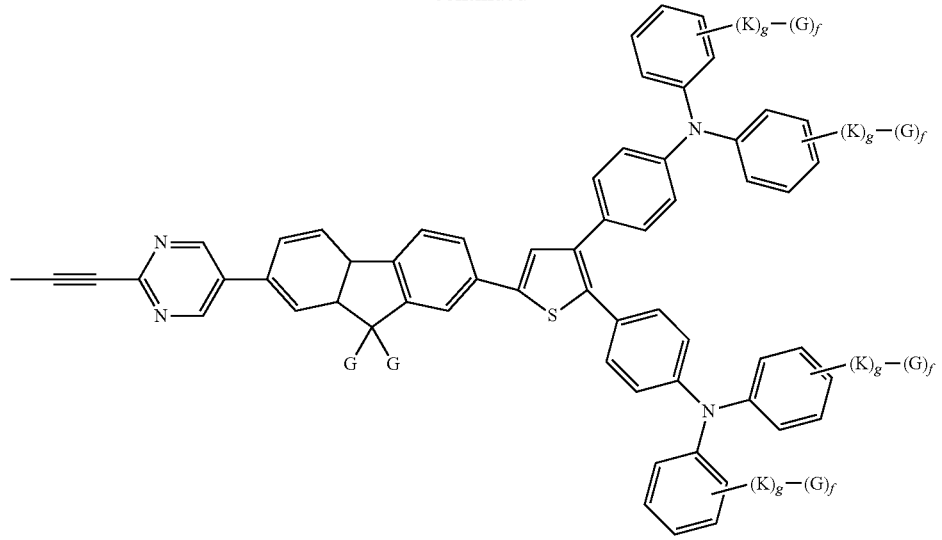

wherein, at each occurrence and independently,
G being any cyclic or acyclic substituted, or straight or branched alkyl,
f=1, 2,
K being selected from O, S, N,
g=0, 1, wherein the alkyl, alkoxy, amine, thiole group —$(K)_g$-$(G)_f$ can be one or more attached to the aryl and heteroaryl rings, in o-, m-, p-position, preferably in o- and/or p-position.

In this embodiment, $A_1$ and/or $A_2$ each independently can preferably be selected from

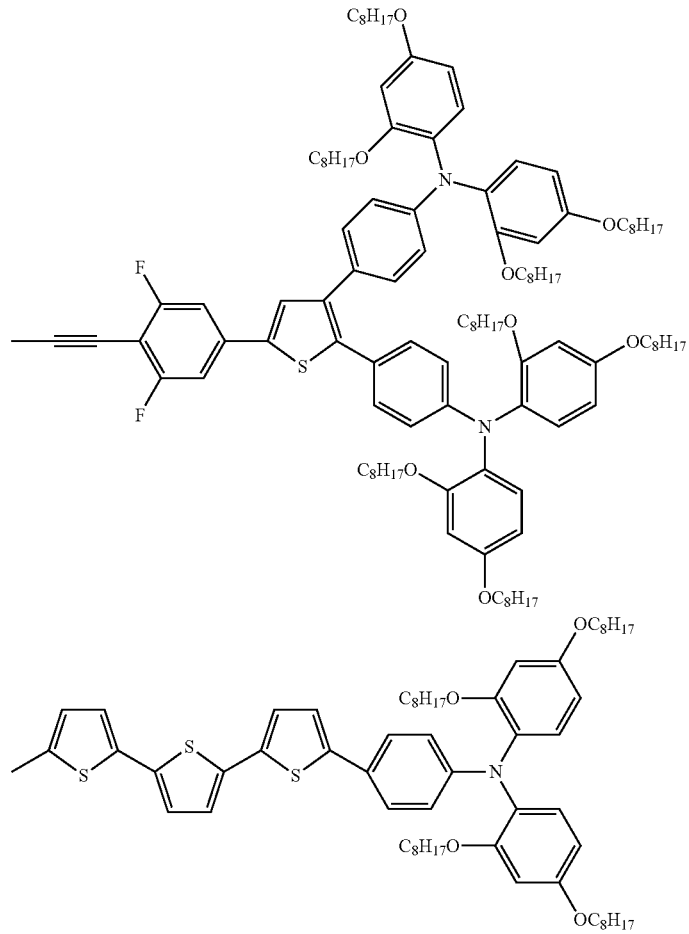

-continued
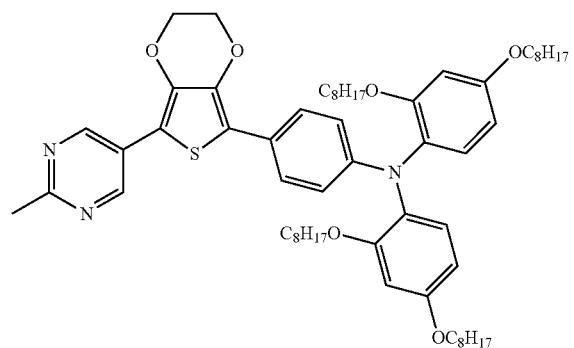
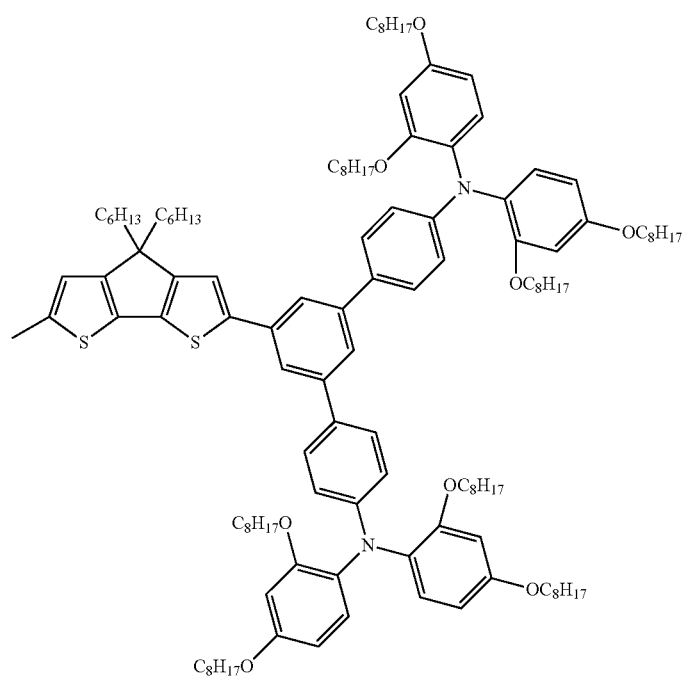
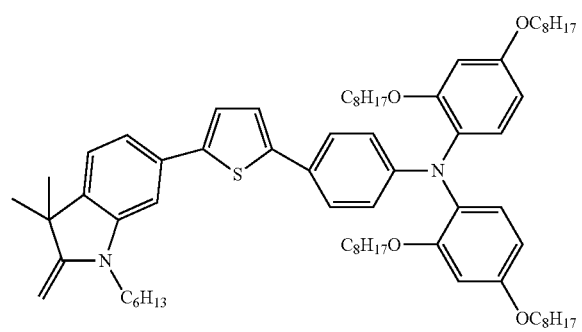

-continued

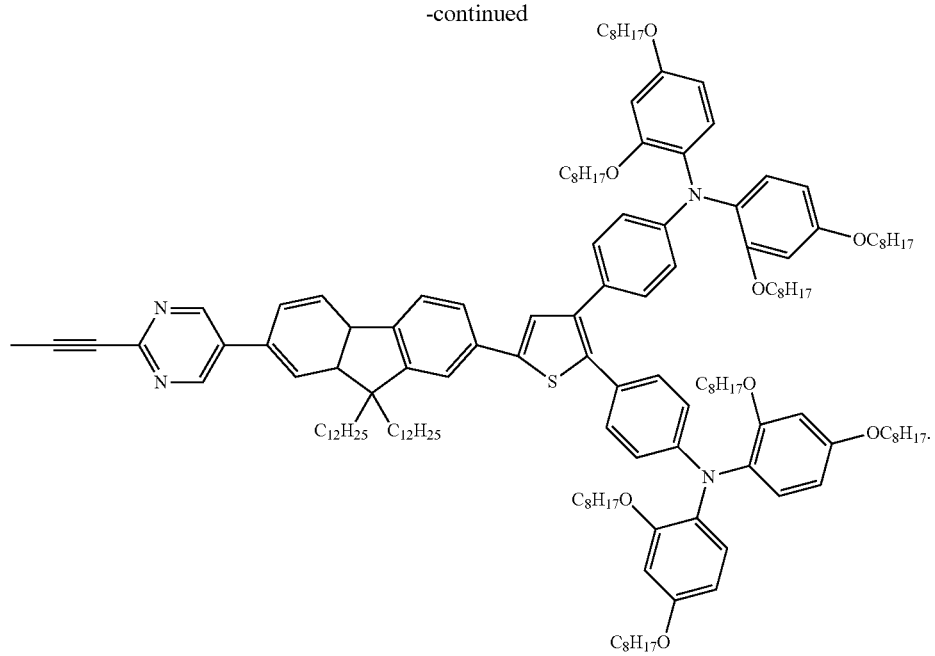

In one embodiment, a compound of the disclosure is selected from any one of

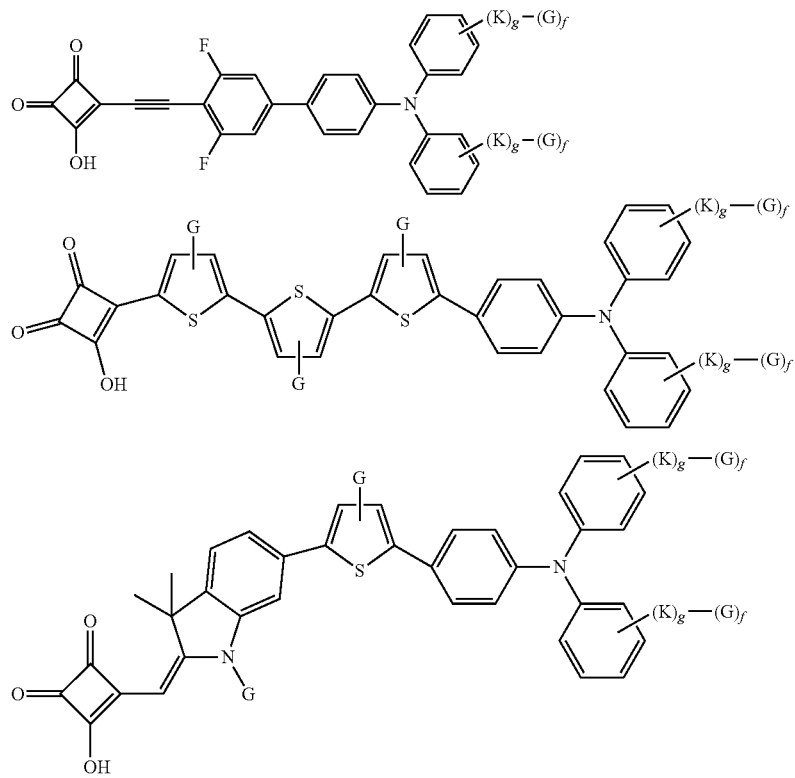

wherein, at each occurrence and independently,

G being any cyclic or acyclic substituted, or straight or branched alkyl, f=1, 2, K being selected from O, S, N, g=0, 1, wherein the alkyl, alkoxy, amine, thiole group —(K)$_g$-(G)$_f$ can be one or more attached to the aryl and heteroaryl rings, in o-, m-, p-position, preferably in o- and/or p-position.

Examples of compounds according to the disclosure:
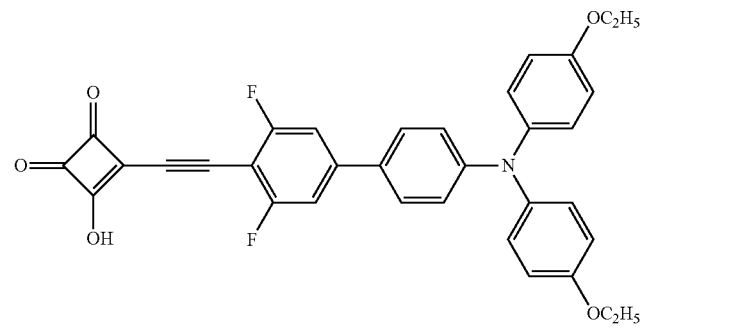
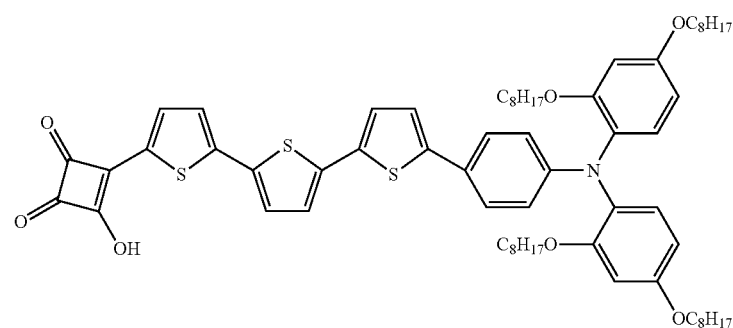
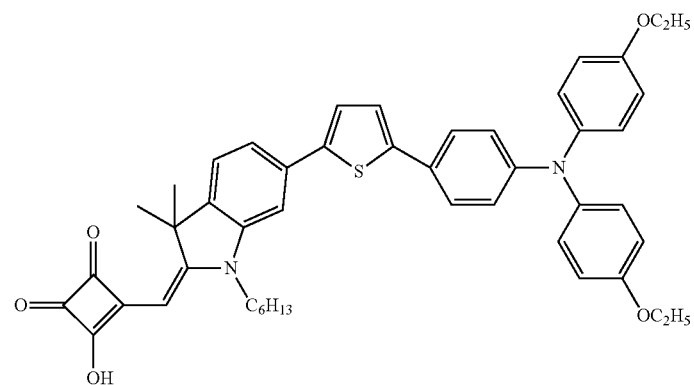
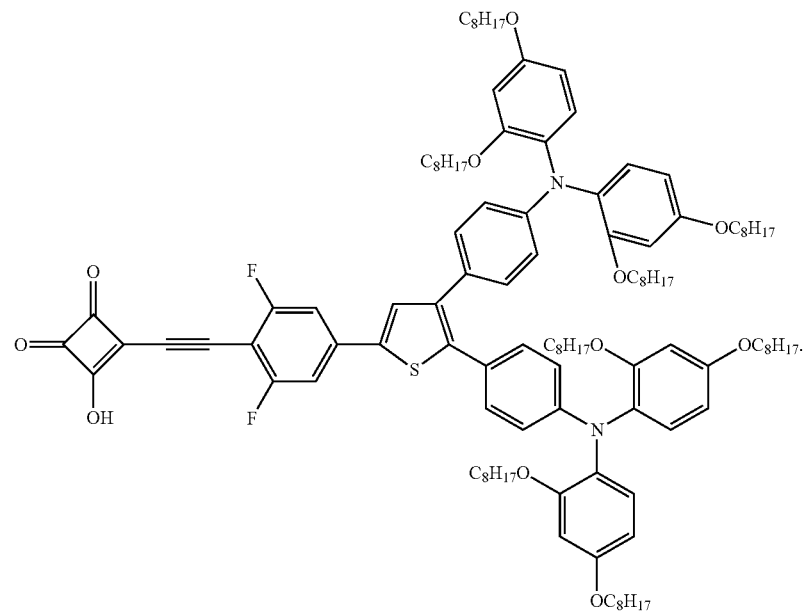

The objects of the present disclosure are also solved by the use of at least one compound according to the disclosure for modifying or influencing the work function;
the surface energy;
the tunnelling barrier; and/or
the light absorption capability of a conducting, semiconducting, or insulating organic or inorganic substrate.

One compound can have an influence on more than one of the above described properties.

For example, one compound can simultaneously influence work function and light absorption capability of the conducting, semiconducting, or insulating organic or inorganic substrate. For example, one compound can simultaneously influence work function and surface energy and light absorption capability of the conducting, semiconducting, or insulating organic or inorganic substrate.

In one embodiment, said use comprises adsorption of said at least one compound onto a surface of said conducting, semiconducting, or insulating organic or inorganic substrate.

In one embodiment, said adsorption occurs by exposing said conducting, semiconducting, or insulating organic or inorganic substrate to a solution comprising at least one compound according to the disclosure.

In one embodiment, said adsorption occurs by evaporating or spin coating a solution comprising at least one compound according to the disclosure on the surface of said conducting, semiconducting, or insulating organic or inorganic substrate.

In one embodiment, said adsorption occurs by thermal evaporation or sublimation of at least one compound according to the disclosure on the surface of said conducting, semiconducting, or insulating organic or inorganic substrate.

In one embodiment, said adsorption occurs by doctor blading or drop casting a solution or matrix comprising at least one compound according to the disclosure on the surface of said conducting, semiconducting, or insulating organic or inorganic substrate or by doctor blading or drop casting at least one compound according to the disclosure on the surface of said conducting, semiconducting, or insulating organic or inorganic substrate.

In one embodiment, at least one compound which is selected from a compound of any one of formulas 2 to 12 is used for modifying or influencing the work function, the surface energy, the tunnelling barrier and/or the light absorption capability of a conducting, semiconducting, or insulating organic or inorganic substrate.

As described above, at least one compound according to the disclosure can be used for modifying or influencing the work function of a conducting, semiconducting, or insulating organic or inorganic substrate.

The work function ($\Phi$) is a fundamental property of materials that plays a key role in many physical and chemical phenomena, such as the semiconductor field-effect, photo- and thermionic electron emission, catalysis, etc. The work function is defined as the minimum work required for extracting an electron from the Fermi level of a condensed phase and placing it into the so-called vacuum level just beyond the influence of the electrostatic forces. The Fermi level of electrically conducting materials (e.g., metals or heavily doped semiconductors) is the upper limit of the valence band, while for semiconducting or insulating materials (e.g., ZnO or $Al_2O_3$) it is inside the band gap between the valence band and the conduction band. The work of extracting the electron from the Fermi level can be conceptually divided between the work required to free the electron from the bulk and the work associated with moving the electron through the surface.

In one embodiment, at least one compound according to the disclosure can be used for increasing work function.

In this embodiment, the squaric acid or croconic acid group of a compound according to the present disclosure has a dipole moment with a first polarity, and D is a substituent with at least one or several uncharged or charged polar components that has a second polarity which is opposite said first polarity.

In this embodiment, D is preferably an electron-donating group.

The squaric acid or croconic acid moiety is a strong electron-accepting group and at the same time the anchoring group by which the compound will attach on the surface.

When D is an electron-donating group the induced dipole moment of the compound will direct away from the surface and will shift work function to lower values, towards vacuum level (i.e. increases work function).

In this embodiment, the compound is selected from a compound of any one of formulas 2 to 12.

In this embodiment, $A_1$ and $A_2$ each independently is preferably selected from H, or any cyclic or acyclic substituted or non-substituted alkyl, or heteroalkyl, or any straight or branched chain moiety of general formula —[(CXY)$_{n1}$—(B$_1$)$_{n3}$—(B$_2$)$_{n2}$—W]$_p$—R, wherein, at each occurrence and independently, p=0-18, preferably 0-3, n1 and n2 are independently=0-18, preferably 0-4, n3=0-1, wherein W is selected from —O—, —S—, —N(R)—, —C(R)=N—, —C(O)N(R)—, —Si(R)$_2$—, wherein X, Y, R each independently is selected from H or any straight or branched alkyl chain of general formula —C$_n$H$_{2n+1}$, or ester, carboxylic acid —COOR$^1$, alkoxy —OR$^1$, thiol —SR$^1$, amine —NR$^1{}_2$, nitro —NO$_2$, cyano —CN, -isothiocyanato —SCN, -trifluoromethyl —CF$_3$, or halogen F, Cl, Br, I, or substituted or unsubstituted aryl or heteroaryl, or ester, carboxylic acid, alkoxy, thiol, amine, nitro, cyano functionalized or halogenated straight or branched alkyl, wherein R$^1$ is H or any alkyl or aryl or heteroaryl and n=0-18, wherein B$_1$ is selected from the moieties shown in formula 13 as defined above and B$_2$ is —C$_6$H$_4$— or CXY.

In this embodiment, A$_1$ and/or A$_2$ comprises A$_1$ and/or A$_2$ comprises alkoxy, amine or thiole groups in its structure.

In this embodiment, A$_1$ and A$_2$ each independently can be selected from

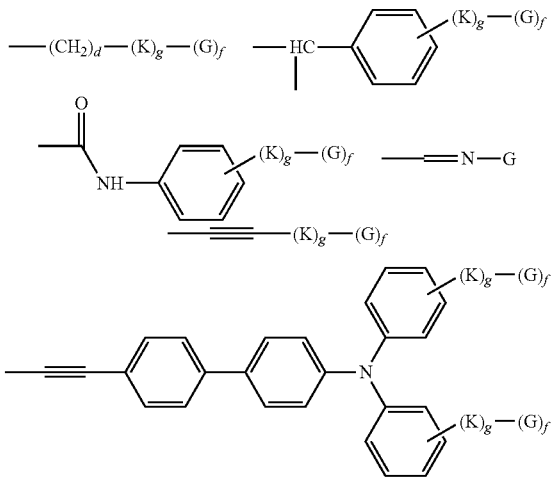

-continued

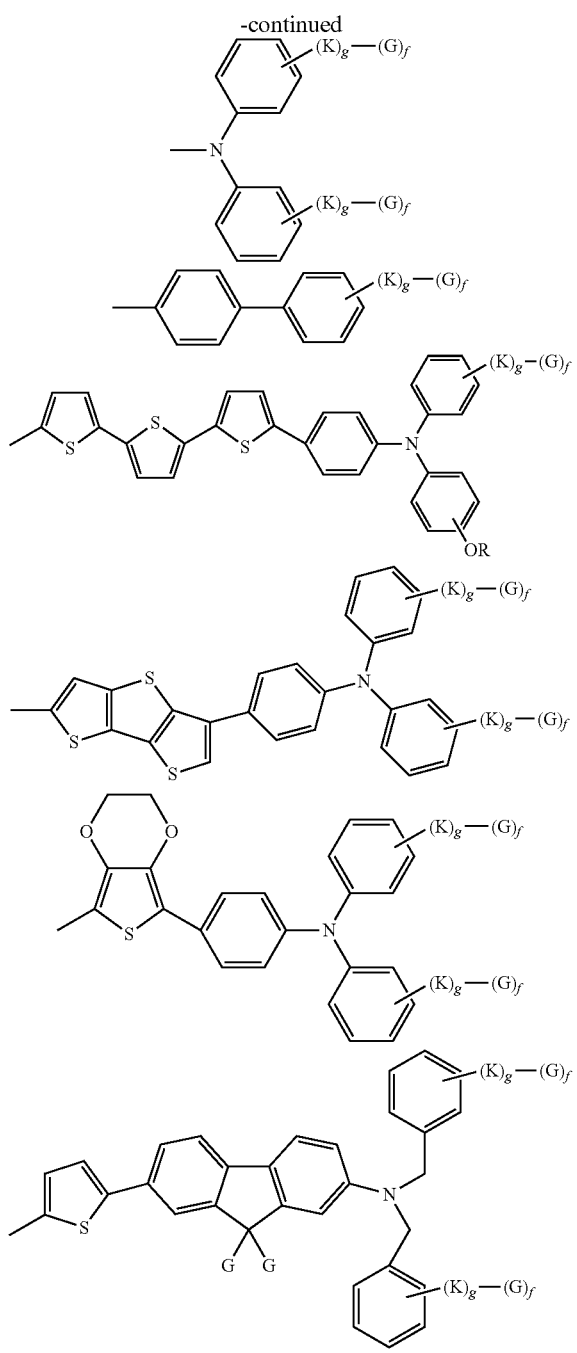

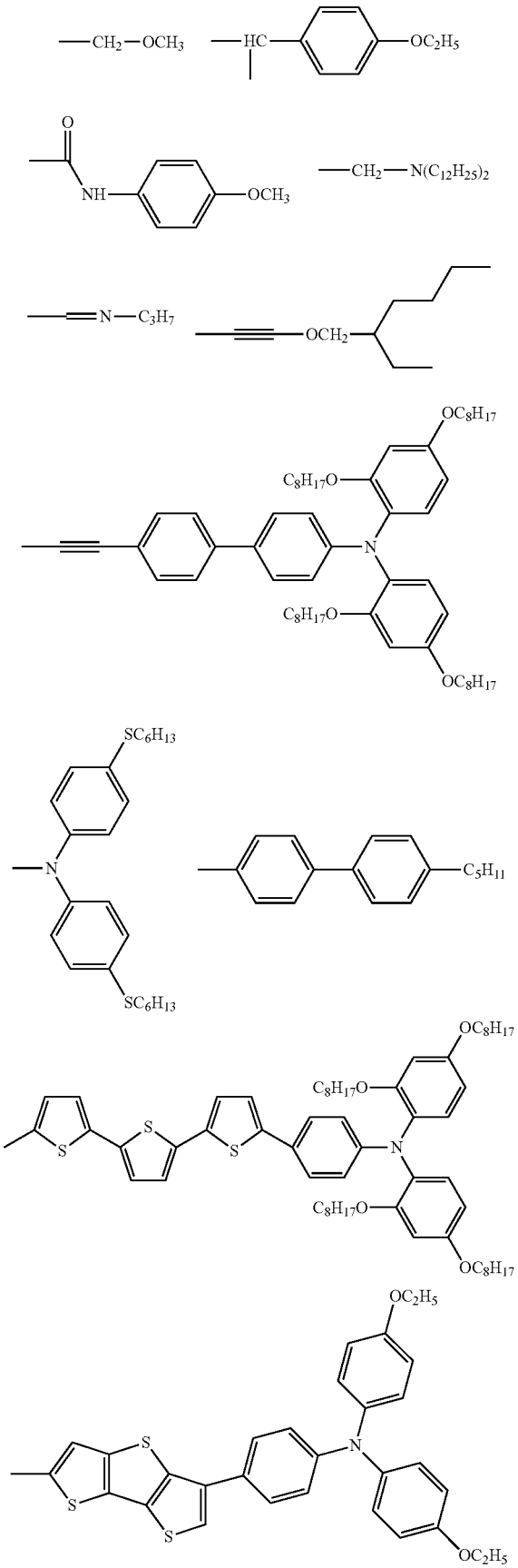

wherein, at each occurrence and independently,
  d=0-6, preferably 0-2,
  G being any cyclic or acyclic substituted, or straight or branched alkyl,
  f=1, 2,
  K being selected from O, S, N,
  g=0, 1,
wherein the alkyl, alkoxy, amine, thiole group —(K)$_g$-(G)$_f$ can be one or more attached to the aryl and heteroaryl rings, in o-, m-, p-position, preferably in o- and/or p-position.

In this embodiment, $A_1$ and $A_2$ each independently can preferably be selected from -continued

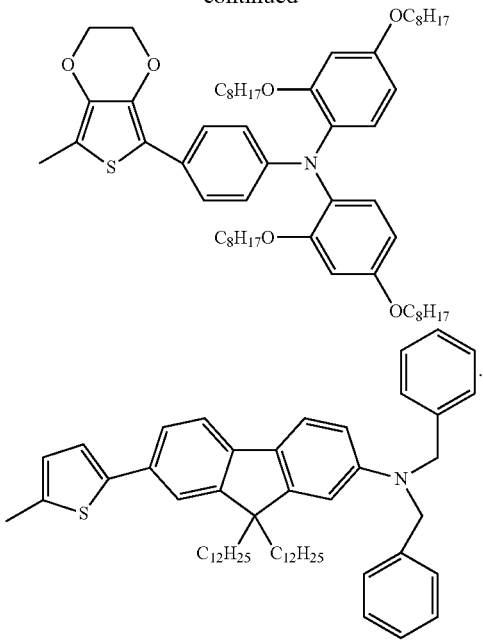

In one embodiment, at least one compound according to the disclosure can be used for decreasing work function.

In this embodiment, the squaric acid or croconic acid group of a compound according to the present disclosure has a dipole moment with a first polarity, and D is a substituent with at least one or several uncharged or charged polar components that has a second polarity which is the same as said first polarity.

In this embodiment, D is preferably an electron-accepting group.

The squaric acid or croconic acid moiety is a strong electron-accepting group and at the same time the anchoring group by which the compound will attach on the surface.

When D is also an electron-accepting group the total induced dipole moment of the compound will direct towards the surface and shift work function to higher values away from vacuum level (i.e. decreases work function).

In this embodiment, the compound is selected from a compound of any one of formulas 2 to 12.

In this embodiment, $A_1$ and $A_2$ each independently is preferably selected from H, or any cyclic or acyclic substituted, or non-substituted alkyl, or heteroalkyl, or any straight or branched chain moiety of general formula —[(CXY)$_{n1}$—(B$_1$)$_{n3}$—(B$_2$)$_{n2}$—W]$_p$—R, wherein, at each occurrence and independently, p=0-18, preferably 0-3, n1 and n2 are independently=0-18, preferably 0-4, n3=0-1, wherein W is selected from —OC(O), —C(O)O, —C(O), —S(O)$_2$, —N(R)C(O), and —N(R)S(O)$_2$, wherein X, Y, R each independently is selected from H or any straight or branched alkyl chain of general formula —C$_n$H$_{2n+1}$, or ester, carboxylic acid —COOR$^1$, alkoxy —OR$^1$, thiol —SR$^1$, amine —NR$^1{_2}$, nitro —NO$_2$, cyano —CN, -isothiocyanato —SCN, -trifluoromethyl —CF$_3$, or halogen F, Cl, Br, I, or substituted or unsubstituted aryl or heteroaryl, or ester, carboxylic acid, alkoxy, thiol, amine, nitro, cyano functionalized or halogenated straight or branched alkyl, wherein R$^1$ is H or any alkyl or aryl or hetero aryl and n=0-18,
wherein B$_1$ is selected from the moieties shown in formula 13 as defined above and
B$_2$ is —C$_6$H$_4$— or CXY.

In this embodiment, $A_1$ and/or $A_2$ comprises fluorinated alkyl or fluorinated phenyl groups, nitro, cyano or triazine, pyrazine, pyrimidine or pyridine.

In this embodiment, $A_1$ and $A_2$ each independently can be selected from

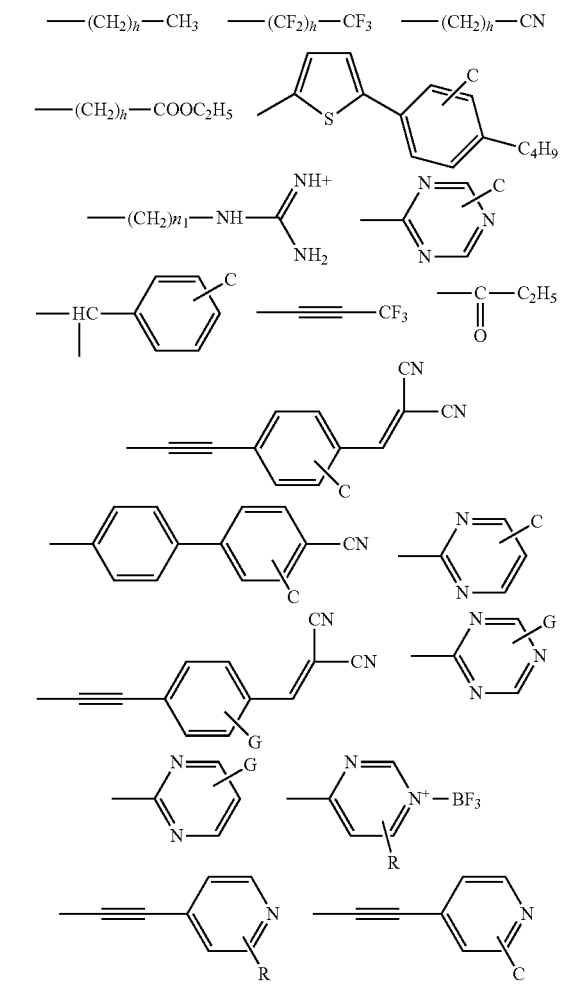

wherein, at each occurrence and independently,
G being any cyclic or acyclic substituted, or straight or branched alkyl,
C=—F, —CF$_3$, —CN, —NO2, —C(CF$_3$)$_3$,
h=0-18, preferably 0-8,
wherein G, C, each independently being one or more attached to the aryl and heteroaryl rings, in o-, m-, p-position, preferably in o- and/or p-position.

In this embodiment, $A_1$ and $A_2$ each independently can preferably be selected from

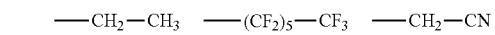
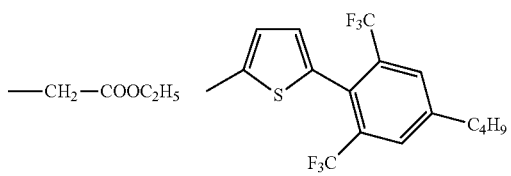

-continued

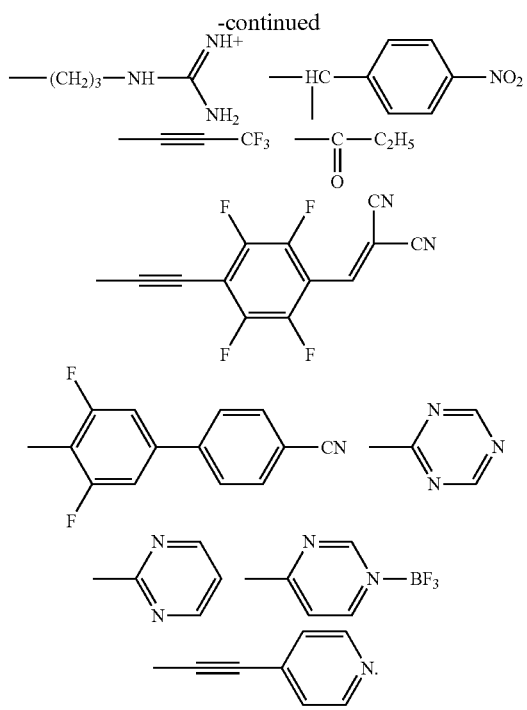

As described above, at least one compound according to the disclosure can be used for modifying or influencing the surface energy of a conducting, semiconducting, or insulating organic or inorganic substrate.

As first described by Young's equation, surface energy is the interaction between the forces of cohesion and the forces of adhesion which determines whether or not wetting, the spreading of a liquid over a surface, occurs. If complete wetting does not occur, then a bead of liquid will form, with a contact angle which is a function of the surface energies of the system. Surface energy is most commonly quantified by measuring contact angle with a goniometer. Water has rather high surface energy by nature. It is polar and forms hydrogen bonds. Hydrophilicity of a surface or modified surface is indicated by smaller contact angles of a drop of water and higher surface energy. If the surface or modified surface is hydrophobic then the contact angle of a drop of water will be larger and the surface energy lower. Surface energy also influences and defines adhesion, covering or contact between surfaces of two materials. Surface energies will determine the quality of the interfaces between two materials. The surface energy of the first component will influence also the morphology and the orientation of the second material.

So for example, in the case of semicrystalline organic semiconductors for organic light emitting diodes, such as pentacene, the morphology and molecular ordering of the semiconductor layer have a significant influence on the field-effect mobility of the device and are determined by the quality of the insulator semiconductor interface, especially by the surface energy of the insulator. The surface energy of the insulator surface affects the crystal growth of the semiconductor and thus is critical to device performance (30, 31).

In organic thin-film solar cells semiconducting conjugated polymers as photoactive layers are used. One important factor influencing the efficiency of the device is the polymer morphology and the properties of the interfaces between the photoactive layer and the electrode or an underlying buffer layer. The electrical properties at the interfaces determine the series resistance which is determined by both the electrical resistivity of each layer and the contact resistance between the layers. Particularly, the contact resistance between the organic photoactive layer and the electrode can strongly impact the charge collection, which is one of the fundamental steps of energy conversion. The surface energy play in this case a significant role in the formation of the morphology by directing the phase-separation process during deposition, film drying, and annealing, and will have its own impact on device performance. Exemplary, it was shown that by controlling the surface energy of a zinc oxide (ZnO) buffer layer, an optimized morphology of the photoactive layer composed of a polymer:fullerene-derivative bulk heterojunction resulting in enhanced photocurrents and improved device performance could be achieved (32).

In one embodiment, at least one compound according to the disclosure can be used for increasing surface energy.

In this embodiment, the compound is selected from a compound of any one of formulas 2 to 12.

In one embodiment, $A_1$ and/or $A_2$ comprises in its structure a hydrophilic functional group, preferably a hydroxy (OH), thiol (SH), unsubstituted amine ($NH_2$), carboxylic acid (COOH), cyano (CN), nitro ($NO_2$), keton (CO), ester (COOR), iodide (I), bromide (Br), preferably as end-group or peripheral group.

In this embodiment, $A_1$ and $A_2$ each independently can be selected from

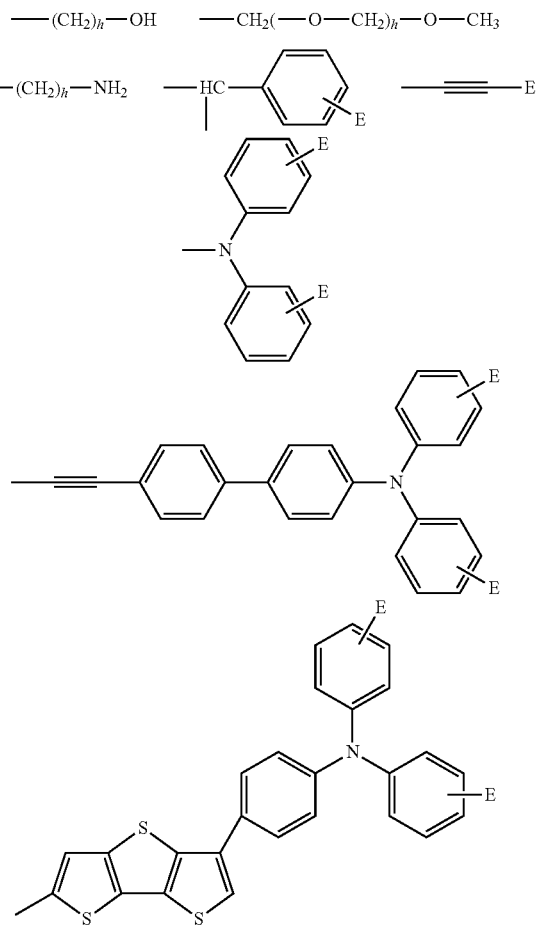

-continued

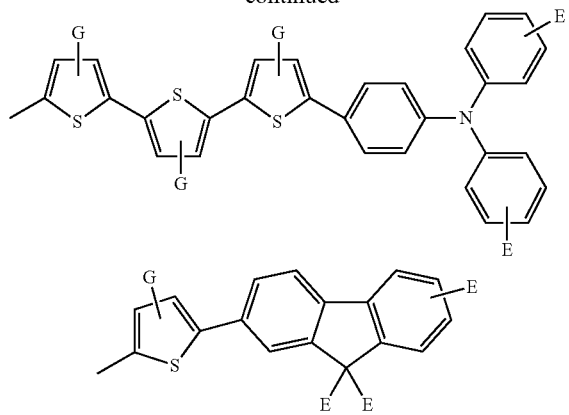

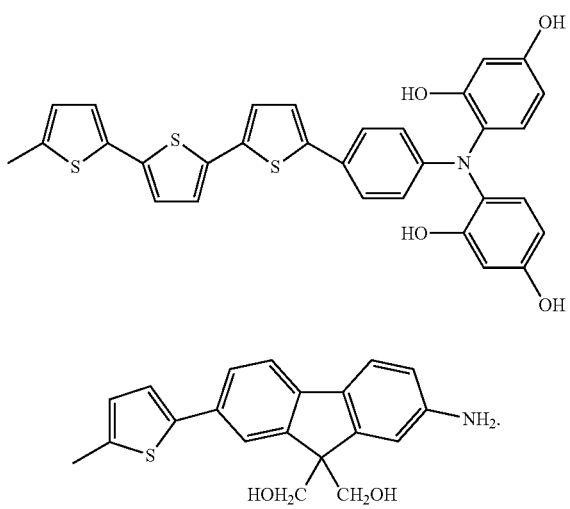

wherein, at each occurrence and independently,

E=—(CH$_2$)$_h$—OH, —(CH$_2$)$_h$—NH$_2$, —(CH$_2$)$_h$—COOH, —(CH$_2$)$_h$—CN, —(O—CH$_2$)$_h$—OH, —(CH$_2$)$_h$—SH, —(CH$_2$)$_h$—NO$_2$, —(CH$_2$)$_h$—CO, —(CH$_2$)$_h$—OHCOOR, —(CH$_2$)$_h$—I, —(CH$_2$)$_h$—Br, h=0-18, preferably 0-4, G being H or any cyclic or acyclic substituted, or straight or branched alkyl, E being one or more attached to the aryl rings, in o-, m-, p-position.

In this embodiment, A$_1$ and A$_2$ each independently can preferably be selected from

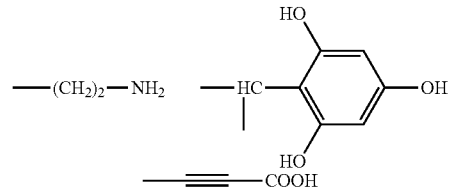

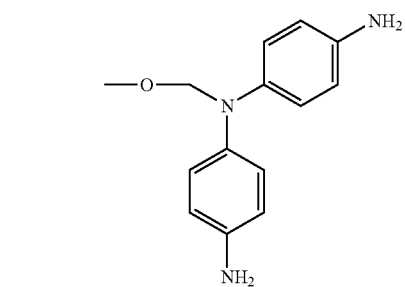

In one embodiment, at least one compound according to the disclosure can be used for decreasing surface energy.

In this embodiment, the compound is selected from a compound of any one of formulas 2 to 12.

In one embodiment, A$_1$ and/or A$_2$ comprises in its structure cyclic or acyclic, straight or branched non-substituted alkyl or aryl, or comprises in its structure alkyl substituted aryl or heteroaryl, or alkyl functionalized amine, or alkoxyl or thiole, preferably as end-group or peripheral group.

In this embodiment, A$_1$ and A$_2$ each independently can be selected from

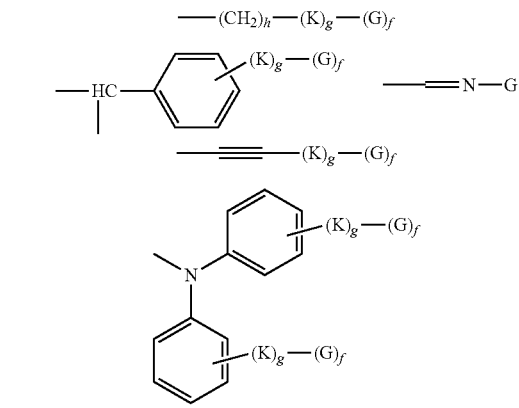

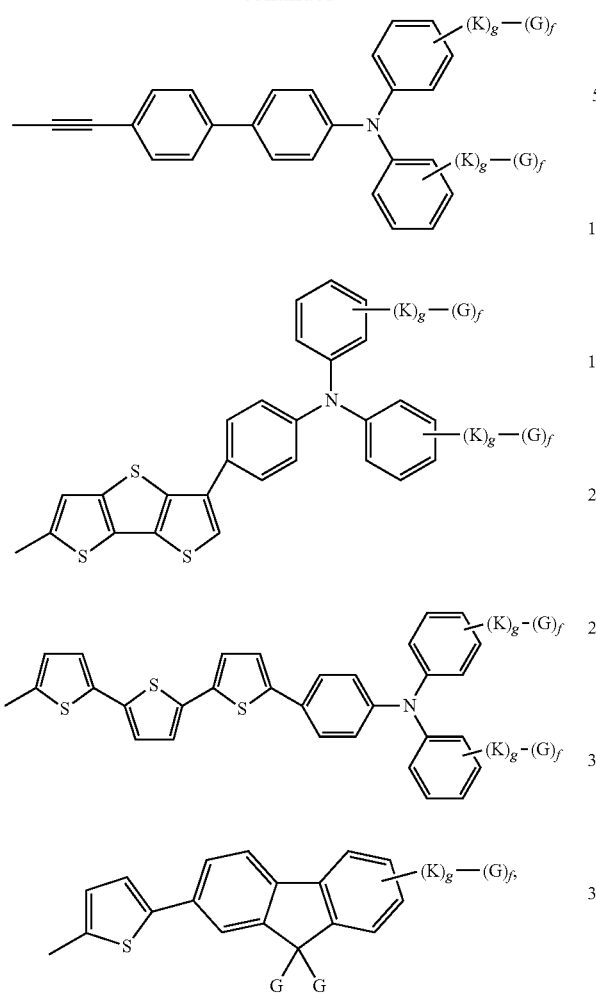

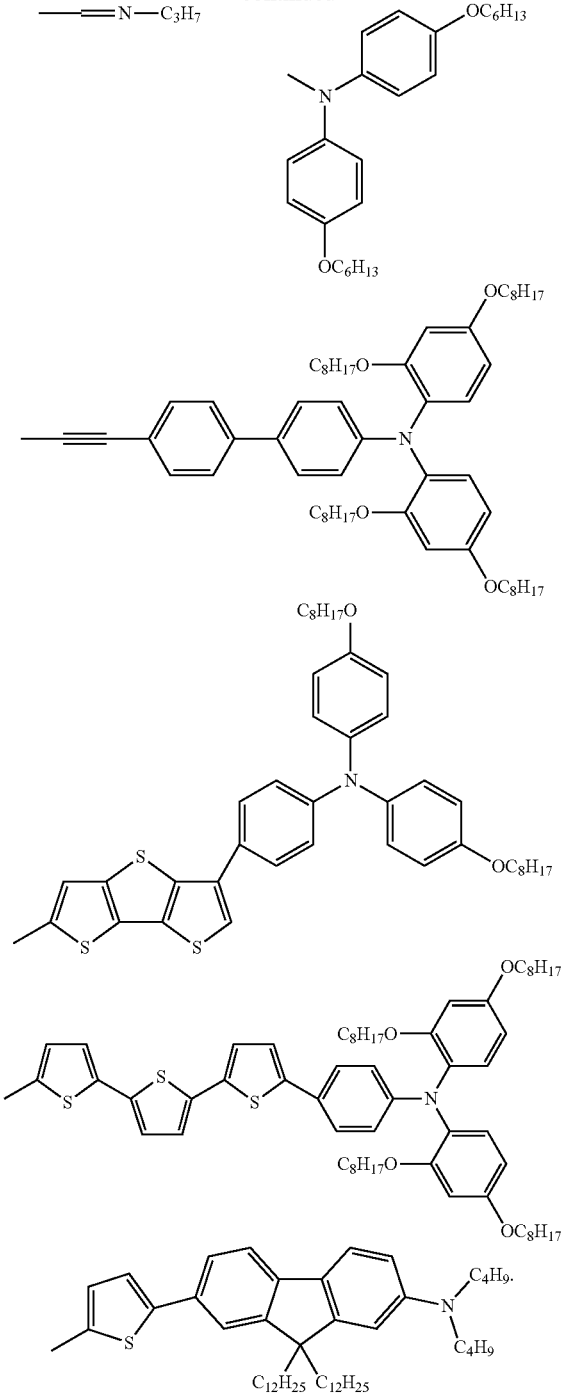

wherein, at each occurrence and independently,

G=cyclic or acyclic, straight or branched substituted or non-substituted alkyl, preferably longer than hexyl ($C_6$), h=0-18, preferably 0-2, f=1, 2, K being selected from O, S, N, g=0, 1, wherein the alkyl, alkoxy, amine, thiole group —$(K)_g$-$(G)_f$ can be one or more attached to the aryl and heteroaryl rings, in o-, m-, p-position, preferably in o- and/or p-position.

In this embodiment, $A_1$ and $A_2$ each independently can preferably be selected from

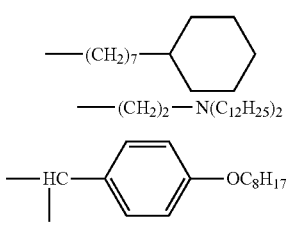

As described above, at least one compound according to the disclosure can be used for modifying or influencing the tunnelling barrier of conducting, semiconducting, or insulating organic or inorganic substrate(s), preferably the tunnelling barrier between two substrates.

Thereby, the two substrates can be both a conducting, semiconducting, or insulating organic or inorganic substrate, or two substrates can be different, such as one substrate can be conducting, the other substrate can be semiconducting.

Maybe, it's better to write "preferably between two substrates"

In the field of molecular electronics a junction includes a buffer layer on a substrate, a source and drain electrodes on the buffer layer. The compounds according to the disclosure form the buffer layer with a specific tunneling barrier. The rate and mechanism of charge transport by tunneling through them through the junction is determined by their electronic and geometrical structure of said compounds, such as length, degree of conformational flexibility, aromaticity, polarizability, dipole moment, attached functional groups.

In one embodiment, at least one compound according to the disclosure can be used for increasing the tunnelling barrier through a junction.

In this embodiment, the compound is selected from a compound of any one of formulas 2 to 12.

In this embodiment, D is attached to the squaric acid or croconic acid group/moiety of a compound of the present disclosure such that a non-conjugated system is formed.

In this embodiment, $A_1$ and/or $A_2$ comprises in its structure cyclic or acyclic, straight or branched non-substituted alkyl or aryl, or comprises in its structure alkyl substituted aryl or heteroaryl, or alkyl functionalized amine, or alkoxyl, or thiole, preferably as end-group or peripheral group.

In this embodiment, $A_1$ and $A_2$ each independently can be selected from

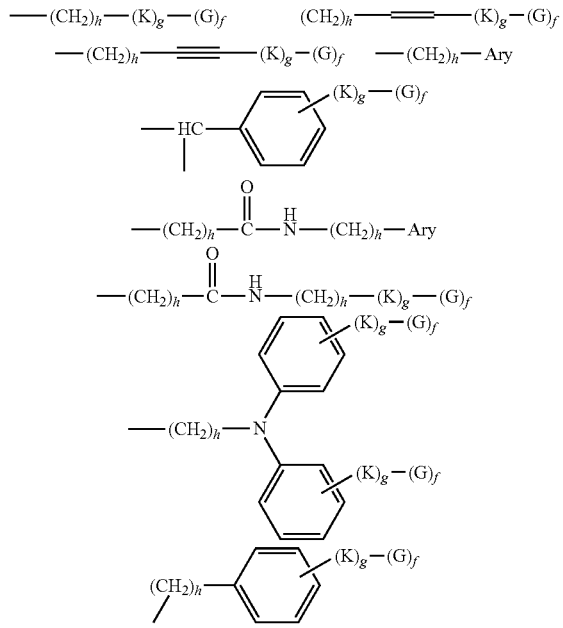

wherein, at each occurrence and independently,
G=cyclic or acyclic, straight or branched substituted or non-substituted alkyl, preferably longer than hexyl ($C_6$),
h=0-18, preferably 2-12,
f=1, 2,
K being selected from O, S, N,
g=0, 1,
wherein G being one or more attached to the aryl rings, in o-, m-, p-position,
wherein the alkyl, alkoxy, amine, thiole group —(K)$_g$-(G)$_f$ can be one or more attached to the aryl and heteroaryl rings, in o-, m-, p-position, preferably in o- and/or p-position.

In this embodiment, $A_1$ and $A_2$ each independently can preferably be selected from

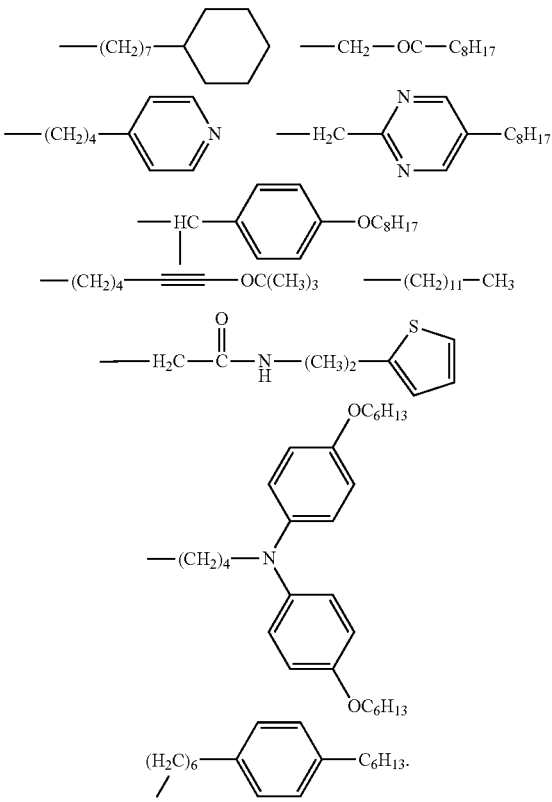

In one embodiment, at least one compound according to the disclosure can be used for decreasing the tunnelling barrier in a junction.

In this embodiment, the compound is selected from a compound of any one of formulas 2 to 12.

In this embodiment, D is attached to the squaric acid or croconic acid group/moiety of a compound of the present disclosure such that a conjugated system is formed.

Without wishing to be bound by any theory, but it appears that because of a conjugated system the charge can easily flow through the system.

D preferably comprises in its structure an electron-donating moiety because squaric acid or croconic acid are itself strong electron-accepting group. A "push-pull system" is formed either as Donor-Acceptor or as Donor-Bridge-Acceptor system, charge transport through tunneling is facilitated.

In this embodiment, $A_1$ and/or $A_2$ preferably comprises in its structure substituted or unsubstituted aryl or heteroaryl.

In this embodiment, $A_1$ and $A_2$ each independently can be selected from

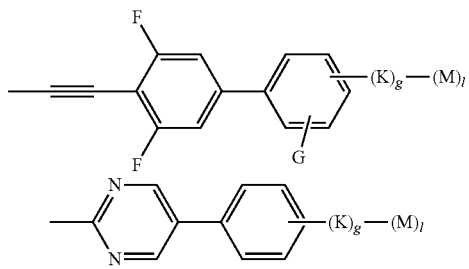

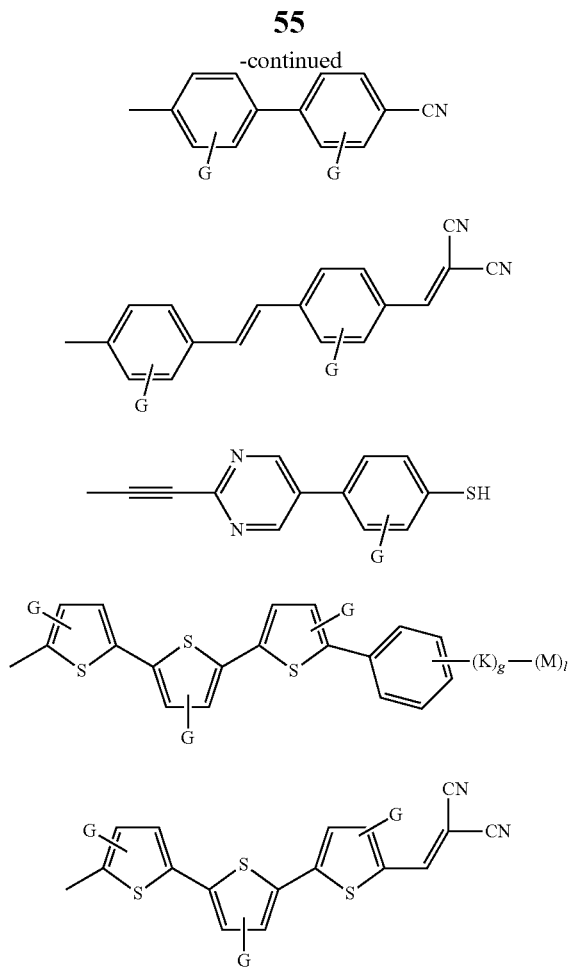

wherein, at each occurrence and independently,
G=H or any cyclic or acyclic, straight or branched substituted or non-substituted alkyl, preferably of long chain length (preferably longer chain length than M),
K being selected from O, S, N,
g=0, 1,
M being H or alkyl, preferably of short chain length (preferably $C_1$ or $C_2$),
l=1, 2,
wherein the alkyl, alkoxy, amine, thiole group —$(K)_g$-$(M)_l$ can be one or more attached to the aryl and heteroaryl rings, in o-, m-, p-position, preferably in o- and/or p-position.

In this embodiment, $A_1$ and $A_2$ each independently can preferably be selected from

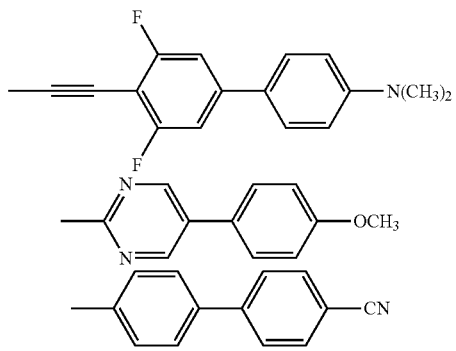

As described above, at least one compound according to the disclosure can be used for modifying or influencing the light absorption capability of a conducting, semiconducting, or insulating organic or inorganic substrate.

In this embodiment, D is a conjugated system. Preferably, D comprises in its structure at least one double bond, preferably more, or comprises a heteroatom with a free electron pair, and is attached to the squaric acid or croconic acid moiety such that a conjugated system is formed.

D preferably comprises in its structure an electron-donating moiety because squaric acid or croconic acid are itself strong electron-accepting group. A "push-pull system" is formed either as Donor-Acceptor or as Donor-Bridge-Acceptor system.

In this embodiment, D is a conjugated system as disclosed in formula 2 to 12.

In this embodiment, the compound of the present disclosure is preferably selected from any one of formulas 2 to 12.

In this embodiment, $A_1$ and $A_2$ each independently is preferably selected from H, or any cyclic or acyclic substituted, or non-substituted alkyl, or heteroalkyl, or any straight or branched chain moiety of general formula —$[(CXY)_{n1}$—$(B_1)_{n3}$—$(B_2)_{n2}$—$W]_p$—R, wherein, at each occurrence and independently, p=0-18, preferably 0-3, n1 and n2 are independently=0-18, preferably 0-4, n3=0-1, wherein W is selected from —O, —S, —N(R), —C(R)=N, —C(O)N(R)—, —Si(R)$_2$, —OC(O), —C(O)O, —C(O), —S(O)$_2$, —N(R)C(O), and —N(R)S(O)$_2$, wherein X, Y, R each independently is selected from H or any straight or branched alkyl chain of general formula —$C_nH_{2n+1}$, or ester, carboxylic acid —COOR$^1$, alkoxy —OR$^1$, thiol —SR$^1$, amine —NR$^1_2$, nitro —NO$_2$, cyano —CN, -isothiocyanato —SCN, -trifluoromethyl —CF$_3$, or halogen F, Cl, Br, I, or substituted or unsubstituted aryl or heteroaryl, or ester, carboxylic acid, alkoxy, thiol, amine, nitro, cyano functionalized or halogenated straight or branched alkyl, wherein R$^1$ is H or any alkyl or aryl or heteroaryl and n=0-18, wherein B$_1$ is selected from the moieties shown in formula 13 as defined above and B$_2$ is —$C_6H_4$— or CXY.

In this embodiment, $A_1$ and/or $A_2$ independently comprises in its structure a substituted amine derivative, preferably an alkyl or an alkoxy substituted triphenylamine.

In this embodiment, $A_1$ and $A_2$ each independently can be selected from

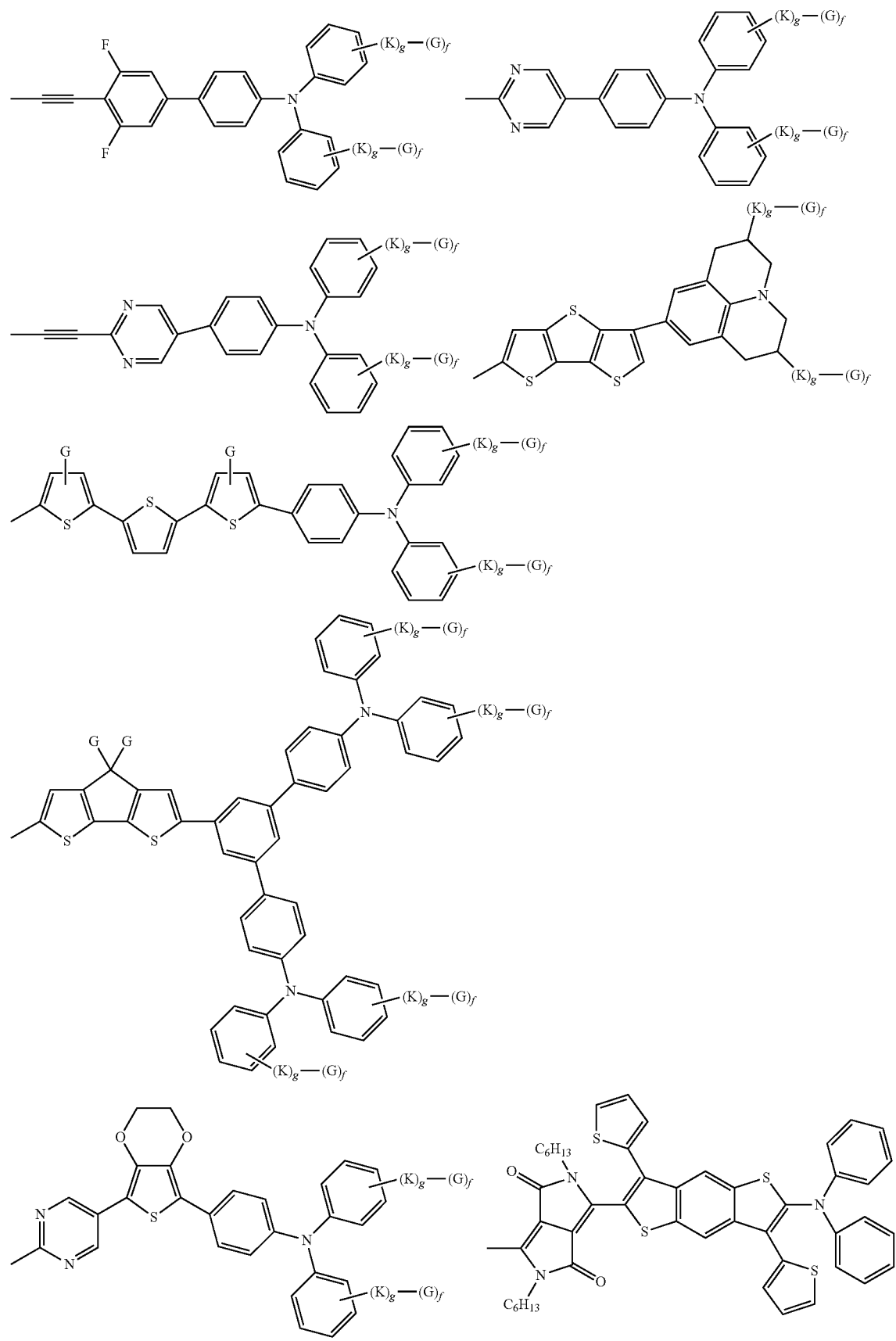

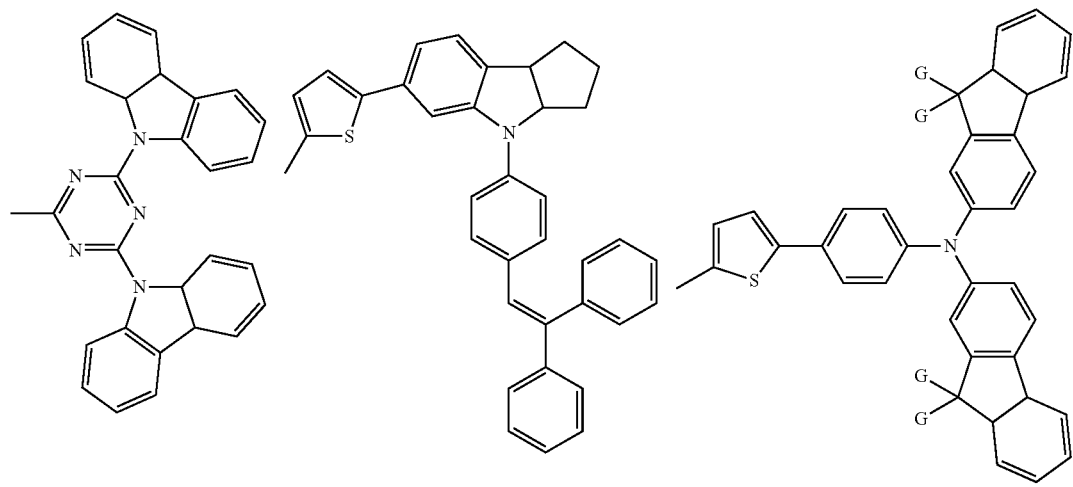
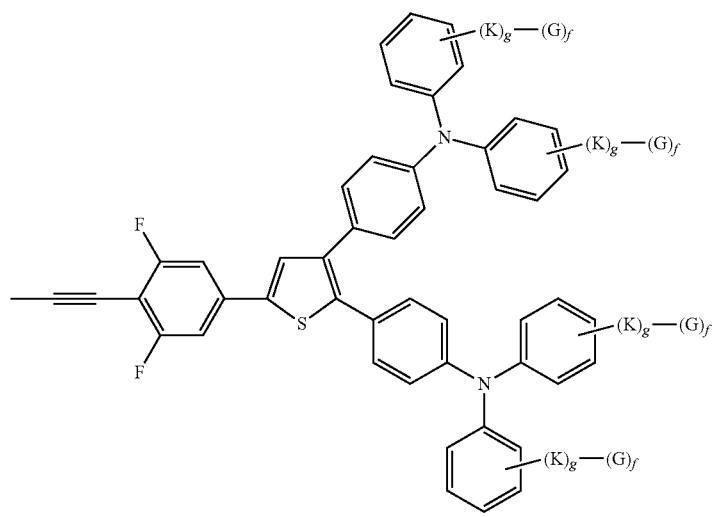
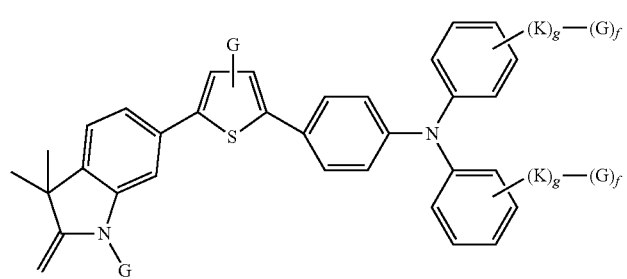

-continued

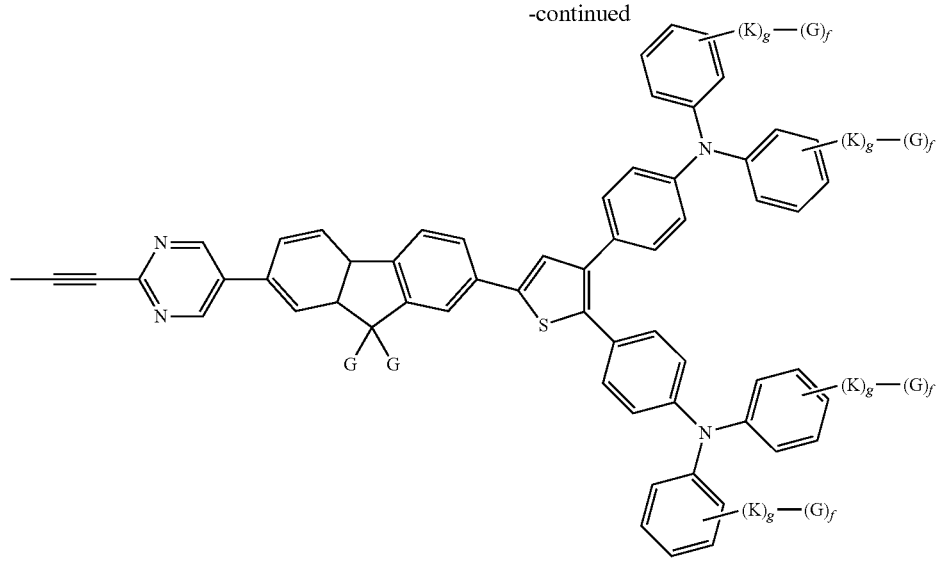

wherein, at each occurrence and independently,
G being any cyclic or acyclic substituted, or straight or branched alkyl,
f=1, 2,
K being selected from O, S, N
g=0, 1, wherein the alkyl, alkoxy, amine, thiole group $-(K)_g-(G)_f$ can be one or more attached to the aryl and heteroaryl rings, in o-, m-, p-position, preferably in o- and/or p-position.

In this embodiment, $A_1$ and $A_2$ each independently can preferably be selected from

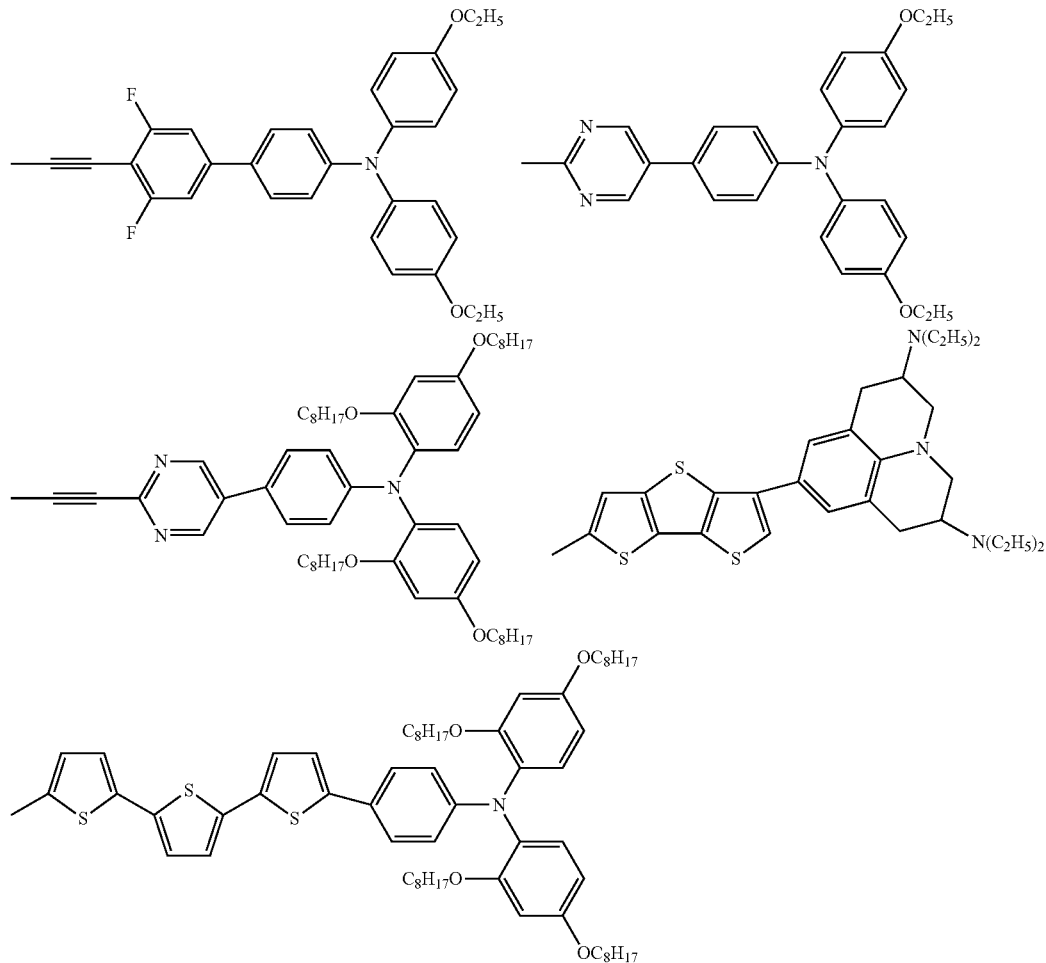

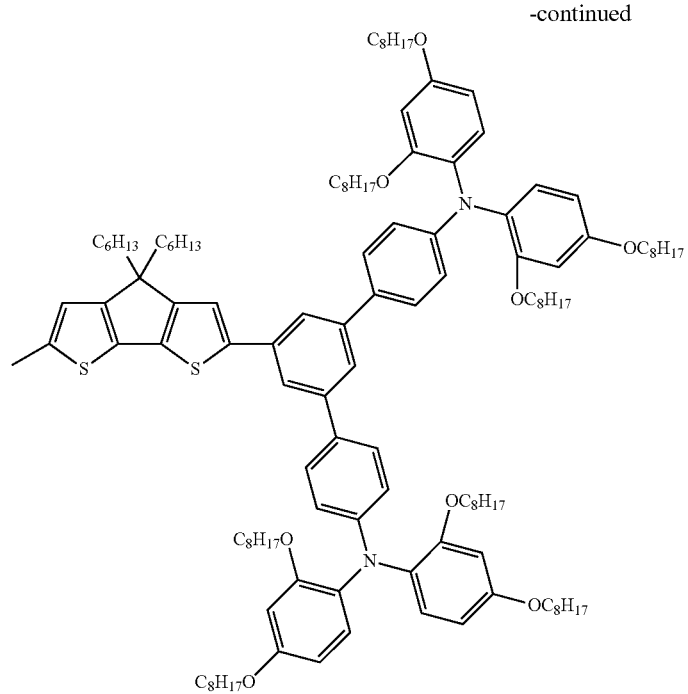
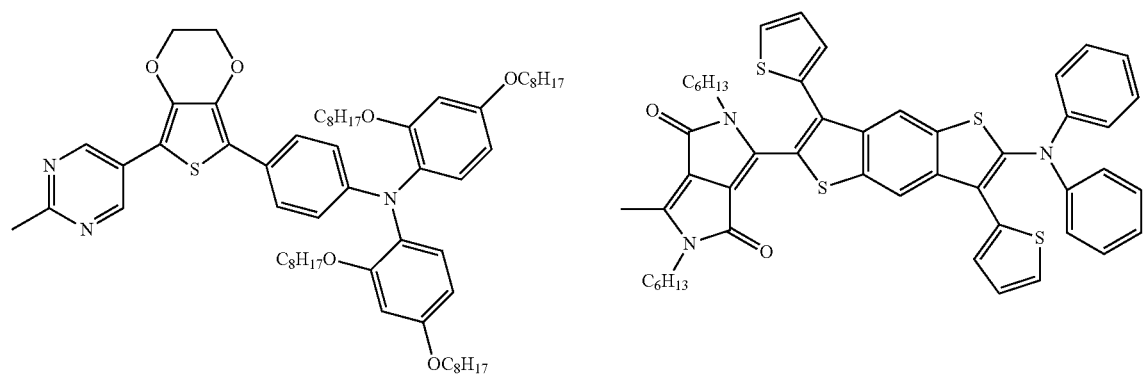
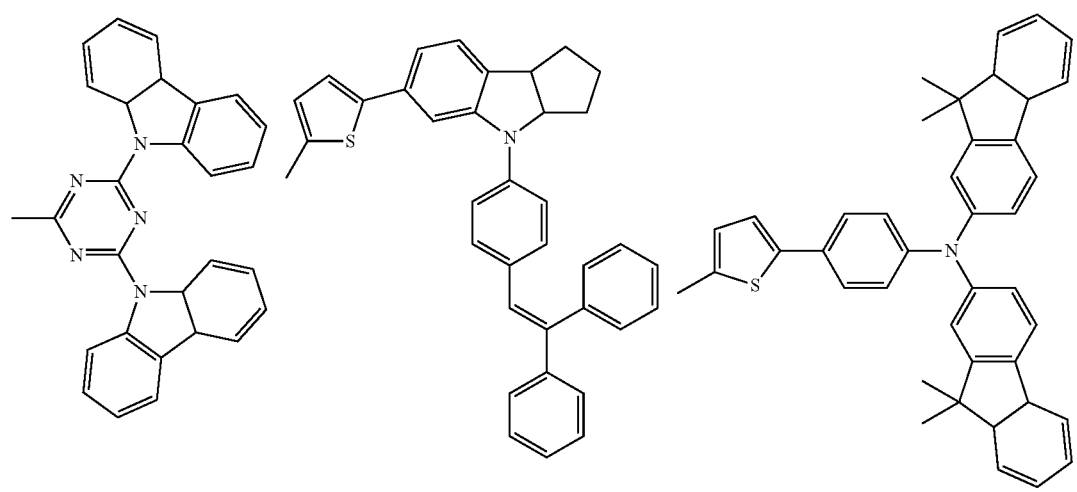

-continued
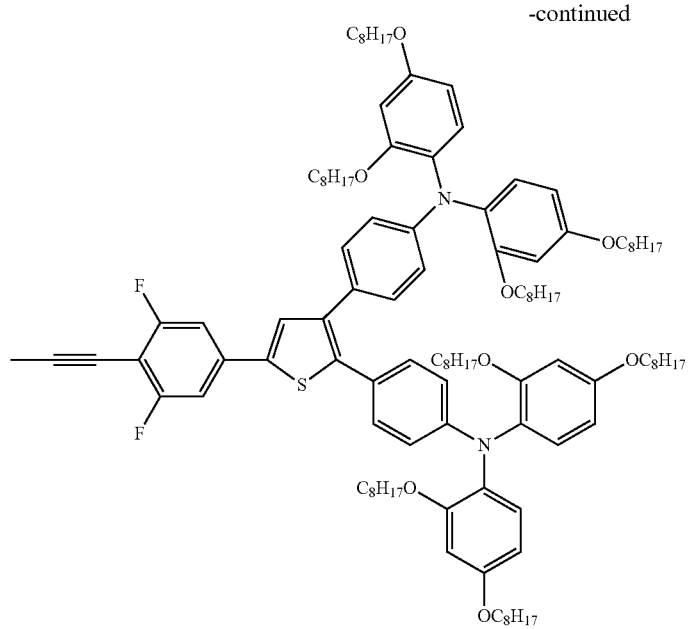
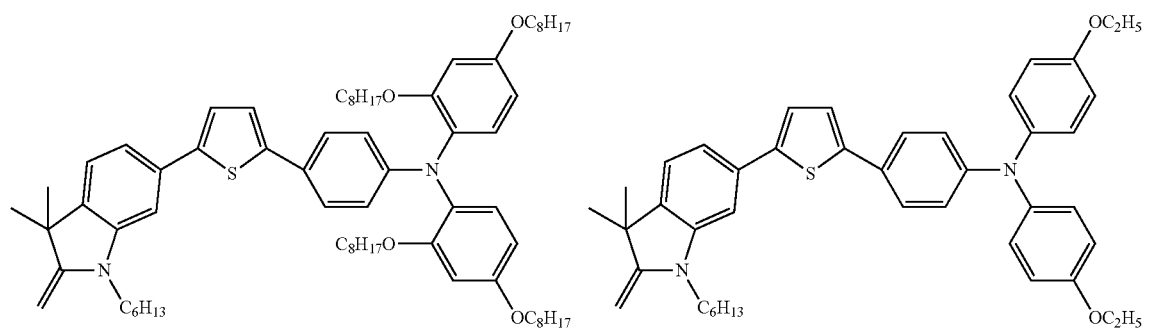
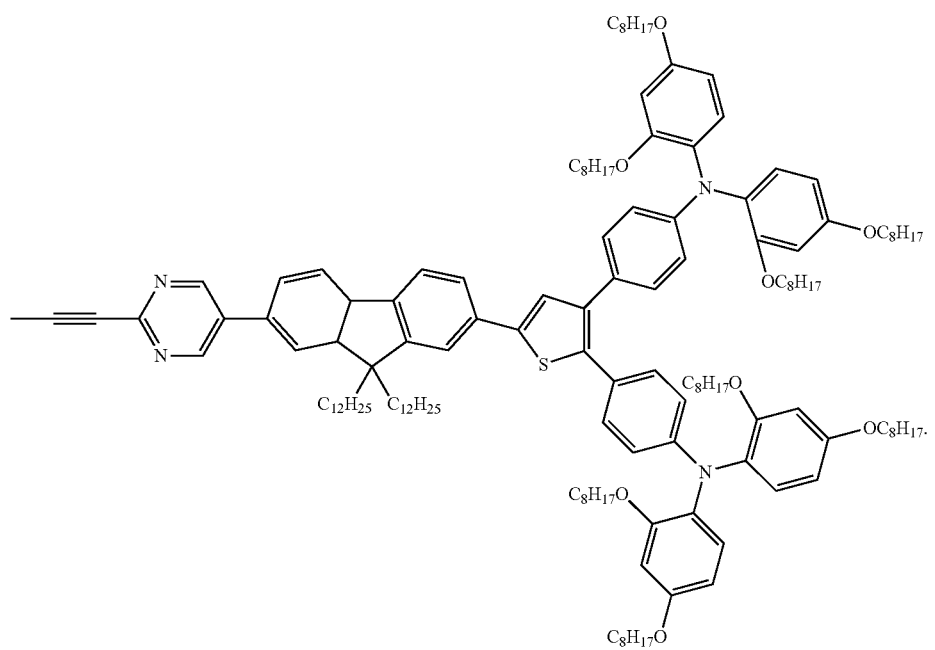

As described above, one compound according to the disclosure can have an influence on more than one of the above described properties of a conducting, semiconducting, or insulating organic or inorganic substrate.

For example, one compound can simultaneously influence work function and light absorption capability of the conducting, semiconducting, or insulating organic or inorganic substrate. For example, one compound can simultaneously influence work function and surface energy and light absorption capability of the conducting, semiconducting, or insulating organic or inorganic substrate.

As described above, at least one compound according to the disclosure can be used for modifying or influencing the work function and the light absorption capability of a conducting, semiconducting, or insulating organic or inorganic substrate.

In one embodiment, at least one compound according to the disclosure can be used for decreasing the work function (shifting the work function towards vacuum level), and improving the light absorption capability of said conducting, semiconducting, or insulating organic or inorganic substrate.

An exemplary compound for this embodiment is

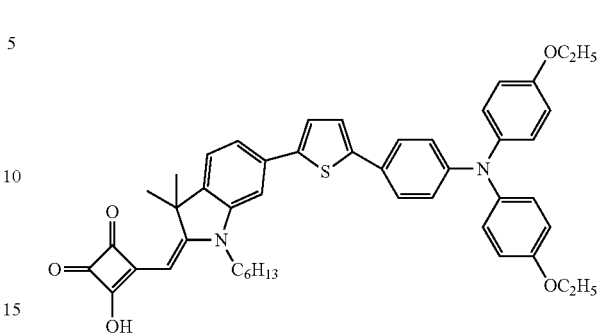

As described above, at least one compound according to the disclosure can be used for modifying or influencing the work function, the surface energy and the light absorption capability of a conducting, semiconducting, or insulating organic or inorganic substrate.

In one embodiment, at least one compound according to the disclosure can be used for decreasing the work function, decreasing the surface energy and improving the light absorption capability of said conducting, semiconducting, or insulating organic or inorganic substrate.

In this embodiment, $A_1$ and/or $A_2$ each independently is preferably selected from

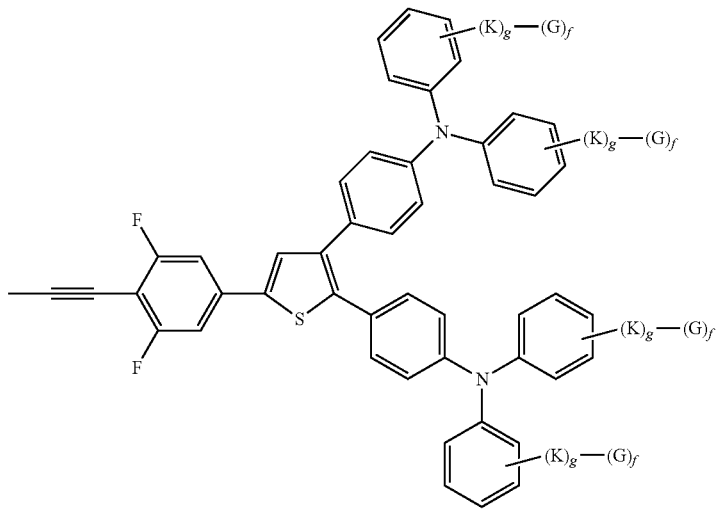

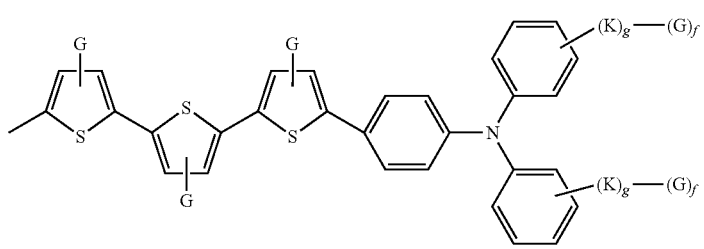

-continued
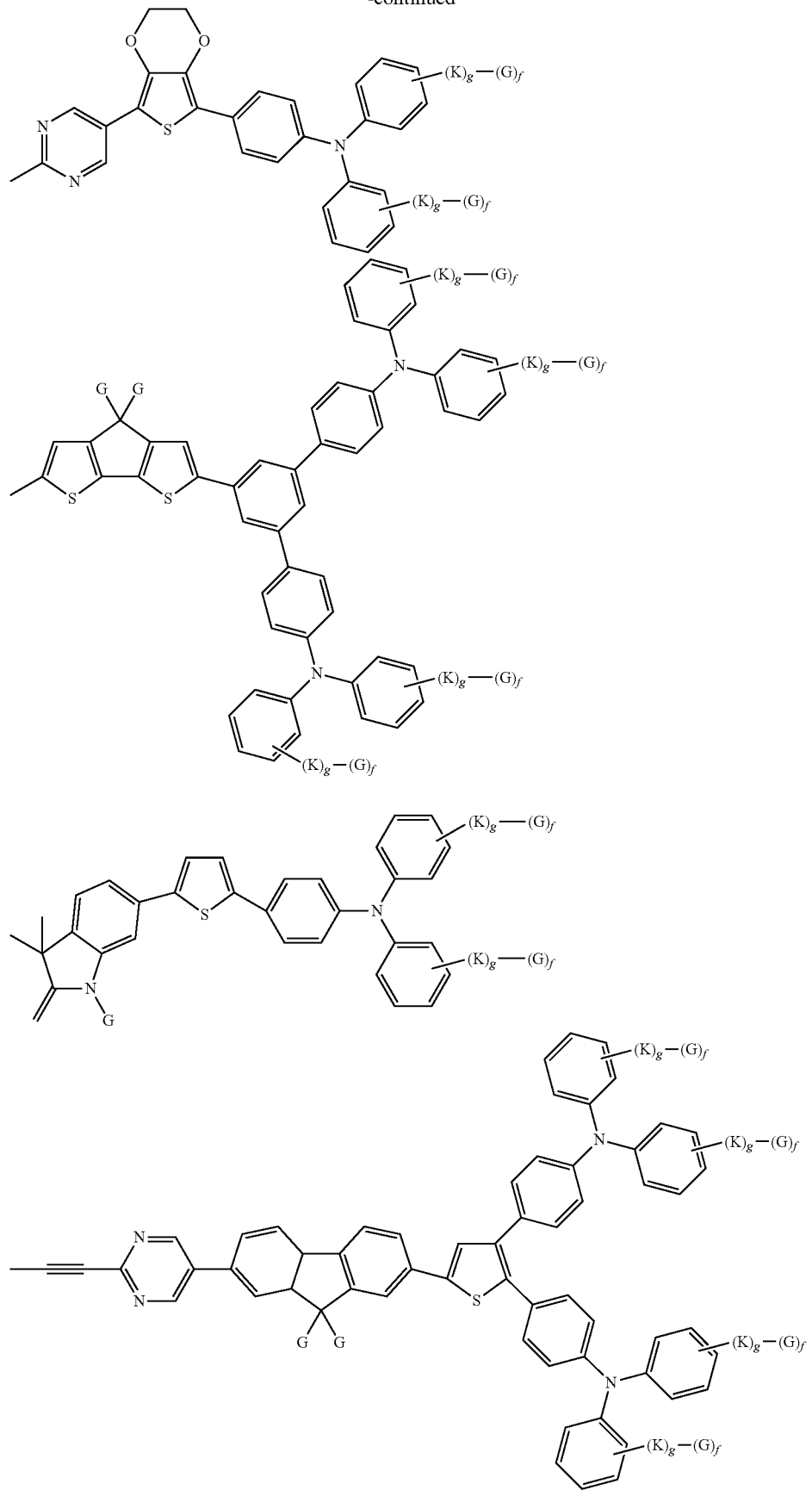

wherein, at each occurrence and independently,
G being any cyclic or acyclic substituted, or straight or branched alkyl,
f=1, 2,
K being selected from O, S, N,
g=0, 1, wherein the alkyl, alkoxy, amine, thiole group —(K)$_g$-(G)$_f$ can be one or more attached to the aryl and heteroaryl rings, in o-, m-, p-position, preferably in o- and/or p-position.

In this embodiment, A$_1$ and/or A$_2$ each independently is more preferably selected from

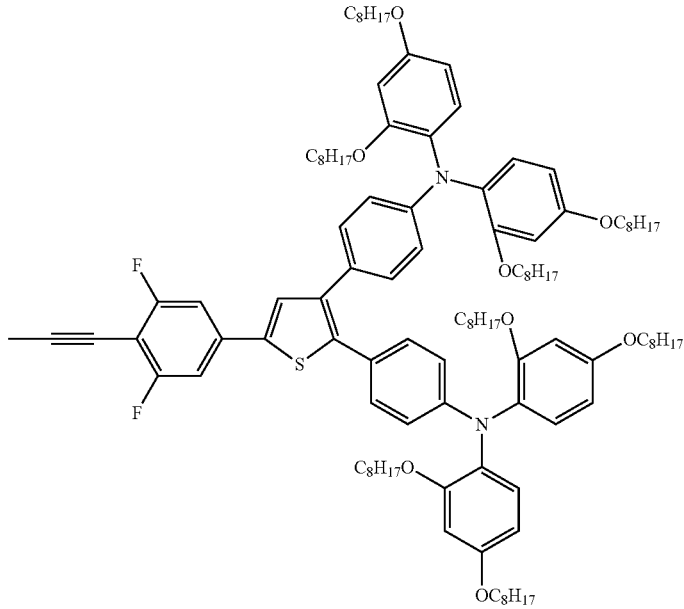

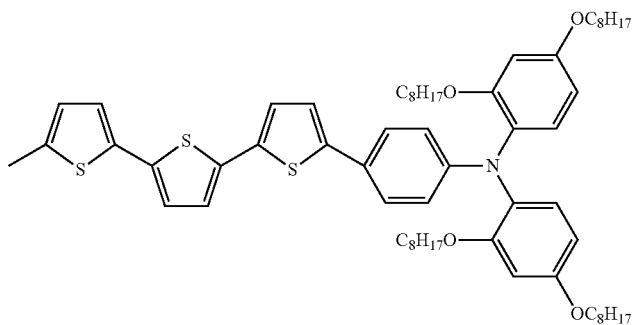

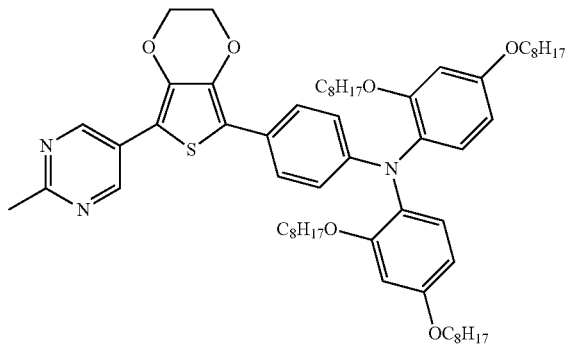

-continued
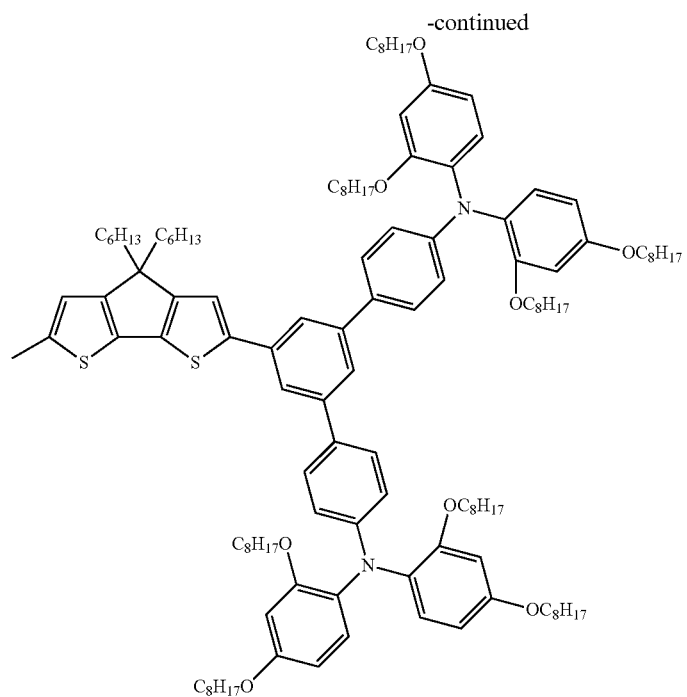
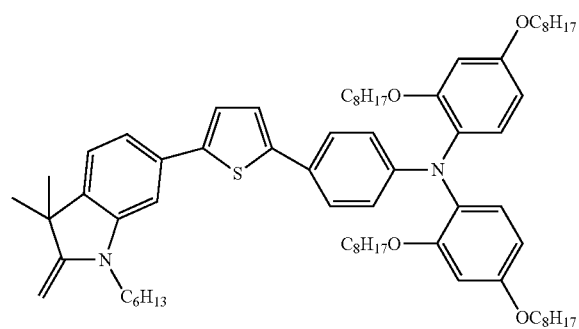
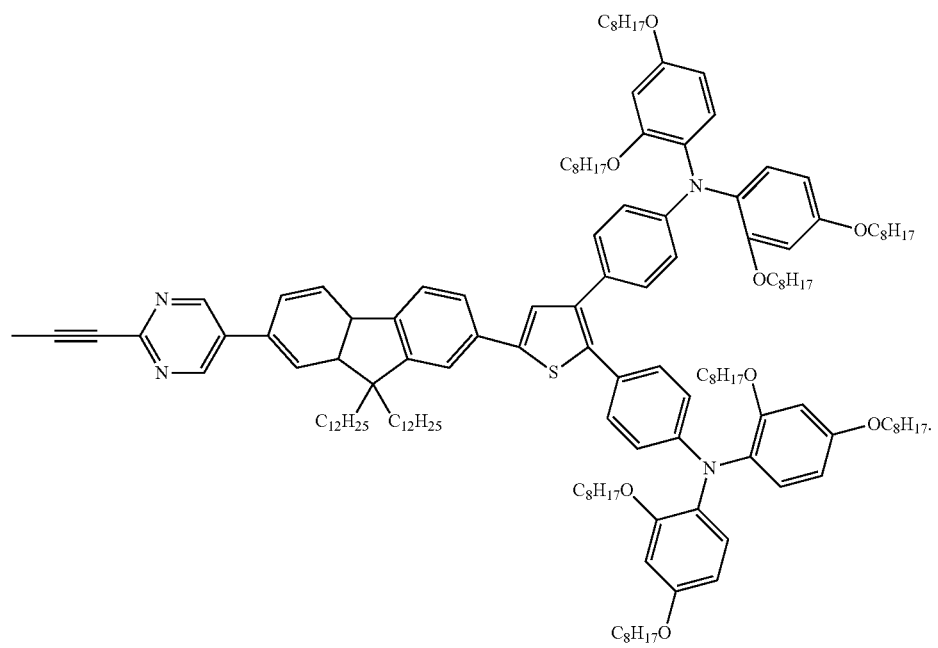

The above compounds positively can be used to modify/influence more than one property of the component/substrate: decreasing work function, decreasing surface energy, improving light absorption capability which is of advantage for photochemical devices, such as DSSC, for increased photovoltage, better wettability with non-volatile or solid state electrolyte, increased photocurrent, respectively.

In one embodiment more than one of the compounds according to the present disclosure is used. In one embodiment, two to ten compounds of the disclosure are used. In one embodiment, two, three, four, five, six, seven, eight, nine or ten compounds of the disclosure are used. Preferably, two or three compounds of the disclosure are used.

In order to modify and/or influence the properties of a conducting, semiconducting or insulating organic or inorganic substrate, one compound according to the disclosure or a mixture of said compounds can be used.

In this embodiment, compounds that modify or influence different properties of the substrate can be combined or mixed.

For example, the combination of different compounds of the disclosure in a mixture could allow the control of the surface energy over a wide range of values, with an independent control over the work function.

In one embodiment, at least two compounds according to the disclosure are used to improve the light absorption capability and at the same time increase the tunneling barrier of a conducting, semiconducting, or insulating organic or inorganic substrate.

In this embodiment, said two compounds are preferably

3

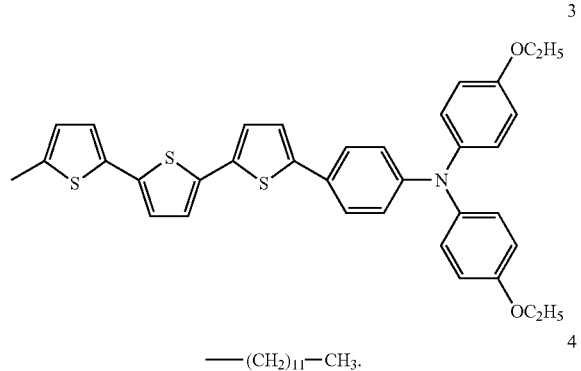

4

In one embodiment, at least two compounds according to the disclosure are used to improve the light absorption capability and at the same time decrease the work function of a conducting, semiconducting, or insulating organic or inorganic substrate.

In this embodiment, said two compounds are preferably

5

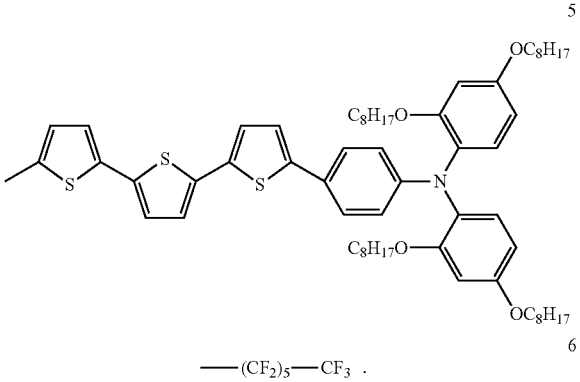

6

The objects of the present disclosure are also solved by an electronic device comprising at least one compound according to the disclosure, wherein, preferably, said device is selected from a light-emitting device, a Schottky barrier diode, a rectifier, a field effect transistor, a photovoltaic device, a photochemical device, a memory device, a sensing device, a display, or a photo-catalytical water splitting device.

The objects of the present disclosure are also solved by an assembly for use in an electronic device, said assembly comprising:

a) a conducting substrate, a semiconducting substrate, or an insulating organic or inorganic substrate, said substrate having a surface, b) a layer of at least one compound, comprising a squaric acid or croconic acid group, on said surface, wherein said layer is covalently attached to said surface via the squaric acid or croconic acid group and wherein said compound, comprising an squaric acid or croconic acid group, is as defined herein (i.e. is a compound according to the present disclosure), and c) an organic layer, an inorganic layer, or an electrolyte layer deposited on said layer.

The layer of b) is preferably a monolayer.

Various physical or chemical deposition methods for step c) are known in the art and include thermal evaporation, spin-coating, stamping, sputtering, atomic layer deposition, physical and chemical vapor deposition, and electroplating.

The objects of the present disclosure are also solved by an assembly for use in an electronic device, said assembly comprising:

a) a first substrate being a conducting substrate, a semiconducting substrate, or an insulating organic or inorganic substrate, said first substrate having a surface being the first surface, b) a first layer of at least one compound, comprising a squaric acid or croconic acid group, on said first surface, wherein said first layer is covalently attached to said first surface via the squaric acid or croconic acid group and wherein said compound, comprising an squaric acid or croconic acid group, is as defined herein (i.e. is a compound according to the present disclosure), and c) a second substrate being a conducting substrate, a semiconducting substrate, or an insulating organic or inorganic substrate, said second substrate having a surface being the second surface, d) a second layer of at least one compound, comprising a squaric acid or croconic acid group, on said second surface, wherein said second layer is covalently attached to said second surface via the squaric acid or croconic acid group and wherein said compound, comprising an squaric acid or croconic acid group, i is as defined herein (i.e. is a compound according to the present disclosure).

The compound of b) and d) can be the same or different.

The first substrate and the second substrate can be the same or different.

Preferably, the first and second substrate do not contact each other.

Preferably, the first and second layer (i) can be in contact with each other or (ii) another layer is in between said first and second layer.

The first and second layer is preferably a monolayer.

The objects of the present disclosure are also solved by an electronic device comprising the assembly according to the present disclosure, wherein, preferably, said device is selected from a light-emitting device, a Schottky barrier diode, a rectifier, a field effect transistor, a photovoltaic device, a photochemical device, a memory device, a sensing device, a display, or a photo-catalytical water splitting device.

The objects of the present disclosure are also solved by a method of modifying the work function, the surface energy, the tunnelling barrier and/or the light absorption capability of a conducting, semiconducting, or insulating organic or inorganic substrate, said method comprising the steps:

a) adsorbing a compound as defined in the present disclosure on a surface of said conducting, semiconducting, or insulating organic or inorganic substrate, said adsorption being as defined being as defined above, and b) depositing an organic layer, an inorganic layer, or an electrolyte layer on said layer.

As used herein, the term "substrate" is used is meant to refer to a solid, especially an organic or inorganic substance, with a surface. Such a substrate may also be referred to herein as a "component" or "layer" in an electronic device.

As used herein, the term "work function" is meant to refer to the minimum work required for extracting an electron from the vacuum level of a conducting phase and placing it into vacuum just beyond the influence of electrostatic forces, i.e. into the so-called vacuum level.

As used herein, the term "modifying" or "influencing" a work function of a substrate, is meant to refer to an increase or decrease in magnitude of said work function, or to relative shifts in the vacuum levels of two or more condensed phases, such as, for example, between the gate electrode and channel of a field-effect transistor.

As used herein, the term "surface energy" is the interaction between the forces of cohesion and the forces of adhesion which determines whether or not wetting. Water is polar and has a rather high surface energy by nature. A higher surface energy of surface or modified surface is indicated by increased hydrophilicity resulting in smaller contact angles of a drop of water on it. If the surface or modified surface is more hydrophobic then the contact angle of a drop of water will be larger and the surface energy lower. As used herein, the term "surface energy" will influence and define adhesion, covering or contact between surfaces of two materials determining the interaction of the two materials at their interface.

As used herein, the term "tunnelling barrier" is the ability or non-ability for charge transport by tunneling through a junction formed by two materials, generally one material being the drain, the second one the source.

As used herein, the term "light absorption capability" is the physical property of a material to harvest/collect/absorb as much light as possible, preferably in a very broad range of a solar spectrum. In photochemical electronic devices photons (light) are captured and transformed to electrons, the efficiency of the device being determined by that conversion. As much photons can be captured as much electrons will be produced.

"Push-pull" compounds or systems are ones in which electron-accepting (EA) and electron-donating (ED) groups interact via a pi-conjugated system such that a partial intermolecular charge transfer occurs from the donor group to the acceptor group through the conjugated path. Intramolecular charge transfer induces an asymmetric polarization of the ground state and can provide push-pull compounds/ systems with large ground-state dipole moments. A number of the dipolar compounds provided as examples in the present disclosure can be considered as push-pull type compounds/systems, where a squaric acid or croconic acid group is EA group, while D appended to it is the ED group.

Generally, such "Push-pull" compounds show a good light absorption capability due to the extended pi-conjugated system.

The term "anchoring group", as used herein, is meant to refer to any functional group that allows a coupling of the entity to which such anchoring group belongs, to a surface, for example the surface of a nanoporous semiconductor layer within a solar cell. The adsorption can occur chemically (=chemisorption) or physically (=physisorption). As used herein, in the context of a layer of the compounds of the disclosure, such adsorption is preferably chemical. Chemisorption refers to the formation of a chemical bond between the adsorbate and the substrate.

The squaric acid or croconic acid group of the compounds of the present disclosure enables a stable adsorption by covalent coupling (chemisorption) onto surface of a conducting, semiconducting or insulating organic or inorganic substrate.

A compound is referred to as being "chemisorbed" to a layer or surface, if the compound is covalently coupled thereto.

The inventors have surprisingly found that the squaric or croconic acid compounds (SA or CA compounds) disclosed in the present disclosure can be used for an improved charge transfer and, thus, improved performance of electronic devices by effecting and controlling one or more of the physical and photo-physical properties of the surfaces of conducting, semiconducting or insulating organic or inorganic substrates.

Depending on the nature of D, especially of its dipole moment, size, hydrophilicity, charge, orientation, aromaticity, the compounds of the present disclosure will have effect on more than one physical property of a surface (of the substrate they are attached to).

The compounds of the present disclosure will influence
1) work function;
2) surface energy;
3) tunnelling barrier; and/or
4) light absorption capability.

In particular, when the compound according to the present disclosure is a not a fully conjugated system, it will effect only on property 1) and/or 2) and/or 3). When the compound according to the present disclosure is a conjugated system it will have an effect on properties 1) and/or 2) and/or 3) as well as 4).

The inventors have found a reliable and cost-effective method to control the interface of two components and to tune the physical and photo-physical properties of a conducting, semiconducting or insulating organic or inorganic substrate to which an adsorbent (i.e. a SA or CA compound according to the disclosure) is attached. The physical and photo-physical properties of the substrates can be controlled/ tuned so as to performance of the electronic and electrochemical device is improved. By varying moiety D the interface and physical/photophysical properties of the component/substrate, such as light absorption properties, work function, tunneling barriers and the interfaces of the components, such as energy levels, surface free energies are easily adjusted.

Molecular adsorbents, the SA and CA compounds as described herein, can easily be prepared, and they have good thermal and chemical stability. The adsorption on most surfaces is stable due to covalent bonding, performance of the device is stable over time and under different conditions (e.g. high temperature and humidity).

The adsorption on the surface occurs by exposing the conducting, semiconducting or insulating organic or inorganic substrate to a solution containing the SA or CA compound(s) or by evaporating or spin-coating the solution containing the SA or CA compound(s) on the surface or by thermal evaporating or sublimating the SA or CA compound(s) on the surface, or by doctor blading or drop casting of a solution or matrix containing the SA or CA compound(s) on the surface or by doctor blading or drop casting the SA or CA compound(s) on the surface.

In order to control the properties of a conducting, semiconducting or insulating organic or inorganic substrate, one compound according to the disclosure or a mixture of said compounds can be used.

As disclosed herein, by adsorption of the SA or CA compounds on the surface of a conducting, semiconducting or insulating organic or inorganic substrate, the physical and photo-physical properties, such as its energy level, light absorption property, surface energy of the conducting, semiconducting or insulating organic or inorganic substrate are modified.

The inventors have surprisingly found that by rational structure design of the SA or CA compounds more than one physical or photo-physical properties of the component(s)/substrate(s) can be addressed and tuned at once so as to improve electronic device performance. So for example in case of a dye-sensitized solar cell: by adsorbing an appropriate SA or CA compound according to present disclosure the light harvesting capability of semiconductor is increased resulting in high photocurrent and at the same time its work function is shifted towards vacuum level resulting in high photovoltage. All overall the adsorption of the SA or CA compound leading to higher efficiency of the device.

BRIEF DESCRIPTION OF THE DRAWINGS

In the following, reference is made to the figures, wherein.

Depending of dipole moment of the adsorbent (sensitizer dye or co-adsorbent) the work function (conduction band edge CB) of semiconductor is shifted. Voc is determined by the difference in the quasi-Fermi level of $TiO_2$ and redox of the electrolyte DSSC; the shift in work function of semiconductor has a direct influence on Voc and efficiency of the DSSC.

Figure 4:
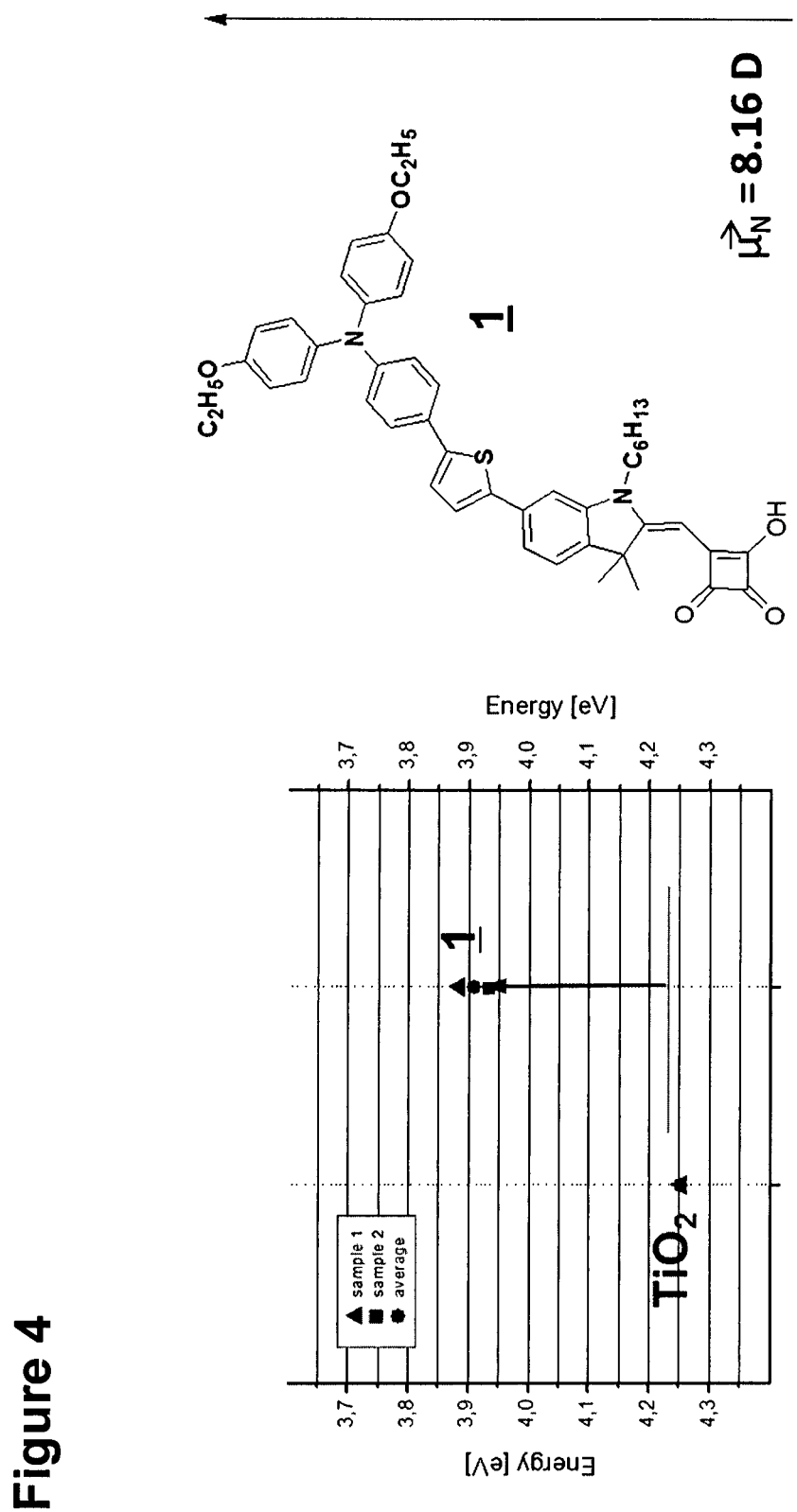

FIG. 4 shows the work function shift of a $TiO_2$ substrate on which an exemplary compound according to the disclosure is anchored.

Figure 5:
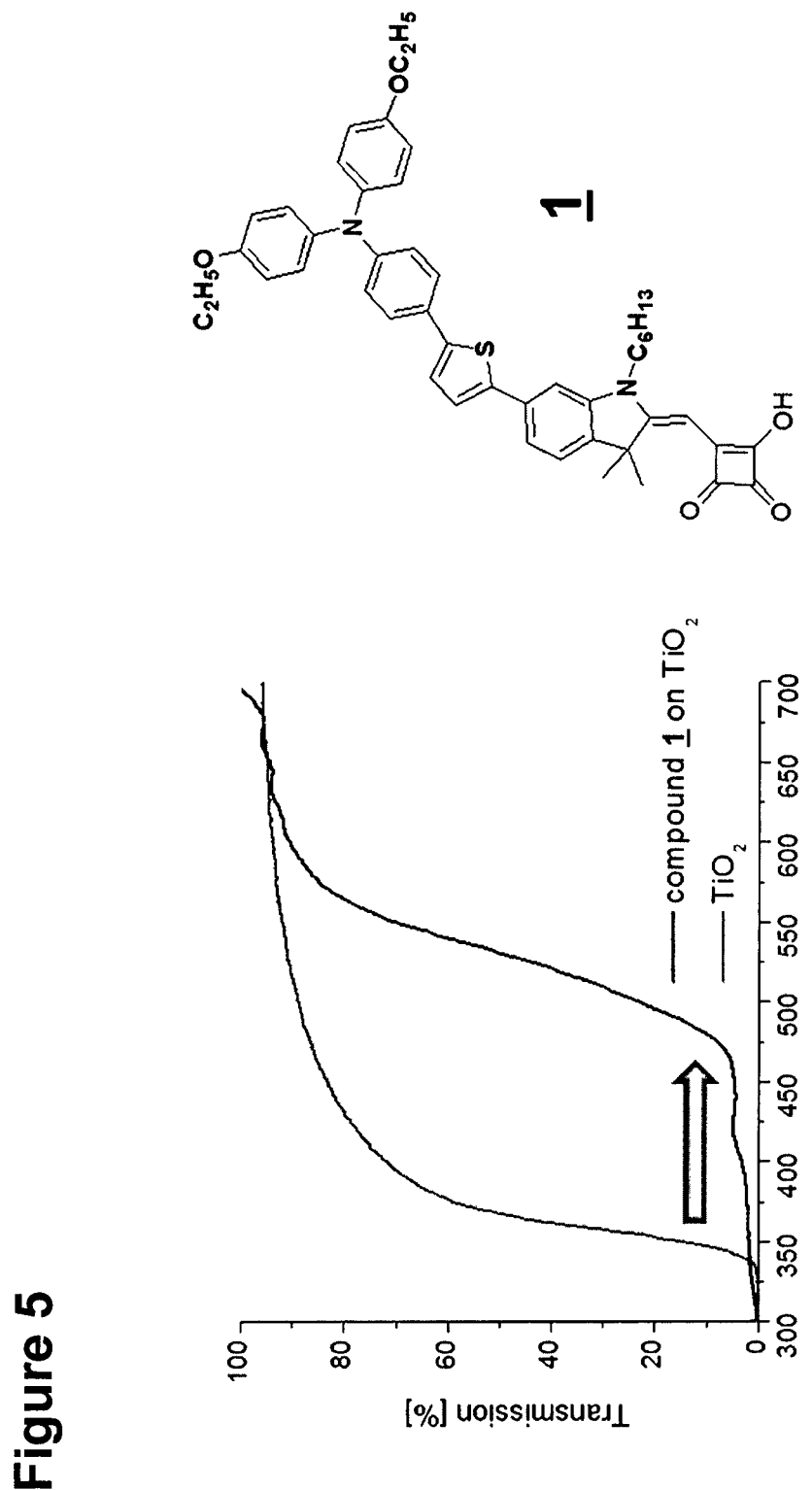

FIG. 5 shows the light absorption capability of a $TiO_2$ substrate on which an exemplary compound according to the disclosure is anchored.

Figure 6:
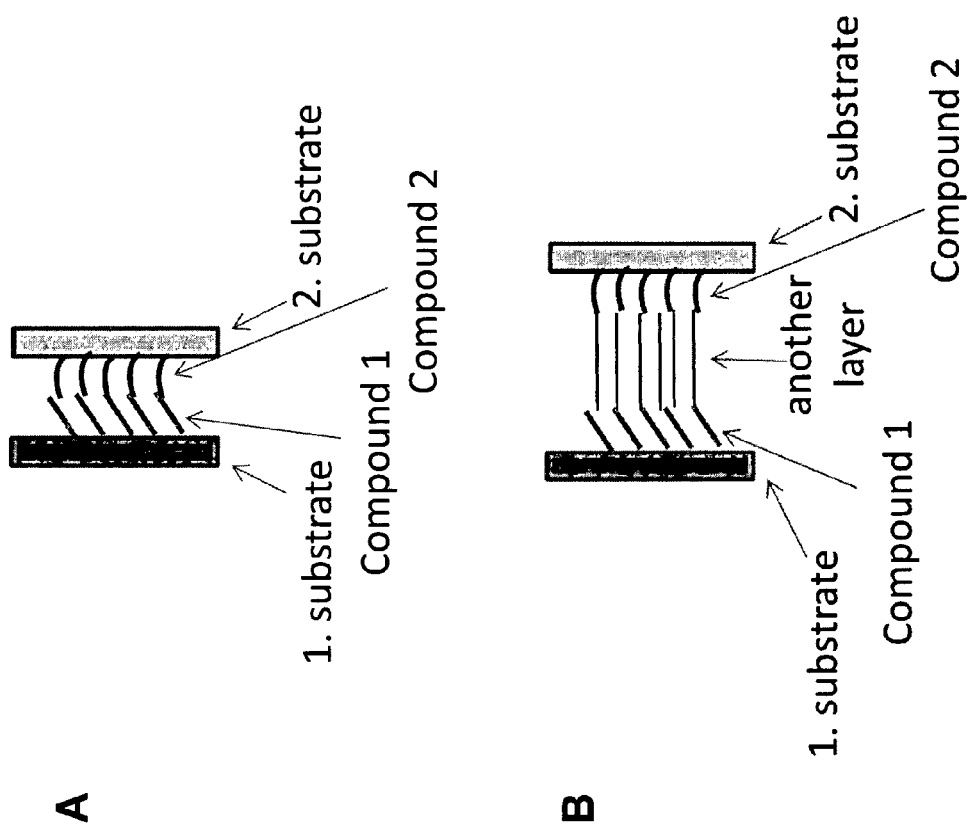

FIG. 6 shows exemplary assemblies comprising a first and a second substrate and a first and a second layer of compound(s) of the present disclosure which are anchored to the respective substrate.

For example, by such a device a junction between two substrates is formed.

DETAILED DESCRIPTION OF THE EMBODIMENTS

The invention will now be further described by reference to the following examples which are given to illustrate, not to limit the present disclosure.

EXAMPLES

Example 1

Figure 1E:
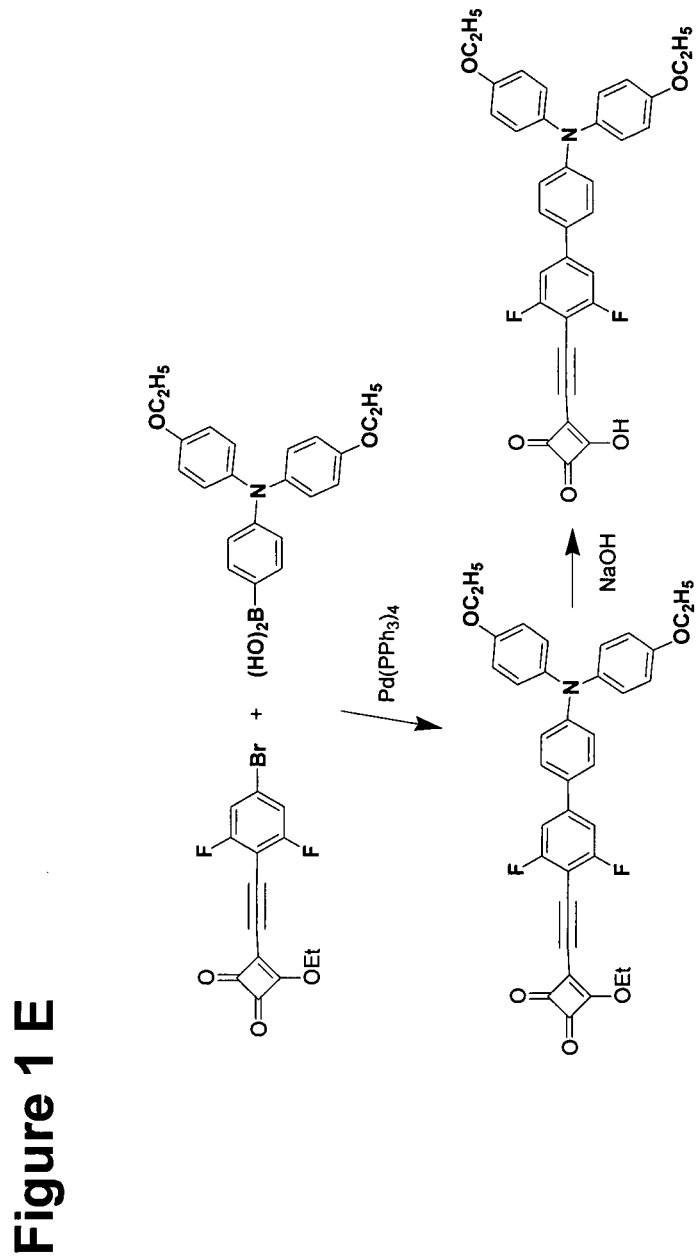
FIG. 1 shows exemplary synthesis routes for exemplary compounds of the disclosure.
Figure 2:
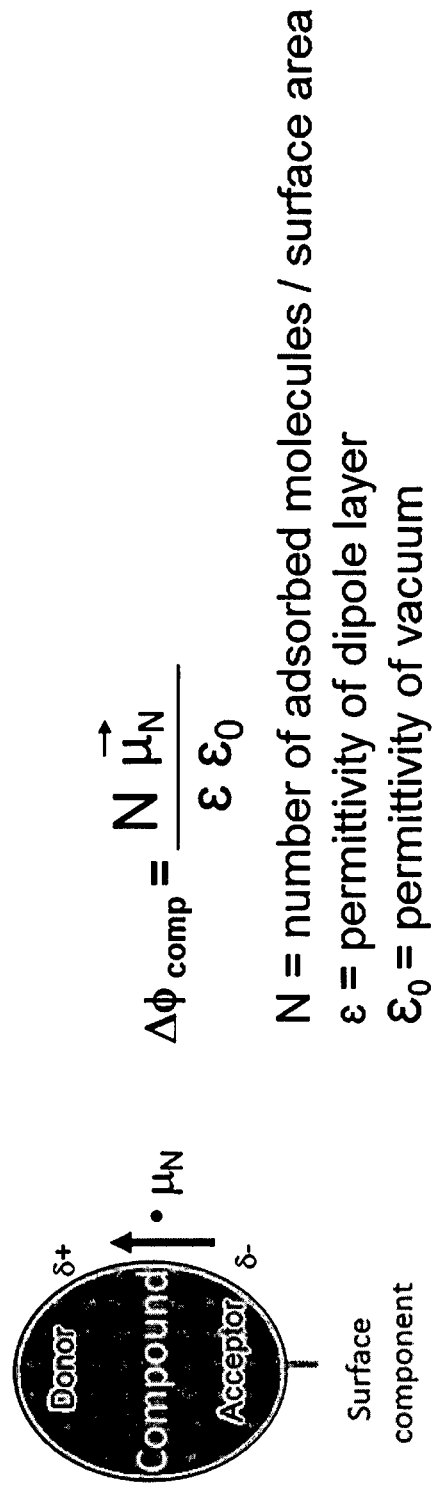
FIG. 2 shows how the work function of a component is shifted by a compound of the disclosure anchored to its surface due to dipole moment of the compound of the disclosure.
Figure 3:
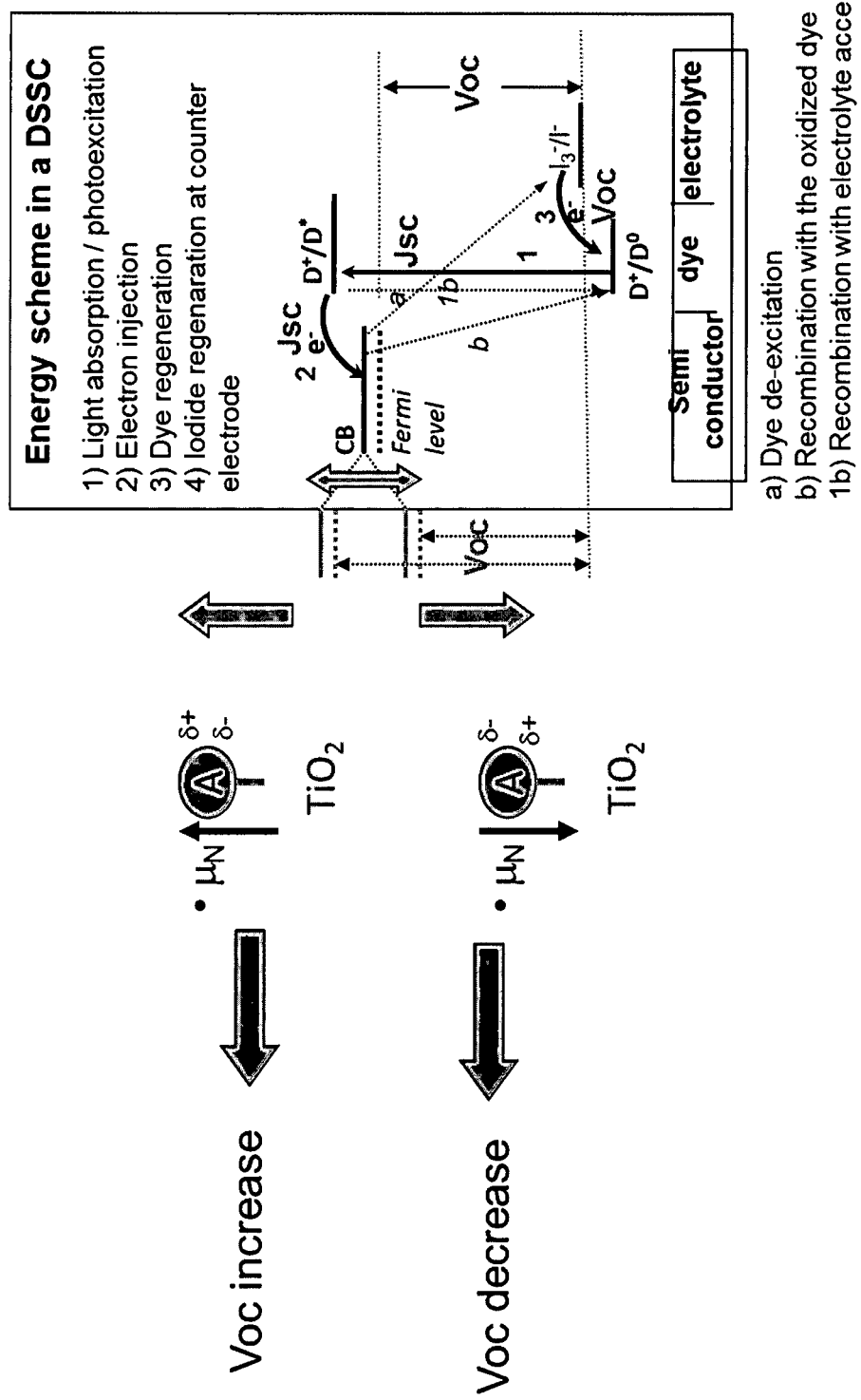
FIG. 3 shows an energy scheme of a DSSC with main components of a semiconductor to which an sensitizer dye is attached and electrolyte (conventional electrolyte being I3-/I-redox pair).

FIGS. 1 A to E show examples of synthesis routes showing the structural design and functionalization of exemplary compounds of the disclosure.

Example 2

Results for tests of compound 1, an exemplary compound of the disclosure, are presented in FIGS. 4 and 5. As can be seen compound 1 modifies the work function as well as the light absorption capability of a $TiO_2$ substrate.

FIG. 4 shows the work function shift (0.3 eV) of $TiO_2$ component when compound 1 is attached to its surface. The work function were determined by Kelvin Probe method by measuring 2 samples, respectively.

The work function shift is due to the dipole moment vector of compound 1 directed away from surface which was calculated to be 8.16 D.

FIG. 5 shows the improvement of light absorption capability of a $TiO_2$ substrate by anchoring compound 1 on its surface. Depicted are the transmission spectrum of $TiO_2$ substrate alone (left graph) and for comparison the transmission spectrum of $TiO_2$ modified by compound 1 (right graph). While $TiO_2$ alone is capable of adsorbing light only up to 350 nm, when compound 1 is attached light up to about 500 nm is adsorbed.

Example 3

Given is an example of a mixture of two compounds of the disclosure to improve light absorption capability of the semiconductor (3) and at the same time increase tunneling barrier (4) from $TiO_2$ to the electrolyte so as to suppress recombination which is concurrent process in a DSSC.

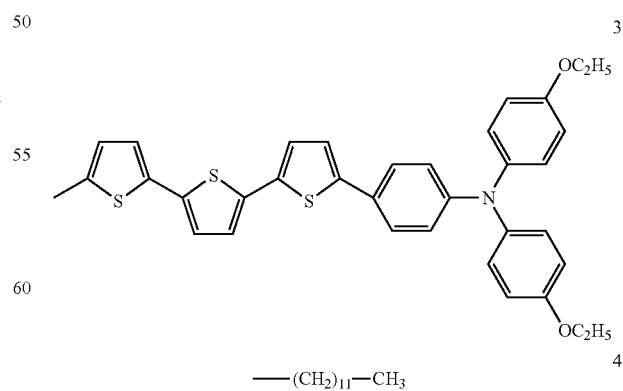

Given is an example of a mixture of two compounds of the disclosure to improve light absorption capability of the semiconductor (5) and at the same time shifting work function to higher values away from vacuum level (6).

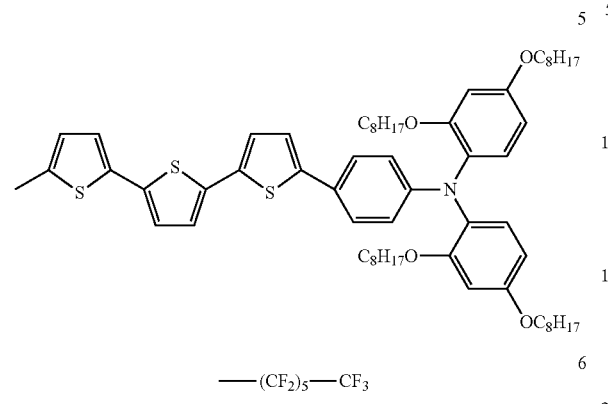

The features of the present disclosure disclosed in the specification, the claims and/or in the accompanying drawings may, both separately and in any combination thereof, be material for realizing the disclosure in various forms thereof.

The present application claims priority to European Patent Application 12 167 017.8, filed in the European Patent Office on May 7, 2012, the entire contents of which being incorporated herein by reference.

The invention claimed is:

1. A compound, comprising a squaric acid or croconic acid group as anchoring group, said compound represented by formula (2):

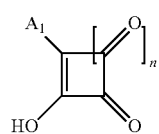

wherein, in formula (2), n is 1 or 2,
wherein $A_1$ is selected from the following moieties

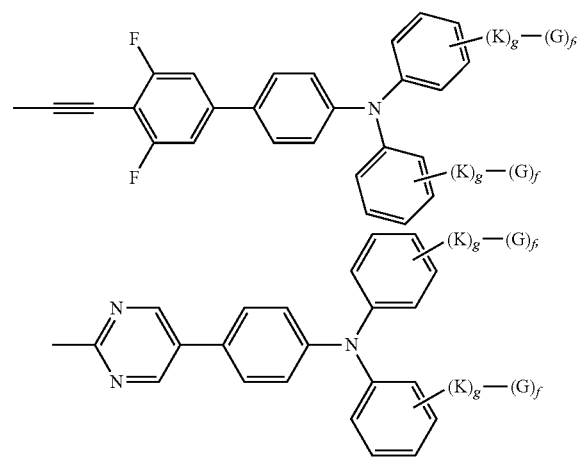

-continued

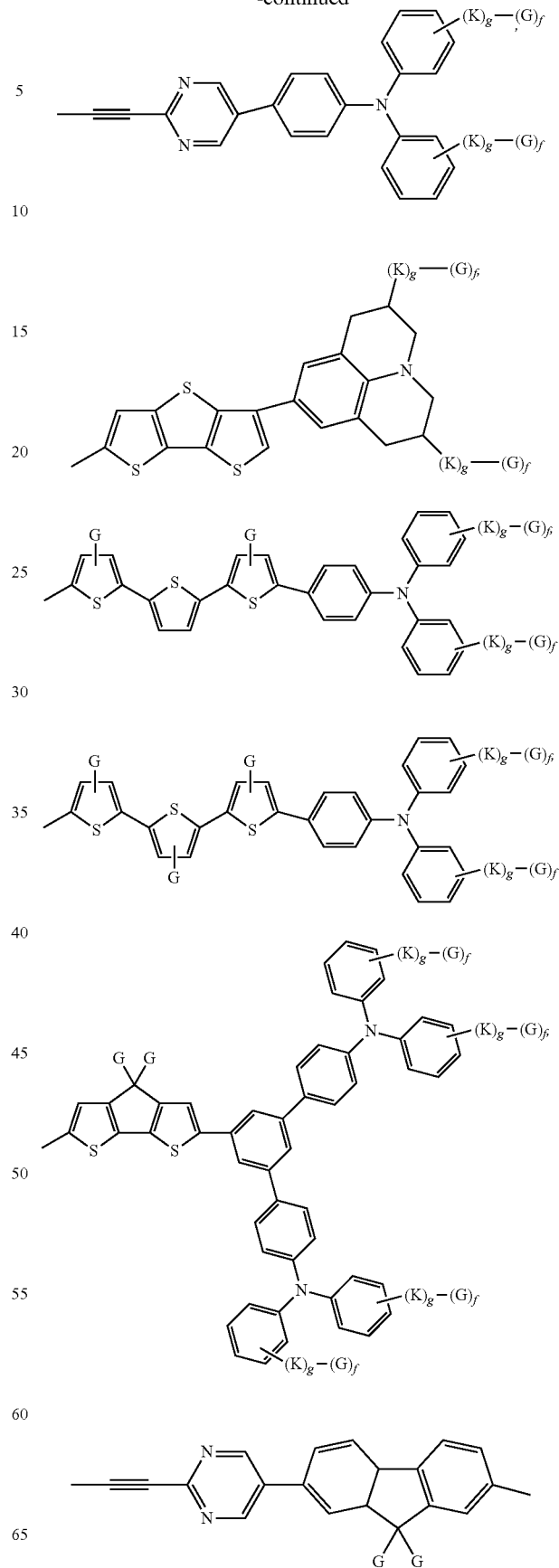

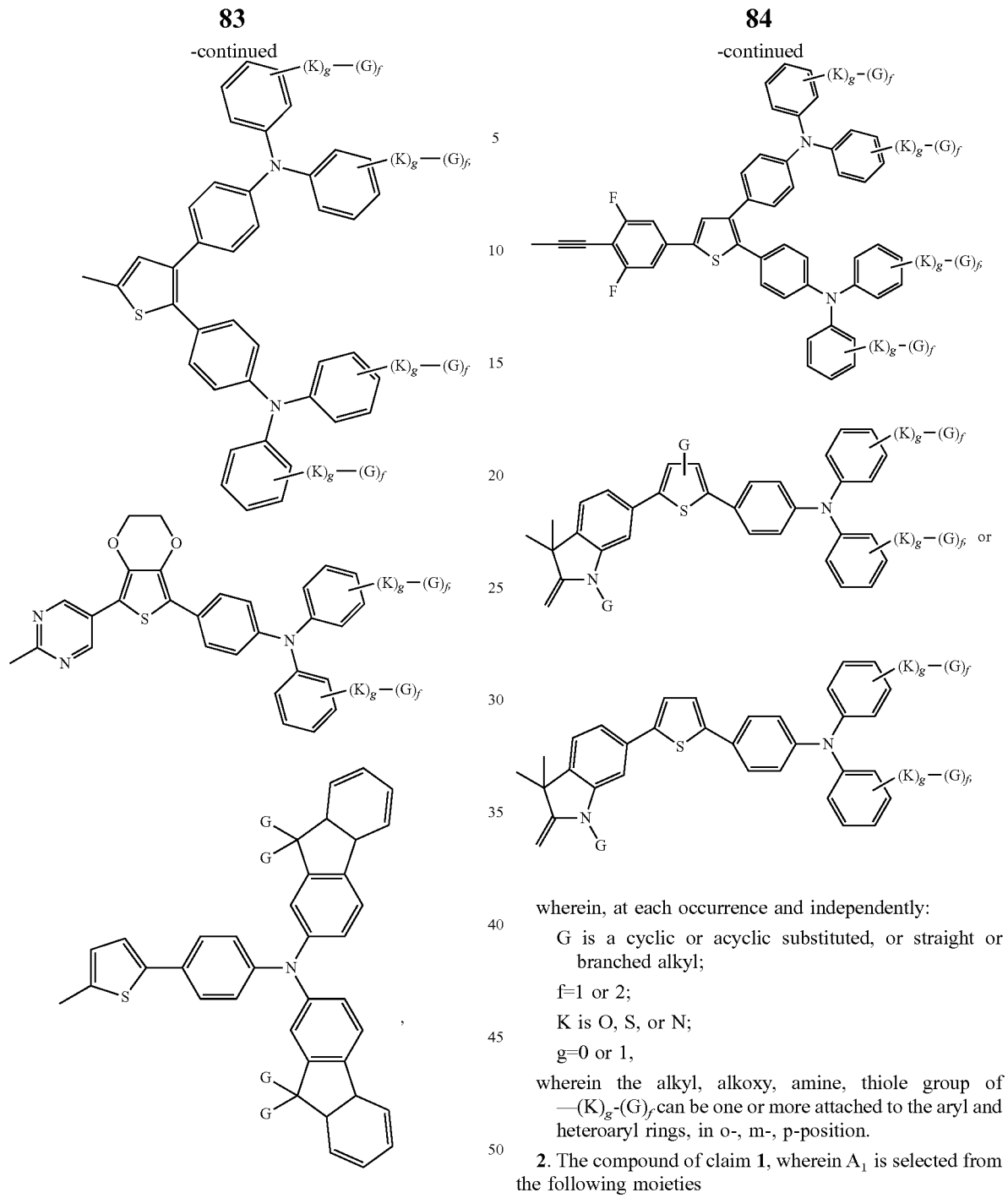
wherein, at each occurrence and independently:
G is a cyclic or acyclic substituted, or straight or branched alkyl;
f=1 or 2;
K is O, S, or N;
g=0 or 1,
wherein the alkyl, alkoxy, amine, thiole group of —(K)$_g$-(G)$_f$ can be one or more attached to the aryl and heteroaryl rings, in o-, m-, p-position.
2. The compound of claim 1, wherein A$_1$ is selected from the following moieties
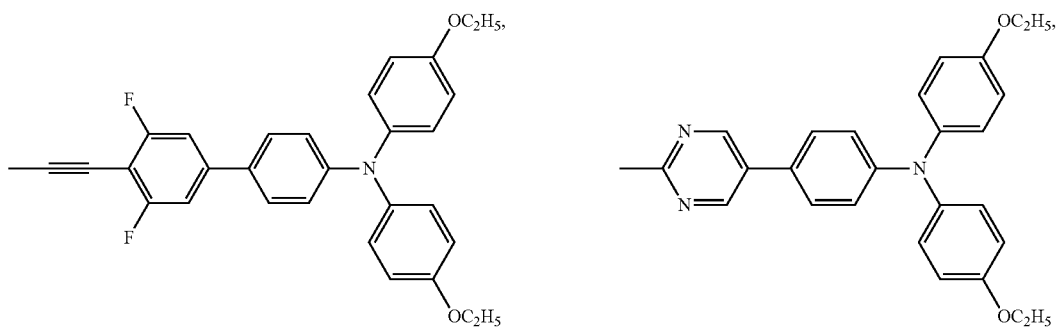

-continued
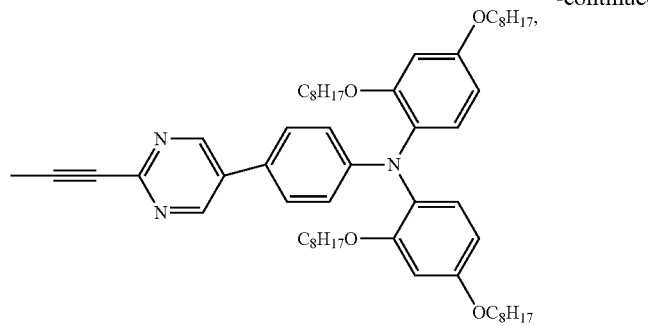
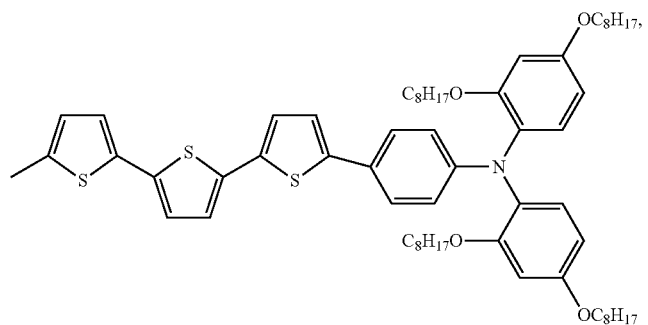
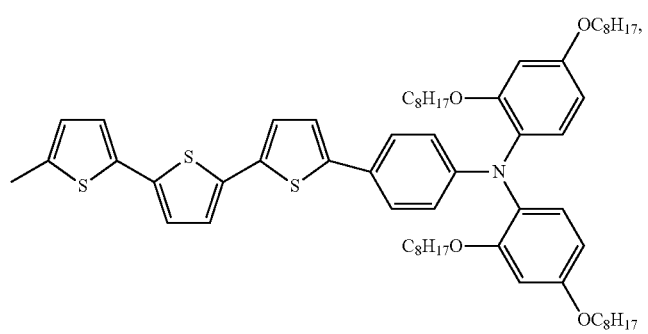
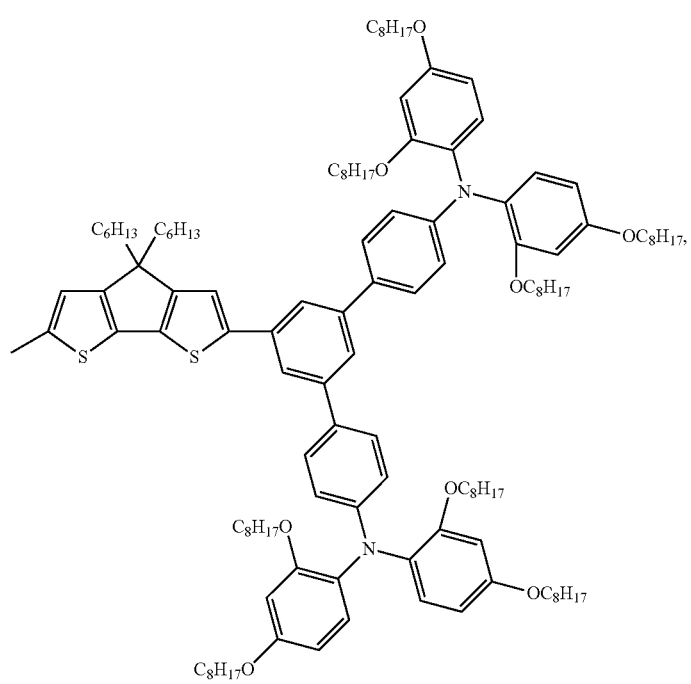

-continued
87
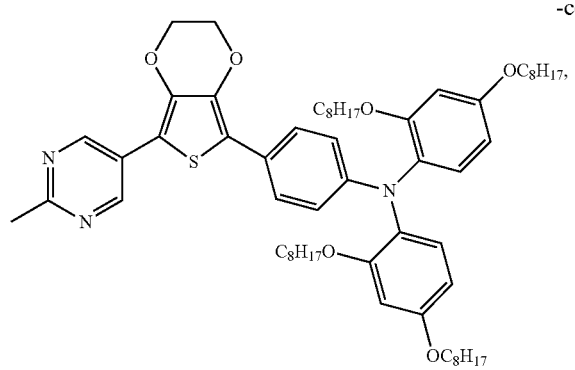
88
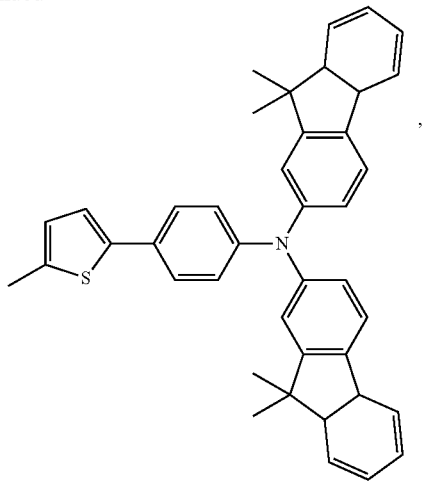
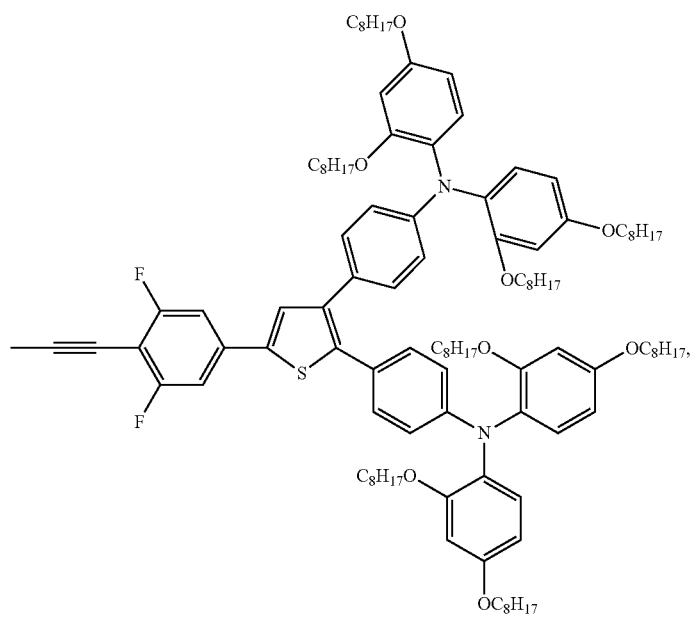
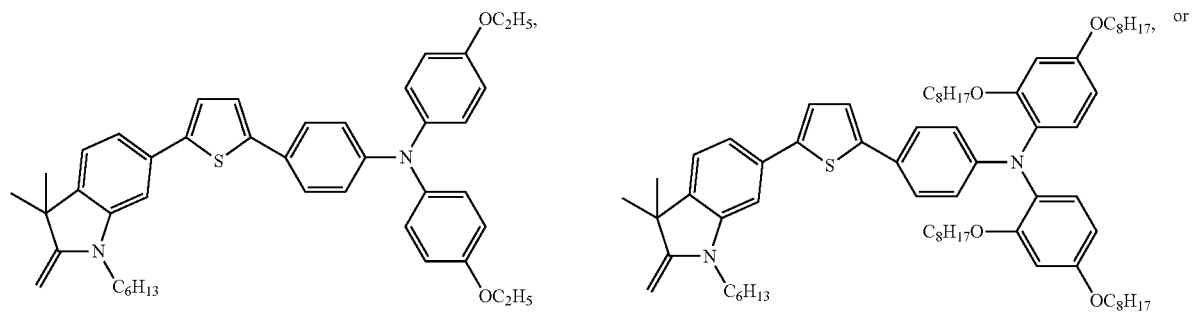

-continued
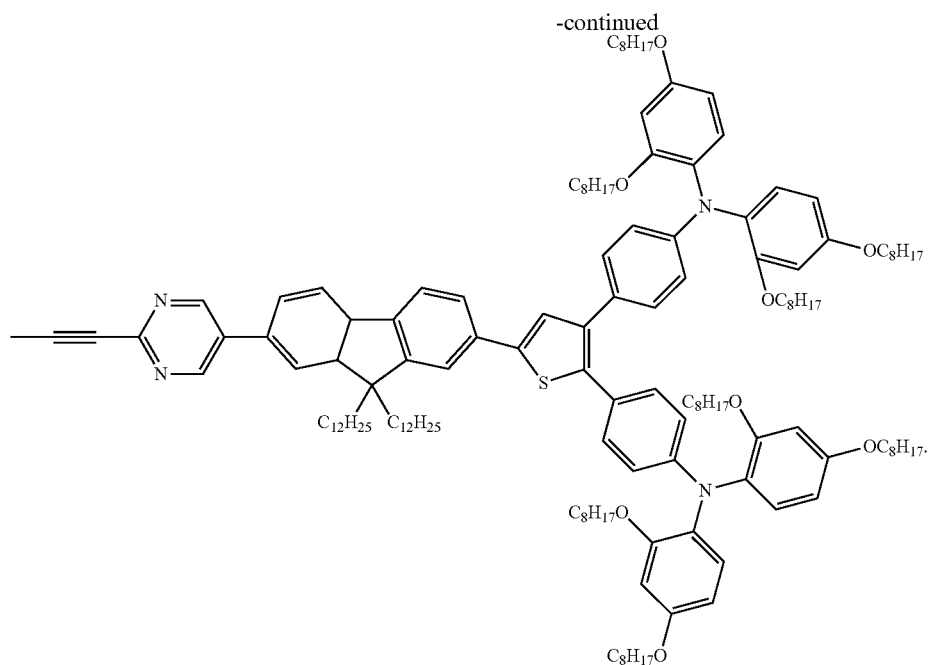
3. The compound of claim 1, wherein $A_1$ is selected from the following moieties
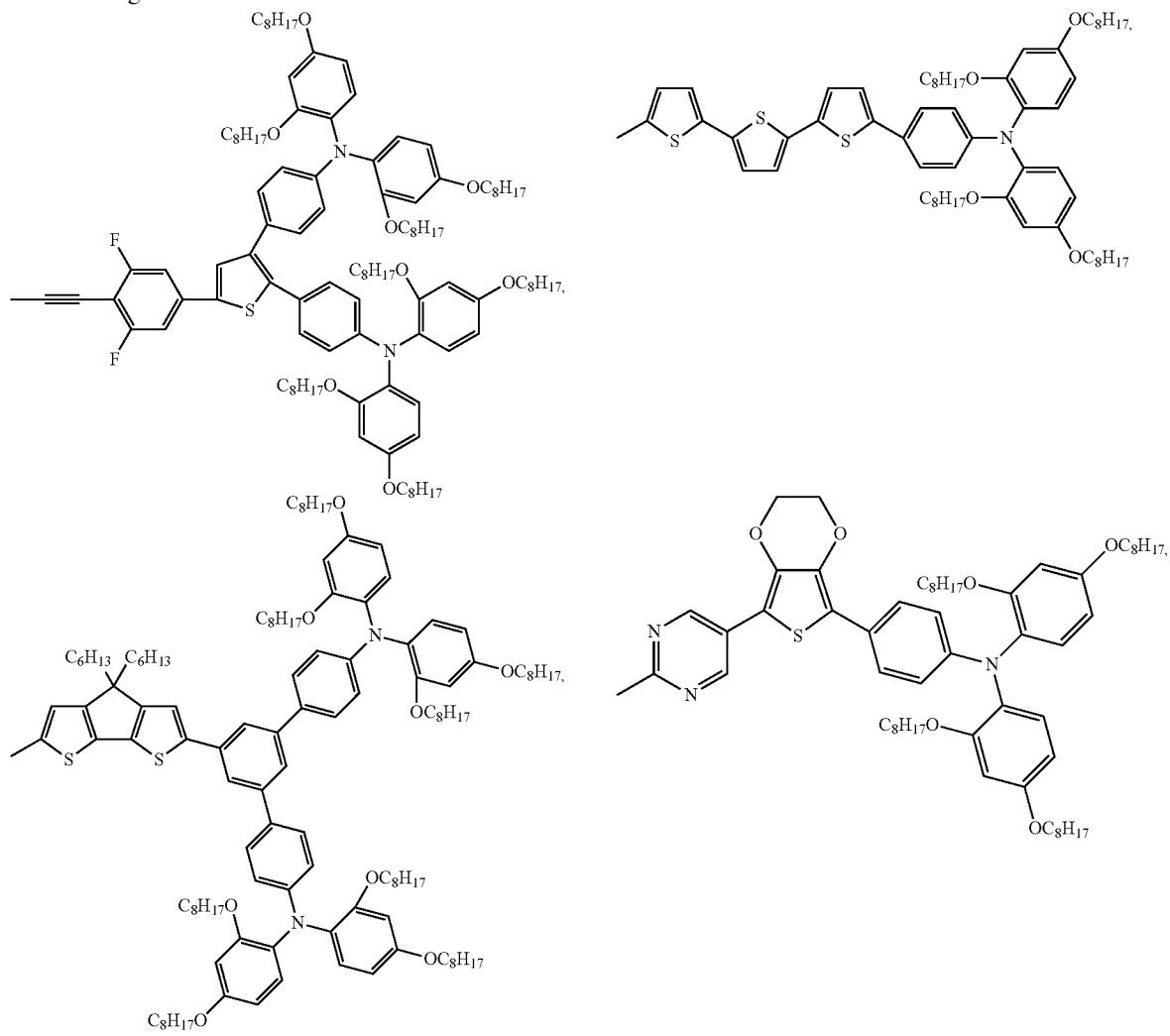

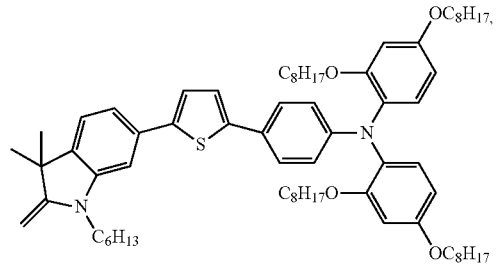
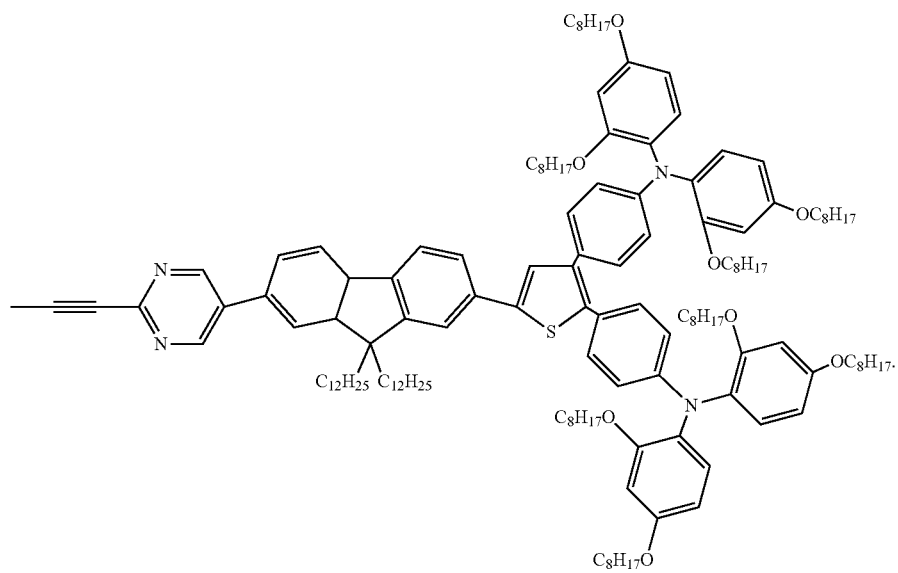
4. The compound of claim 1, which is represented by any one of
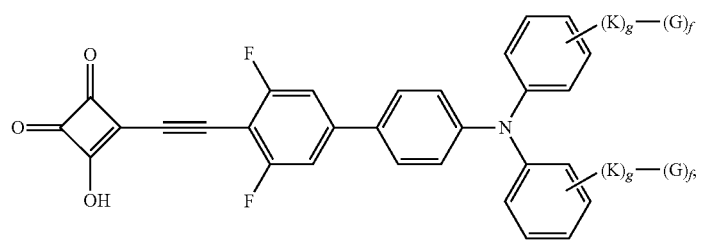
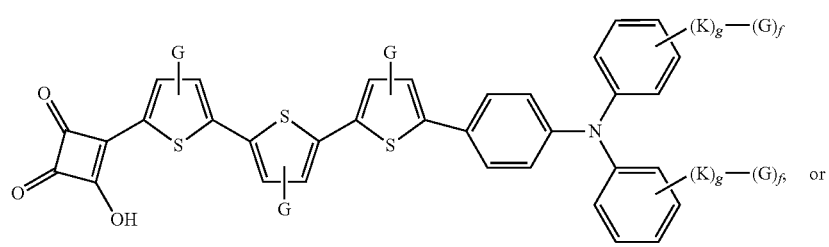

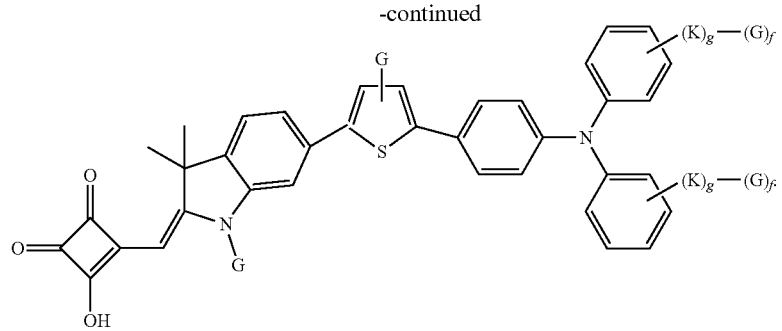
15
5. The compound of claim 1, which is any one of
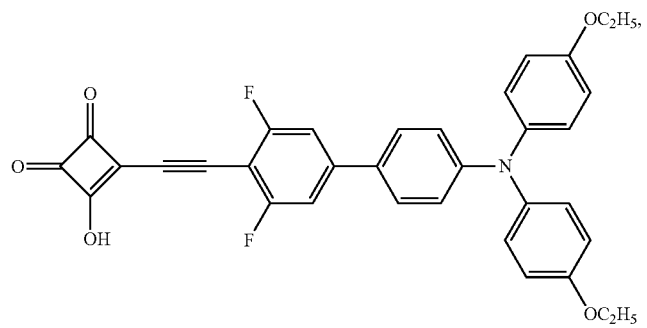
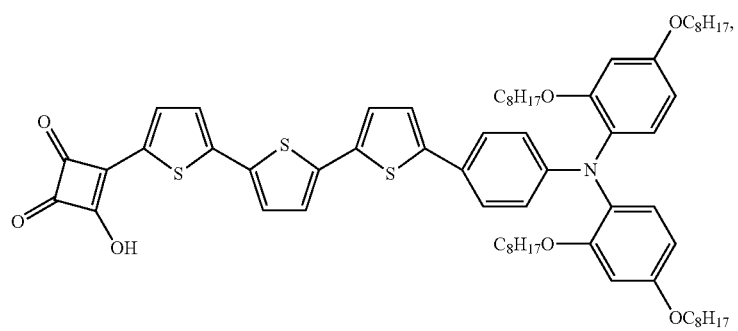
or
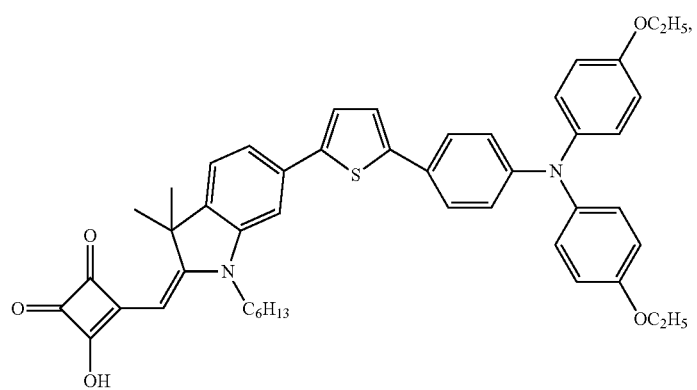

-continued

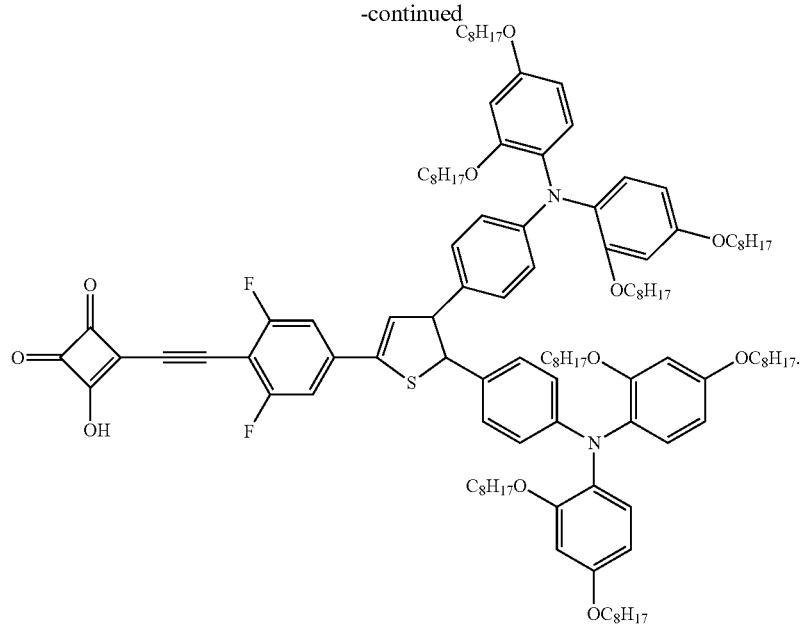

6. The compound of claim 1, wherein the compound is

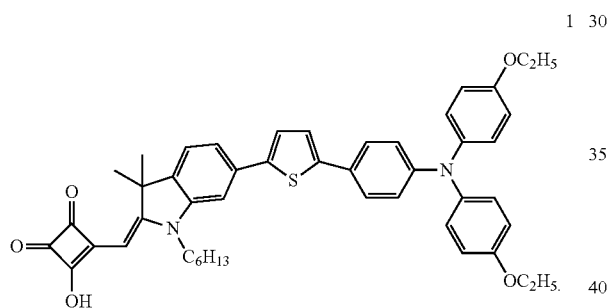

7. The compound of claim 1, which is represented by

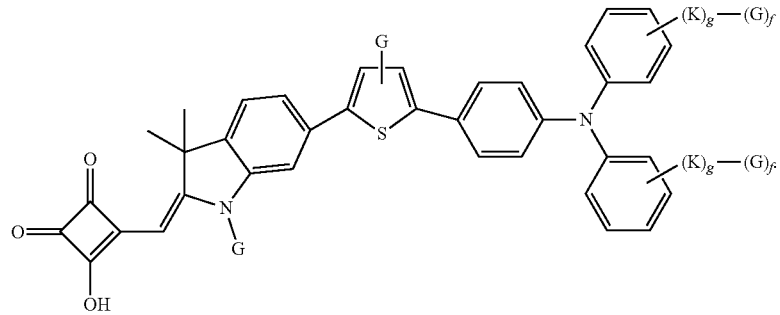

8. A light-emitting device, a Schottky barrier diode, a rectifier, a field effect transistor, a photovoltaic device, a photochemical device, a memory device, a sensing device, a display, or a photo-catalytical water splitting device that comprises:

a compound comprising a squaric acid or croconic acid group as anchoring group, said compound represented by formula (2):

wherein, in formula (2), n is 1 or 2,
wherein $A_1$ is selected from the following moieties
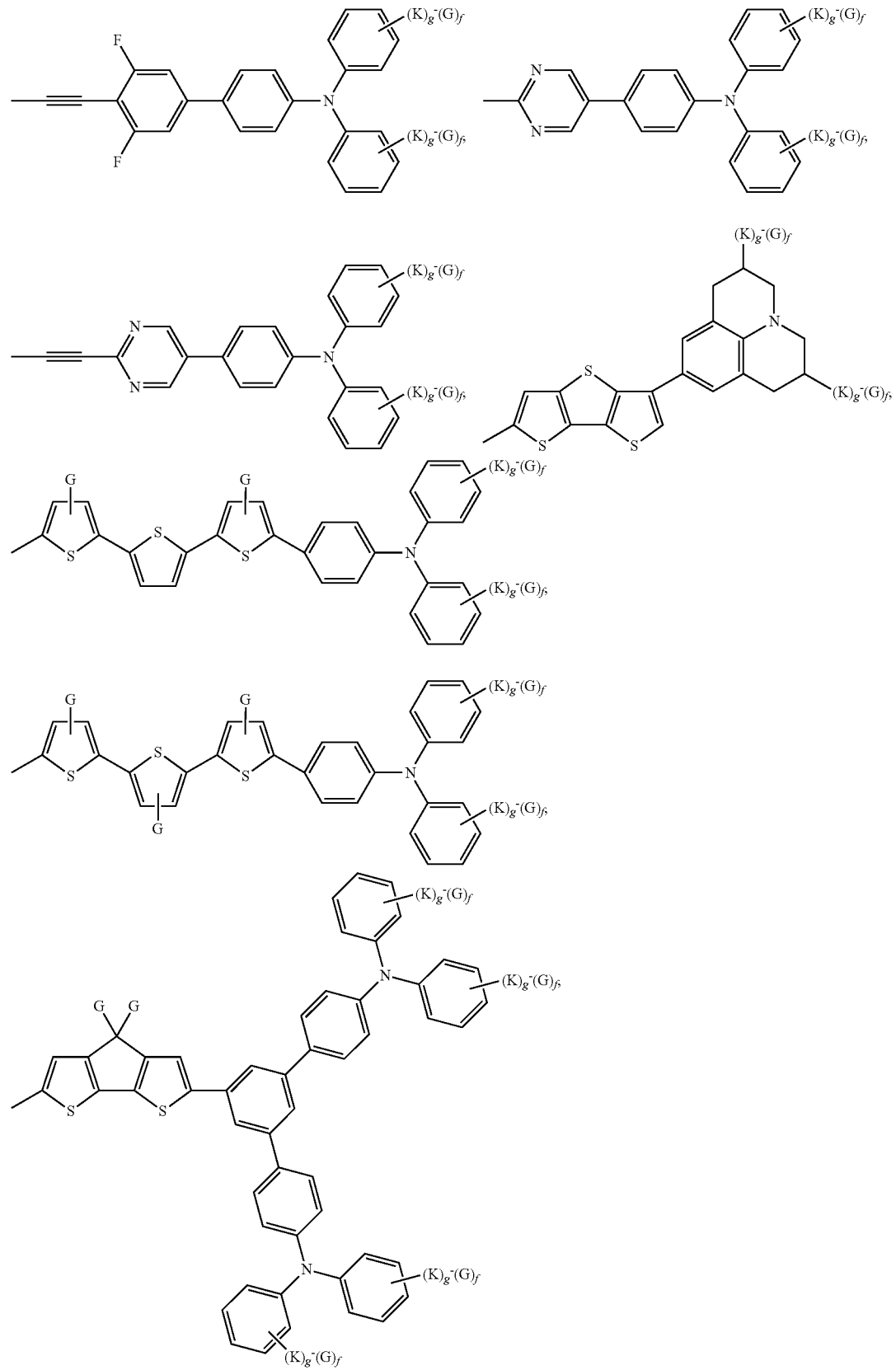

-continued
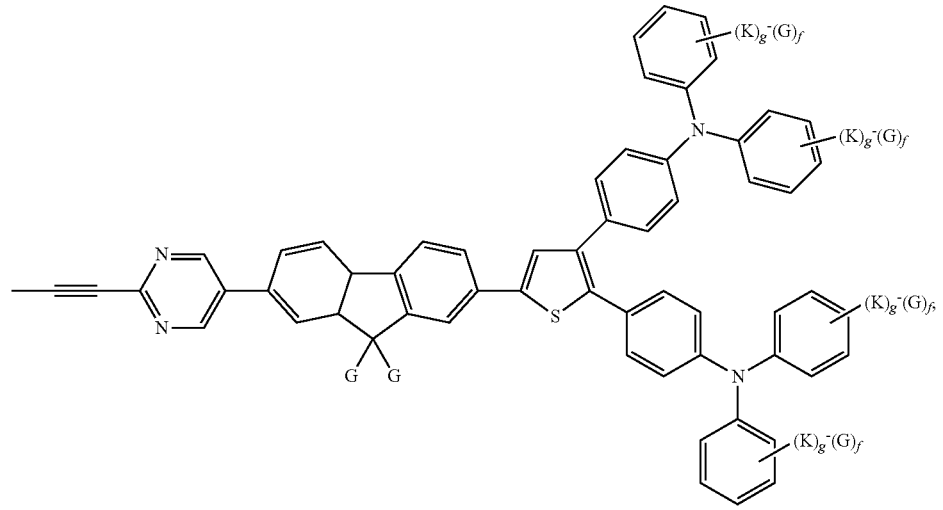
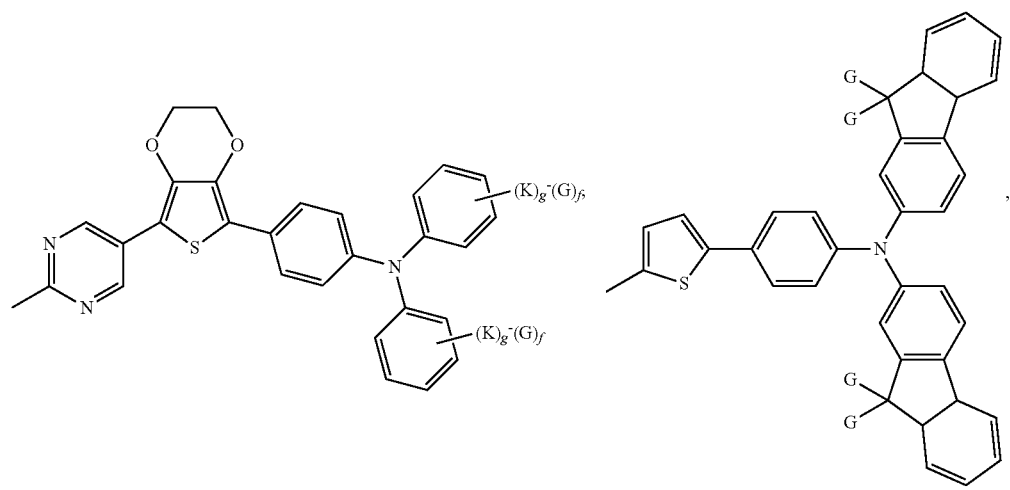
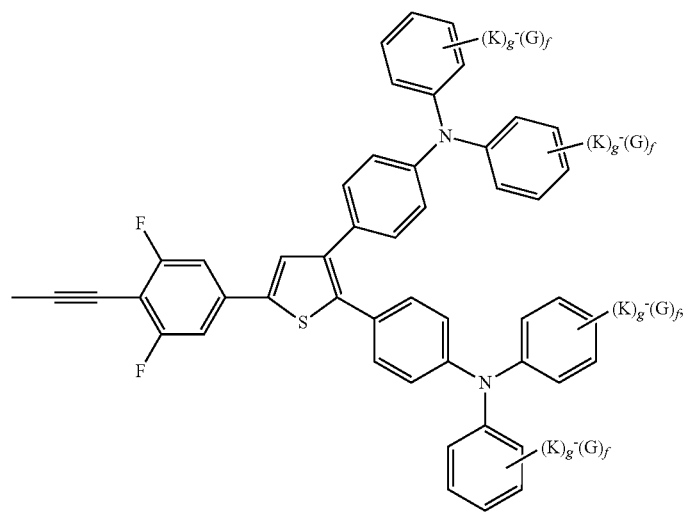

-continued

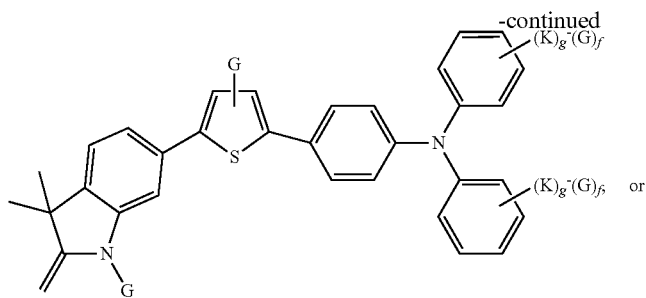

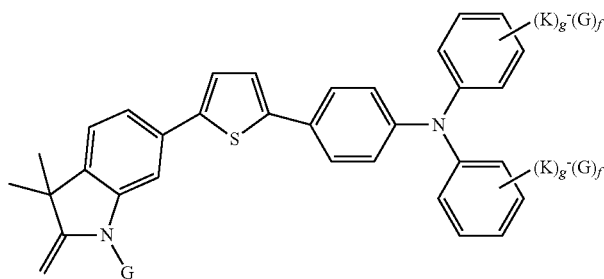

wherein, at each occurrence and independently:
G is a cyclic or acyclic substituted, or straight or branched alkyl;
f=1 or 2;
K is O, S, or N;
g=0 or 1,
wherein the alkyl, alkoxy, amine, thiole group of —(K)$_g$-(G)$_f$ can be one or more attached to the aryl and heteroaryl rings, in o-, m-, p-position.

9. An assembly for use in an electronic device, said assembly comprising:
a) a conducting substrate, a semiconducting substrate, or an insulating organic or inorganic substrate, said substrate having a surface,
b) a layer of a compound present on said surface, wherein said layer is covalently attached to said surface via the squaric acid or croconic acid group of said compound, and
c) an organic layer, an inorganic layer, or an electrolyte layer deposited on said layer, wherein said
said compound is a compound comprising a squaric acid or croconic acid group as anchoring group, said compound represented by formula (2):

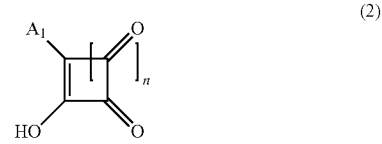

(2)

wherein, in formula (2), n is 1 or 2,
wherein A$_1$ is selected from the following moieties

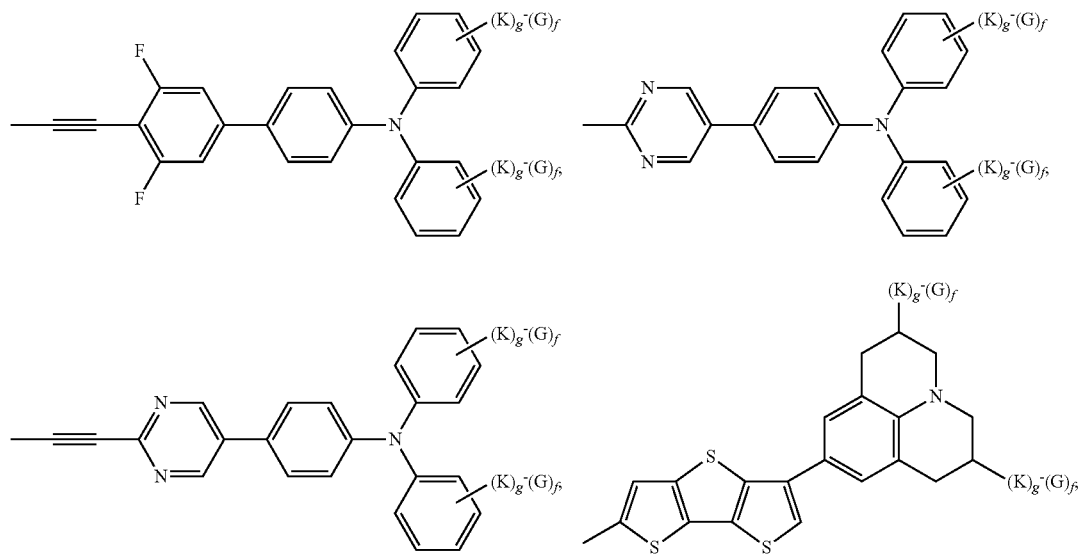

-continued
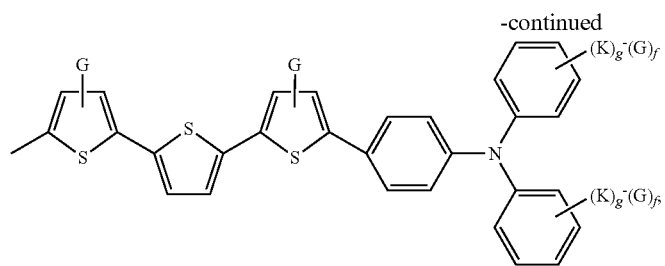
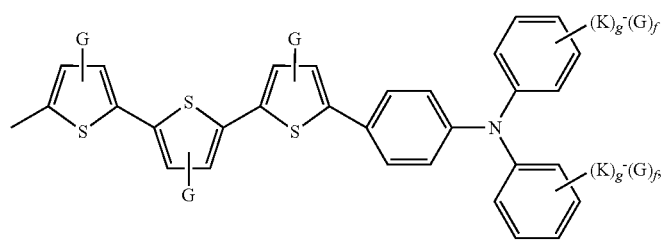
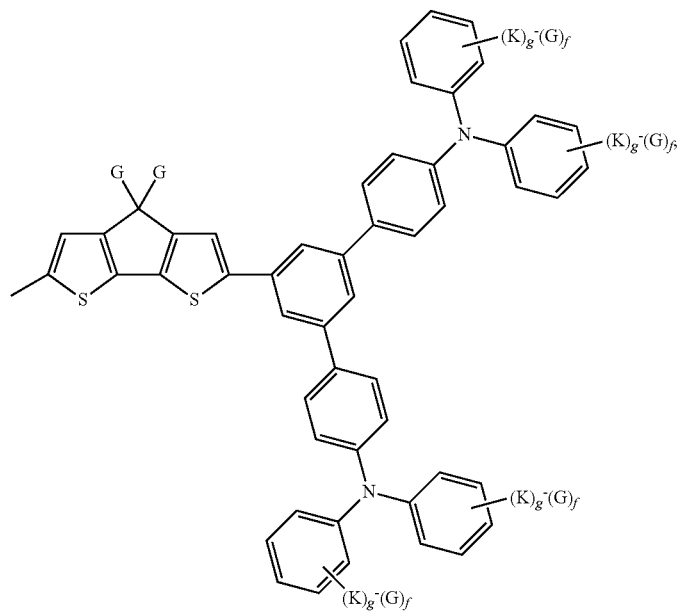
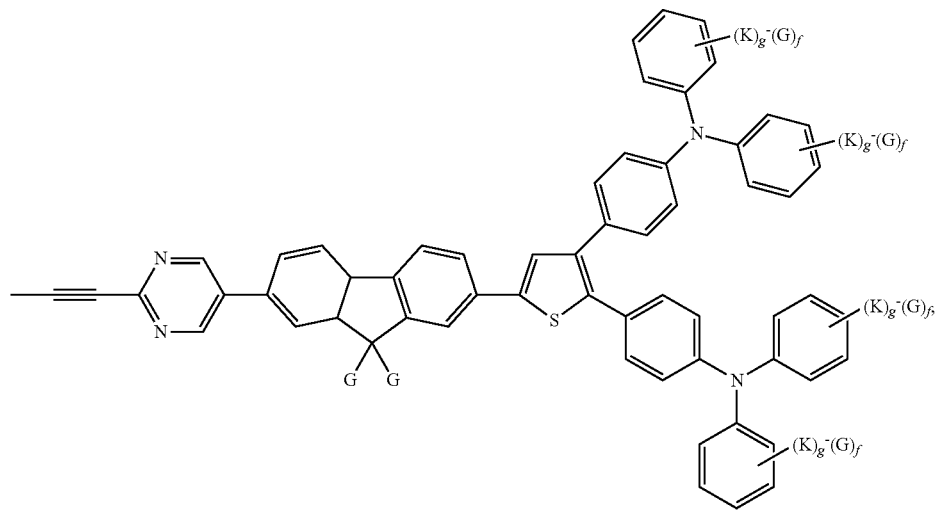

105 106
-continued
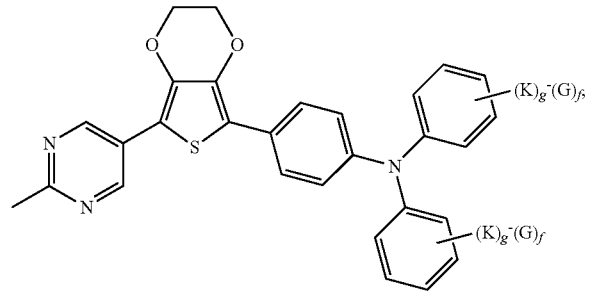
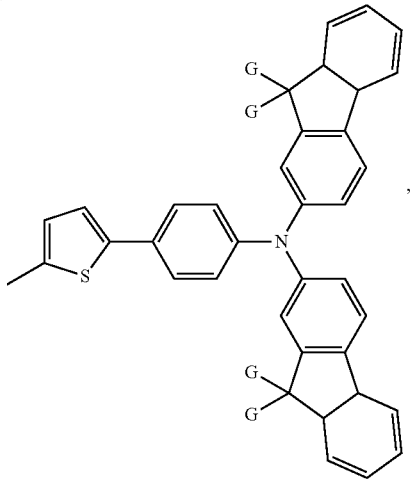
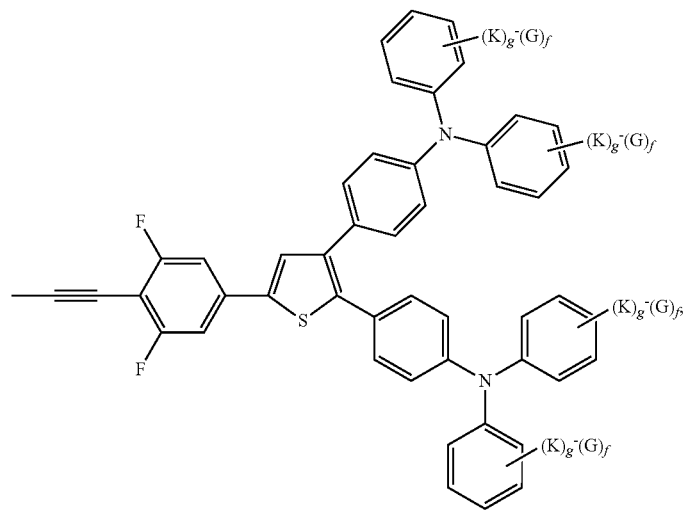
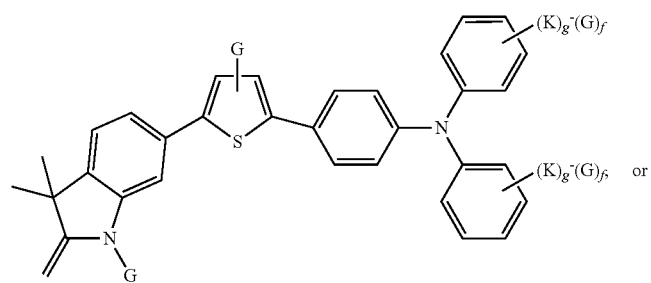 or
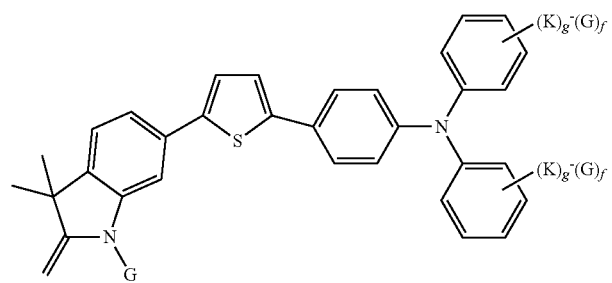

wherein, at each occurrence and independently:
G is a cyclic or acyclic substituted, or straight or branched alkyl;
f=1 or 2;
K is O, S, or N;
g=0 or 1,
wherein the alkyl, alkoxy, amine, thiole group of —$(K)_g$-$(G)_f$ can be one or more attached to the aryl and heteroaryl rings, in o-, m-, p-position.

* * * * *